(12) United States Patent
Zdeblick et al.

(10) Patent No.: US 7,762,138 B2
(45) Date of Patent: Jul. 27, 2010

(54) PRESSURE SENSOR CIRCUITS

(75) Inventors: Mark Zdeblick, Portola Valley, CA (US); Lawrence Arne, Redwood City, CA (US); Nilay Jani, Palo Alto, CA (US); Haifeng Li, Mountain View, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 0 days.

(21) Appl. No.: 12/137,439

(22) Filed: Jun. 11, 2008

(65) Prior Publication Data
US 2009/0013791 A1 Jan. 15, 2009

Related U.S. Application Data

(63) Continuation of application No. 11/610,422, filed on Dec. 13, 2006, now Pat. No. 7,398,688.

(60) Provisional application No. 60/750,640, filed on Dec. 13, 2005.

(51) Int. Cl.
*G01L 7/00* (2006.01)

(52) U.S. Cl. ........................................ 73/700; 600/513

(58) Field of Classification Search ........... 73/700–756; 600/513
See application file for complete search history.

(56) References Cited

U.S. PATENT DOCUMENTS

| 4,003,379 | A |   | 1/1977  | Ellinwood, Jr. |  |
|-----------|---|---|---------|----------------|---|
| 4,292,618 | A |   | 9/1981  | Tanabe et al.  |  |
| 4,503,709 | A | * | 3/1985  | Ruhle ............................ | 73/727 |
| 4,595,884 | A |   | 6/1986  | Miller, Jr.    |  |
| 4,858,473 | A |   | 8/1989  | LaTour et al.  |  |
| 4,878,898 | A |   | 11/1989 | Griffin et al. |  |
| 4,926,674 | A |   | 5/1990  | Fossum et al.  |  |
| 5,145,170 | A |   | 9/1992  | Morita         |  |
| 5,158,078 | A |   | 10/1992 | Bennett et al. |  |
| 5,226,413 | A |   | 7/1993  | Bennett et al. |  |
| 5,242,863 | A | * | 9/1993  | Xiang-Zheng et al. | 438/53 |
| 5,259,248 | A | * | 11/1993 | Ugai et al. ................... | 73/721 |
| 5,282,839 | A |   | 2/1994  | Roline et al.  |  |
| 5,289,721 | A | * | 3/1994  | Tanizawa et al. ............. | 73/727 |
| 5,368,040 | A |   | 11/1994 | Carney         |  |
| 5,535,752 | A |   | 7/1996  | Halperin et al. |  |
| 5,626,623 | A |   | 5/1997  | Kieval et al.  |  |
| 5,756,899 | A | * | 5/1998  | Ugai et al. ................... | 73/714 |
| 5,810,735 | A |   | 9/1998  | Halperin et al. |  |
| 6,580,946 | B2 |  | 6/2003  | Struble        |  |
| 6,647,796 | B2 | * | 11/2003 | Beach et al. .................. | 73/754 |
| 6,682,475 | B2 | * | 1/2004  | Cox et al. .................... | 600/37 |
| 7,007,551 | B2 | * | 3/2006  | Zdeblick et al. .............. | 73/715 |
| 7,028,550 | B2 | * | 4/2006  | Zdeblick et al. .............. | 73/715 |
| 7,073,387 | B2 | * | 7/2006  | Zdeblick et al. .............. | 73/715 |
| 7,284,441 | B2 | * | 10/2007 | Zdeblick ...................... | 73/753 |
| 2005/0021247 | A1 | * | 1/2005 | Liu et al. ..................... | 702/42 |

* cited by examiner

*Primary Examiner*—Andre J Allen
(74) *Attorney, Agent, or Firm*—Bret E. Field; Bozicevic Field & Francis LLP

(57) ABSTRACT

Implantable pressure sensors and methods for making and using the same are provided. A feature of embodiments of the subject pressure sensors is that they are low-drift sensors. The subject sensors find use in a variety of applications.

7 Claims, 42 Drawing Sheets

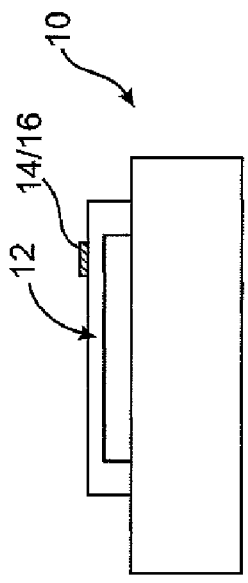
FIG. 1B (PRIOR ART)
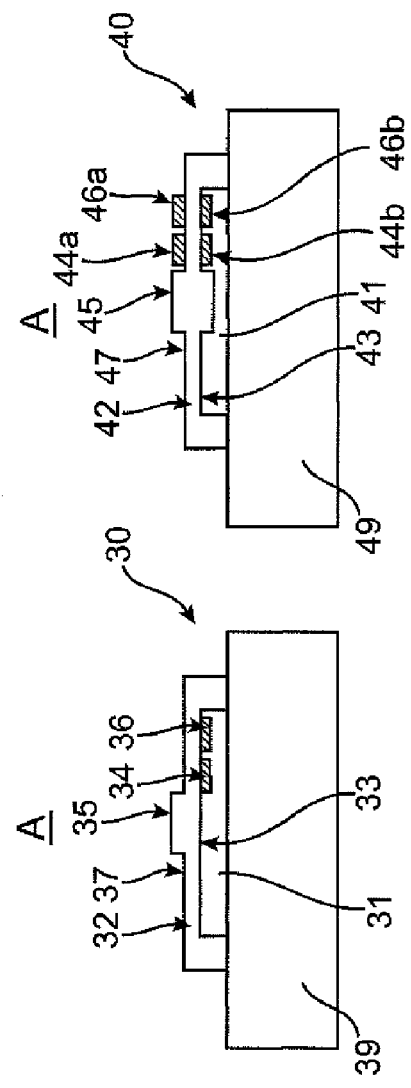
FIG. 2A
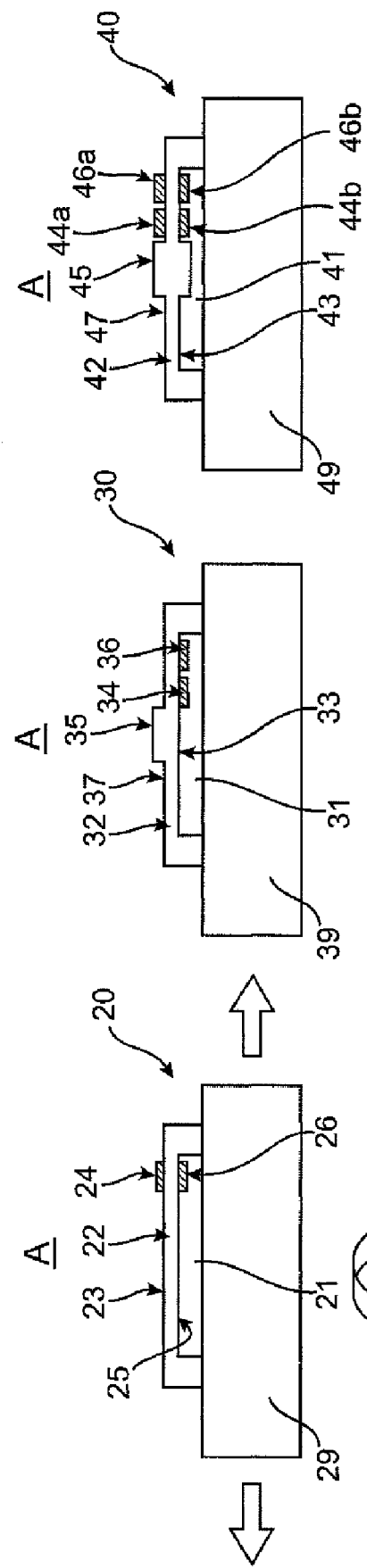
FIG. 2B
FIG. 2C

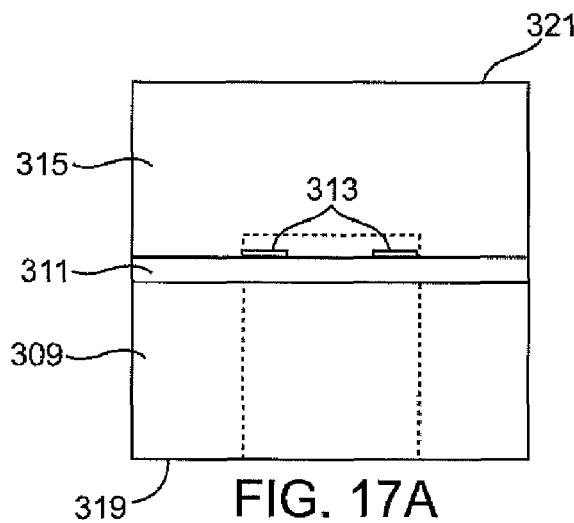 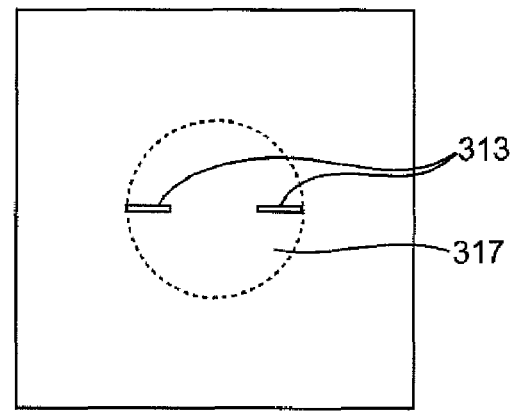
FIG. 17A    FIG. 17B
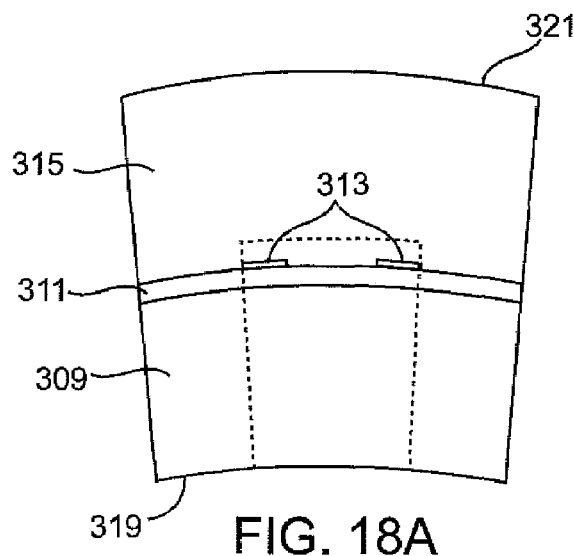 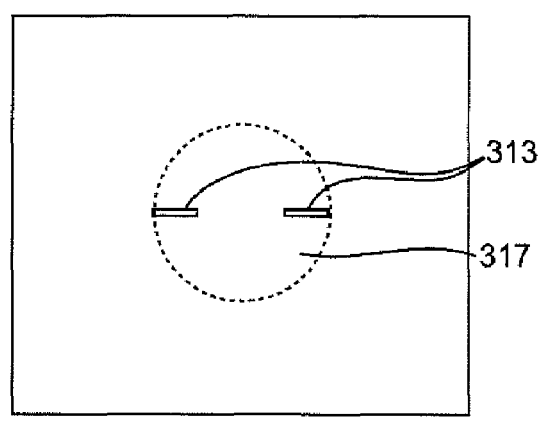
FIG. 18A    FIG. 18B
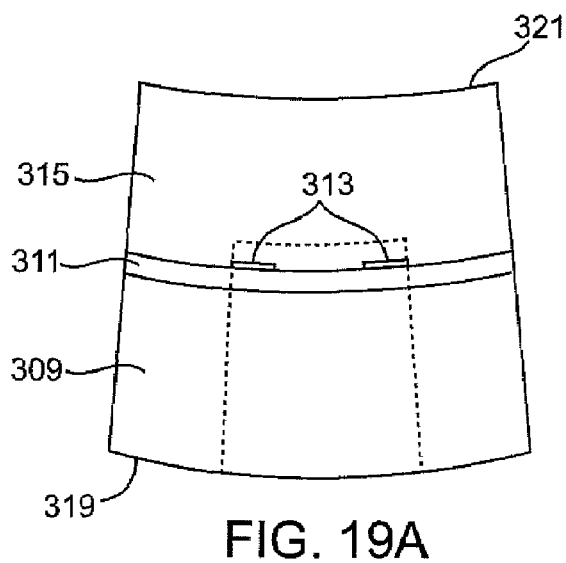 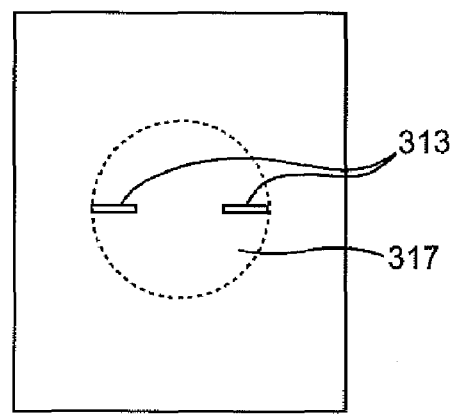
FIG. 19A    FIG. 19B

A' - A'

B' - B'

I    II

PRESSURE SENSOR CIRCUITS

CROSS-REFERENCE TO RELATED APPLICATIONS

Pursuant to 35 U.S.C. §119 (e), this application claims priority to the filing date of: U.S. Provisional Patent Application Ser. No. 60/750,640 filed Dec. 13, 2005; the disclosure of which is herein incorporated by reference. This application is also a Continuation-in-Part application of U.S. application Ser. No. 11/025,366 filed on Dec. 28, 2004; which application is a continuation application of Application Serial No. PCT/US2004/041430 filed on Dec. 10, 2004; which application pursuant to 35 U.S.C. §119 (e) claims priority to the filing dates of: U.S. Provisional Patent Application Ser. No. 60/529,325 filed Dec. 11, 2003; U.S. Provisional Patent Application Ser. No. 60/615,117 filed Sep. 30, 2004; U.S. Provisional Patent Application Ser. No. 60/616,706 filed Oct. 6, 2004; and U.S. Provisional Patent Application Ser. No. 60/624,427 filed Nov. 1, 2004; the disclosures of which are herein incorporated by reference.

INTRODUCTION

Monitoring pressures and pressure changes in a human body is often an important component of a medical or surgical diagnosis or therapy. For example, pressure changes in various body chambers, such as blood pressures in chambers of the heart, may be used for diagnosis and/or treatment of a number of conditions. One or more pressure sensors positioned in a heart chamber, for example, may allow a physician to monitor the functional ability of the heart to pump blood, such as in a patient suffering from congestive heart failure. Blood pressure monitoring in the heart may also be used to automatically activate or adjust a pacemaker, such as a rate-responsive or pressure-responsive pace maker. In some cases, one or more pressure sensors may be implanted in a heart to sense chamber pressures over an extended time period and adjust pacemaker timing or the like. Both rate-responsive pacemakers and techniques for measuring intracardiac pressures are known in the art.

Other bodily pressures and pressure changes may also be used in medical and surgical diagnosis and treatment. Pressure changes across various valves or sphincters, within body chambers or tracts such as the digestive tract, bladder filling and voiding pressures, and the like may be sensed and measured for use in a medical or surgical context.

An ideal medical pressure sensor would be both very sensitive and very stable (i.e., having very limited drift over time), while also being relatively small. Some medical pressure sensing devices, for example, should be small enough to be conveniently implanted at a desired site in a patient or to be carried on a catheter.

Advances in micromachined sensor technology have been made in order to develop small pressure sensing devices. Micromachined sensors typically measure an environmental variable, such as a pressure or acceleration, by detecting the strain induced on a sensor element, i.e., transducer. The sensor converts the strain into an electrical signal by measuring the resistance of the strained element, such as is done in piezoresistive-based sensors, or the change in vibrational frequency of that element, such as is done in resonance-based sensors. Specifically, pressure sensors detect the strain in a diaphragm that is distended in response to a pressure change, while accelerometers measure the strain caused by the displacement of a proof mass under an inertial load.

Piezoresistive pressure sensors make up the bulk of commercially available microfabricated pressure sensors. In general, this type of sensor uses two piezoresistors positioned on a circular or rectangular diaphragm to form a 90 degree angle. FIGS. 1 and 1B, for example, show a prior art microfabricated pressure sensor 10 having a circular diaphragm 12 with a radially oriented piezoresistor 16 and a circumferentially oriented piezoresistor 14. The two resistors 14, 16 are connected at one point to an output 17 of the sensor 10. The other two ends of the serially-connected resistors 14, 16 are connected to either voltage 13 or ground 15. When the trans-membrane pressure of such a diaphragm increases, the resistance of one of the resistors increases, and the other decreases. The effectiveness of the chip is adversely effected, however, by the fact that one resistance also increases and the other decreases when force is applied to the chip as a whole, such as bending, stretching and twisting forces. The sensitivity to such forces on the chip is inversely related to chip dimensions, so that the smaller the chip, the more sensitive it is to forces exerted on the chip. Such chips may be referred to as "single-point" sensors, in that they sense forces at essentially one location on a diaphragm.

In an improvement over single-point sensors, some currently available sensors include two resistors located along the perimeter of a diaphragm at separate locations, as shown in FIG. 1A. In this pressure sensor 10a, the radially oriented piezoresistor 16a and the circumferentially oriented piezoresistor 14a are distanced approximately ninety degrees apart along the perimeter of the diaphragm 12a. Thus, sensor 10a may have reduced sensitivity to stretching and bending, since the piezoresistors 14a and 16a cancel each other out somewhat. However, such a sensor 10a is equally sensitive to twisting forces as the sensor 10 shown in FIG. 1, because twisting is sensed by the piezoresistors 14a, 16a as pressure against the diaphragm 12a.

Over extended periods of use, currently available pressure sensors experience drift. Drift is the distorting changes to base line readings which occurs as a result of a number of ambient factors. Drift normally occurs over time in pressure sensors. The variable quality of baseline sensor data drift in the sense of output interferes with obtaining data which accurately reflects changes in physiologic parameters. Drift obscures accurate data both by producing false positive and false negative readings. By example, false negative results can occur when drift of base-line data readings distorts or fully obscures physiologic parameter changes in signal which would otherwise be indicative of a disease state. This occurs when the drift brings a "0" base line level into a negative range. Conversely, when sensor drift is in a positive range it can be mistaken for a change in biological parameters, running the risk of a false indication of a disease state. Unfortunately, drift is typically unpredictable, and so can not be simply factored out of calculations in order to compensate for these data distortion.

It is a requirement for implantable pressure sensors that they have very stable output. This quality is necessary to assure that the data readings from the sensors are a true reflection of the pressure that they are designed to measure. The drift characteristic of many pressure sensors can be problematic with implanted sensors, where recalibration opportunities are limited or impractical. Because of the limited ability to recalibrate implanted sensors, the failure of currently available pressures sensors to remain stable (i.e., free of drift) in base-line data output has made them unsuitable for long term implantable use.

It would be an important advancement in the art if a micromachined pressure sensor were available that was resistant to drift in order to make the many advantages of micromachined sensors available for long term implantation applications by researchers and clinicians.

RELEVANT LITERATURE

Methods for pressure-modulated rate-responsive cardiac pacing are described in U.S. Pat. No. 6,580,946. Techniques for monitoring intra-cardiac pressures are described in U.S. Pat. Nos. 5,810,735, 5,626,623, 5,535,752, 5,368,040, 5,282,839, 5,226,413, 5,158,078, 5,145,170 and 4,003,379.

SUMMARY

Implantable pressure sensors and methods for making and using the same are provided. A feature of embodiments of the subject pressure sensors is that they are low-drift sensors. The subject sensors find use in a variety of applications.

Embodiments of the subject invention provide physiological pressure sensor structures that include: a substrate; a compliant member mounted on the substrate in a manner such that the compliant member has first and second opposing exposed surfaces; and at least one strain transducer associated with a surface of the compliant member. In these embodiments, the pressure sensor structure is a low-drift pressure sensor structure.

In certain embodiments, the substrate includes an opening and the compliant member spans the opening. In certain embodiments, the structure includes at least first and second strain transducers mounted on a surface of the compliant member. In certain embodiments, the first and second strain transducers are piezoresistors. In certain embodiments, the piezoresistors are fabricated from a high gauge material, e.g., a material comprises platinum (e.g., pure platinum, a platinum alloy, etc). In certain embodiments, compliant member comprises single crystal silicon.

In certain embodiments, the first and second strain transducers are positioned on a surface of the compliant member so that their outputs respond oppositely to deflection of the compliant member resulting from differential pressure across the compliant member but respond similarly to deformation of said substrate. In certain embodiments, the first and second strain transducers are positioned on the same surface of the compliant member. In certain embodiments, the first and second strain transducers are positioned symmetrically on the same surface on opposite sides of a line of symmetry. In certain embodiments, the structures further include a boss on a surface of the compliant member. In certain embodiments, the first and second strain transducers are positioned adjacent to each other on a surface of the compliant member on one side of a line of symmetry.

In certain embodiments, the first and second strain transducers are positioned on opposing surfaces of the compliant member. In certain embodiments, the first and second strain transducers are directly opposed to each other.

In certain embodiments, the compliant member is positioned at least proximal to the structure's neutral plane.

In certain embodiments, at least one strain transducer is separated from the surface of said compliant member by a spacer. In certain of these embodiments, the spacer separates said sensor from said compliant member by a distance ranging from about from about 1 to about 1,000 µm.

Also provided are systems that include the subject sensor structures, where the systems are characterized by the presence of at least one conductive member, e.g., a wire, operatively coupled to the transducer elements of the sensor structure. In certain embodiments, the system includes a plurality of the physiological pressure sensors operatively coupled to said conductive member. In certain embodiments, the system further includes an energy source coupled to said conductive member. In certain embodiments, the system further includes a processing element for determining pressure changes in a volume in response to output signals from said transducer. In certain embodiments, the system is configured to be implanted into a patient. In certain embodiments, the system is configured so that the sensor is positioned on a heart wall upon implantation into a patient.

In certain embodiments, the method further includes producing a boss member on said first surface of said compliant layer. In certain embodiments, the first and second substrates are configured such that the compliant member is positioned at least proximal to said structure's neutral plane. In certain embodiments, the method is a method of producing a low drift physiological pressure sensor. In certain embodiments, the method further includes coupling the structure to a conductive member.

Also provided are methods for detecting a pressure change in a volume. The subject methods include contacting a pressure sensor structure according to the present invention with the volume; obtaining an output signal from the pressure sensor; and using the output signal to detect a pressure change in the volume.

BRIEF DESCRIPTION OF THE FIGURES

FIG. 1B is a side-view diagram of a prior art pressure sensor;

FIGS. 2A, 2B & 2C are side-view diagrams of various embodiments of improved piezoresistive pressure sensors according to various embodiments of the present invention;

FIGS. 17A & B provide cross sectional and planar views of the inventive sensor device with the sensor element located at or near the neutral plane of the device;

FIGS. 18A & B provide cross sectional and planar views of the device in FIGS. 17A & B experiencing a bending stress in a direction away from sensor diaphragm;

FIGS. 19A & B provide planar and cross sectional views of the inventive device shown in FIGS. 17A & B with a stress of the opposite magnitude applied to the chip from that in FIGS. 18A & B;

DETAILED DESCRIPTION

Figure 1:
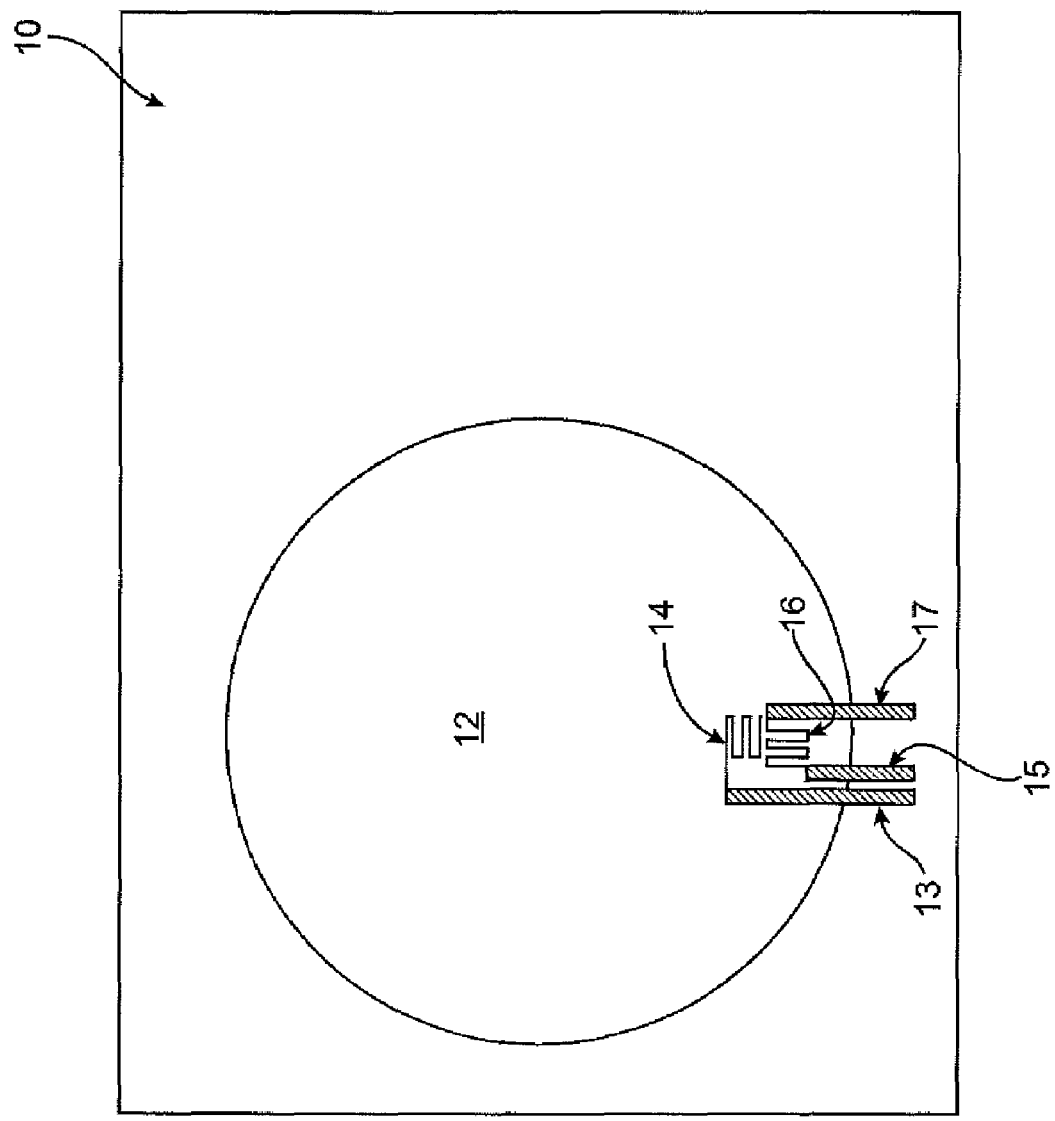
FIG. 1 is a top-view diagram of a prior art pressure sensor.
Figure 1A:
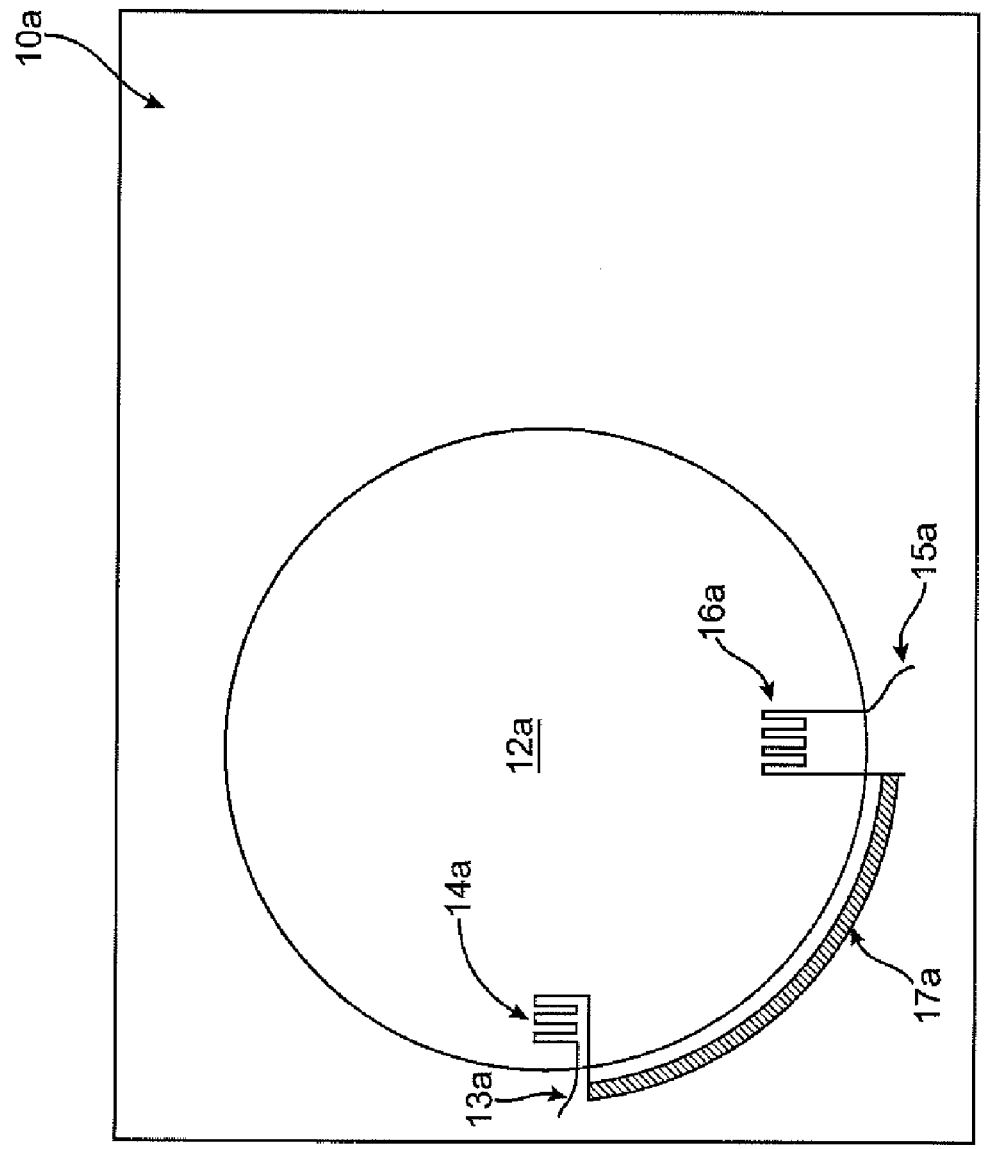
FIG. 1A is a top-view diagram of an alternative prior art pressure sensor

Low-drift implantable pressure sensors and systems including the same, as well as methods of making and using the same, are provided. The subject sensors are characterized by having at least a substrate, a compliant member mounted on the substrate in a manner such that the compliant member has first and second exposed surfaces, and at least one strain transducer associated with a surface of the compliant member. Embodiments of the subject devices exhibit low-drift. The subject devices and methods find use in a variety of different applications.

As summarized above, the subject invention provides implantable pressure sensors, as well as methods for their preparation and use. In further describing the subject invention, the subject sensors and their preparation are described first in greater detail, followed by a review of representative methods in which they find use. Also provided is a review of the kits and systems of the subject invention.

Implantable Pressure Sensors

As summarized above, the present invention provides implantable pressure sensors. The implantable pressure sensors are sensors that may be positioned in or on a body and function without significant, if any, deterioration for extended periods of time. As such, once implanted, the subject sensors do not deteriorate in terms of function for a period of at least about 2 or more days, such as at least about 1 week, at least about 4 weeks, at least about 6 months, at least about 1 year or longer, e.g., at least about 5 years or longer.

In certain embodiments, the subject sensors do not functionally deteriorate because they exhibit low drift. As such, a feature of many embodiments of the subject invention is that that the sensor structures exhibit low drift, i.e., they are low-drift pressure sensors. Sensors of these embodiments have relatively high sensitivity and stability (i.e., low drift). In one embodiment, for example, the sensor device may measure pressure changes in a volume, (i.e., an ambient), with a drift of no more that about 1.0 mmHg per year. For the purposes of this application, "a volume" means any space, chamber, cavity, substance, tissue, area or the like. In some instances a volume will comprise a chamber of a human body, such as a heart chamber, but this is only one example of a volume, and the invention is in no way limited by this example. For example, in various embodiments a volume may be a space, cavity or the like that is not in a human body, and sensors of the present invention may be used in a wide variety of non-medical contexts. Therefore, although the following discussion generally focuses on sensing pressure changes in human heart chambers, the invention is in no way limited to such an application.

In certain embodiments, the subject pressure sensors exhibit little or no drift over a period of from about 1-40 years, such as from about 5-35 years, and including from about 5-30 years. The drift diminution achieved by these embodiments is about 10-400%, most preferably 40-350%, and most preferably 50-300%, as compared to the prior art structure shown in FIGS. 1 to 1B.

Drift rates of a given sensor structure may be determined by monitoring the output of the sensor vs. time when the device is employed in a typical use environment, or model thereof. In such tests, drift may be assessed by maintaining pressure at a stable value, e.g., constant value, and monitoring the output of the sensor over time in order to ascertain any changes in the output, which are then employed to determine the drift of the device.

The drift test that is employed may be one that accelerates the drift process beyond that which occurs naturally in an in situ environment, e.g., so as to provide for the acquisition of useful data without requiring waiting for the full lifetime of a sensor to pass. There are various methods that can be employed to accelerate the external, challenging factors which result in pressure sensor drift. The simplest way to accelerate drift is to elevate the temperature to which the sensor is subject. It is conventional in the art that, for every ten degree centigrade increase in temperature beyond the intended temperature of sensor use, the observed drift will increase by a factor of two. For example, if drift is monitored at a temperature of 50° C. higher than the intended operating temperature, a 32-fold acceleration in the drift is observed. As a result, in this accelerated drift environment, for every day of observation, the device would experience the same amount of drift that would normally be experience in 32 days at the normal operating temperature. As such, drift assays that may be employed include increased temperature drift assays.

When the specific cause of the drift can be identified, drift acceleration tests can be tailored to evaluate the sensor response due to that specific cause. By example, if the fundamental source of drift is due to a mismatch in the thermal expansion coefficient of the different materials that make up the sensor, drift can be accelerated by changing the temperature. This would also be the case where drift was due to material differences between the sensor and the packaging in which the sensor resides. Specifically, drift due to mismatched thermal expansion coefficients can be evaluated by cycling the temperature between −5° C. and 95° C., e.g., for about 5, 10 or 50 or more cycles. This evaluation process, when accomplished, while monitoring the output, will give an indication of the stability of the sensor and its immunity to drift from thermal expansion mismatch sources.

A fundamental cause of a drift is mechanical stress. Mechanical stress is due to such factors as the bending of the package on which the sensor is placed. To evaluate an accelerated test of drift, a fixture is designed that applies a known mechanical deformation to the sensor. The output is then monitored to evaluate the accelerated drift rate. By example, a three-point bending test fixture can be usefully employed in this manner. Similarly, if the fundamental cause the drift is chemical in nature, the drift can be accelerated by exposing the sensor to a chemical environment that is harsher than the normal operating environment. By example, if the major source of drift is caused by corrosion due to saline, one can place a sensor in a concentrated saline solution and monitor the output. Where multiple factors effecting drift are major players in the overall drift rate, it will in some cases be useful to combine several methods of testing, such as those described above. Also, adding additional challenging factors can be used to further accelerate the effect of a single faction. By example, the sensor to be tested can be challenged by being placed in a saline environment, and then adding an additional challenging factor by elevating the temperature. This approach would both accelerate saline induce corrosion of the sensor, as well as accelerate material fatigue.

Whatever drift test is employed, where in certain embodiments a drift test as described above is employed, as sensors according to the subject invention are low-drift, they will exhibit drift, if at all, of from about 1 mm Hg/day to about 1 mm Hg/20 years, such as from about 1 mm Hg/week to about 1 mm Hg/10 years, including from about 1 mm Hg/month to about 1 mm Hg/7 years, e.g., from about 1 mm Hg/year to about 1 mm Hg/5 years. This low drift characteristic of the subject sensors is in sharp contrast to the drift observed in many current prior art pressure sensors, where the observed drift may be 7 mmHg/hr.

In certain embodiments, the implantable sensors may be characterized as physiologic. The phrase "physiologic" as employed herein denotes that the sensors are configured (e.g., shaped, dimensioned etc.) so that they can be positioned in or on a body of a living organism, such as a mammal, e.g., a human. In representative embodiments, sensor structures of the present invention are small enough to be conveniently implantable in a human body (and/or coupled with a catheter). In certain embodiments, the devices are configured as a rectangular chip having a length along an edge of the chip of no more than about 500 µm and a total thickness of no more than about 100 µm.

Embodiments of the sensors of the subject invention include a substantially planar substrate and a compliant member mounted on a surface thereof, i.e., positioned or disposed on a surface thereof. The compliant member may be a planar structure mounted on the substrate in a manner such that opposing planar surfaces of the compliant member are exposed, i.e., not touching the substrate surface on which the compliant member is mounted. As such, at least a portion of the top and bottom planar surfaces of the compliant member are not touching the substrate, even though the compliant member is mounted on the substrate. In addition, the subject sensor structures typically include at least one strain transducer associated with at least one surface of the compliant member, typically an exposed surface of the compliant member. By "associated with" is meant that the transducer is mounted on the compliant member surface, either directly or through a spacer element. As further elaborated below, the number of transducers that may be present on the compliant member may vary from one to a multitude thereof. Additional features of different embodiments of the subject sensors are further reviewed below.

In some embodiments, the device measures pressure changes in a volume with a sensitivity of about +/−1 mmHg on a scale of about 500-1000 mmHg.

In certain embodiments, the subject sensors structures have one or more of the following features, including two or more, three or more, four or more, as well as all of the following features, to the extent such features are compatible in a single sensor structure. In certain embodiments, a feature of the sensor structures is that the configuration of the sensor transducers is such as to provide for the low-drift characteristic. In certain embodiments, the materials employed for the different components of the structure are specifically chosen to provide for the low-drift characteristic. In certain embodiments, the compliant member of the structure is positioned at least proximal to the neutral plane of the structure so as to provide for the low drift characteristic. In certain embodiments, the sensor element(s) (i.e., transducer) is separated from the compliant member surface with which it is associated by a spacer element, e.g., to enhance a signal to noise ratio. Each of the above aspects is now described in greater detail below.

Low-Drift Sensor Component Configurations

As summarized above, in certain embodiments the subject sensor structures have a component configuration that imparts a low-drift characteristic to the sensor structure. In these embodiments, the sensor structures typically include a substrate, also referred to herein as a chip or support structure. The substrate may be a rigid structure, where in representative embodiments, the structure has dimensions to provide for sensor structures of a size described above. In many embodiments, the substrate includes a passage, which may be incomplete (such as a well configuration) or complete (such as a hole configuration).

Mounted on the substrate is a compliant member, where the term "compliant member" is used interchangeably with membrane and diaphragm. The compliant member is a flexible structure that deforms in response to pressure differentials applied across the compliant member. As such, the compliant member is an elastic material. In certain embodiments, the compliant member has a thickness ranging from about 0.1 to about 100 micrometers, such as from about 0.5 to about 10 micrometers, including from about 1 to about 5 micrometers. In certain embodiments, the compliant member spans the passage of the substrate, so as to produce a structure in which a pressure differential across the compliant member may be produced.

Associated with at least one surface of the compliant member is at least one strain transducer, where the phrase "strain transducer" means any device that is capable of transforming mechanical energy produced by deformation of the compliant member, e.g., in response to a pressure differential imposed across the compliant member, into electrical energy. The phrase "strain transducer" is used interchangeably with the phrase sensor element, and may be any kind of strain transducer, including piezoresistor, vibrational, and the like, as is known in the art.

The transducers may be positioned at any of a number of suitable locations on the diaphragm, and any suitable number, shape and/or size of transducers may be used.

In certain embodiments, the sensor structures include at least a first and second strain transducer. A feature of these representative embodiments is that the first and second strain transducers, e.g., piezoresistors, are positioned in the device so as to respond equally to forces, moments and torques applied to the substrate and respond equally and oppositely to changes in pressure in the volume, to allow for measurement of the pressure changes with limited interference from the forces, moments and torques applied to the substrate. For example, the forces, moments and torques may generally include bending, twisting and/or stretching.

In these representative embodiments, the transducers on the sensor structure respond differently to deflection of the diaphragm caused by pressure changes in the volume than they do to forces, moments and torques applied to the substrate. These forces, moments and torques, which may be referred to as "artifact," reduce the accuracy of a sensor device, especially over time. Examples of artifact forces which may affect performance of sensor structure include twisting, stretching, bending, compression, strain and the like. Transducers, e.g., piezoresistors, of "multiple-point" sensors of the present invention, in contrast to those of conventional single-points sensors, are configured to respond relatively equally to pressure changes in a volume while responding equally and oppositely to forces, torques and moments applied to the substrate. By "equally," it is meant at least relatively or approximately equally. When the piezoresistors are arranged in series, this response causes pressure changes in the volume to be sensed cumulatively by pairs of piezoresistors while forces, moments and torques are canceled out. By reducing the sensitivity of the sensor to mechanical forces and moments applied to the sensor chip, long term drift is drastically reduced.

As such, the transducers of these embodiments are associated with the surface of the compliant member so that their outputs response oppositely to deflection of the compliant member resulting from differential pressure across the compliant member, but respond similarly to deformation of the substrate.

In one aspect of this embodiment of the present invention, a sensor structure includes: a substrate; at least one compliant member, i.e., diaphragm or membrane, mounted on the substrate and having a first surface exposed to a volume and a second opposite surface exposed to an enclosed space; a first strain transducer, e.g., piezoresistor, disposed on the first surface; and at least a second strain transducer, e.g., piezoresistor, disposed on the second surface directly opposite the first piezoresistor and coupled with the first piezoresistor in series.

For purposes of further description only, the subject invention will be described in terms of embodiments where the strain transducers are piezoresistors. However, it should be noted that other types of strain transducers are contemplated, including those mentioned above, and such alternative transducers are in no way excluded from the scope of the invention simply by further describing the invention herein in terms of piezoresistive transducer embodiments.

In certain embodiments, the first and second piezoresistors may be disposed near a center of the compliant member, i.e., diaphragm or membrane. In some embodiments, the diaphragm may further include a thicker region, e.g., the form of a boss or analogous structure, at the center on at least one of the first and second surfaces. This region may serve as a stress-focusing member. In these embodiments, the first and second piezoresistors may be disposed adjacent the thicker region. Optionally, the thicker region may comprise a circular region of increased thickness on both the first second surfaces.

Some embodiments of the sensor device may further include a third piezoresistor positioned near an edge of the compliant member, e.g., diaphragm on the first surface of the diaphragm and at least a fourth piezoresistor positioned near the edge of the diaphragm on the second surface, directly opposite the third piezoresistor and coupled with the third piezoresistor in series. The third and fourth piezoresistors respond equally to forces, moments and torques applied to the substrate and respond equally and oppositely to changes in pressure in the volume, to allow for measurement of the pressure changes with limited interference from the forces, moments and torques applied to the substrate. In some embodiments, these first, second, third and fourth resistors comprise a Wheatstone Bridge. The sensor device may optionally further include a plurality of additional piezoresistors disposed along the diaphragm such that each piezoresistor disposed near the edge of the diaphragm is matched with a piezoresistor disposed adjacent the thicker region of the diaphragm. In some cases, the additional piezoresistors are disposed around the entire circumference of the edge of the diaphragm and around the entire circumference of the thicker region on at least one surface of the diaphragm.

In another aspect of the invention, a sensor structure includes: a substrate; at least one diaphragm mounted on the substrate and having a first surface exposed to a volume and a second opposite surface exposed to an enclosed space; a first piezoresistor disposed near an edge of the diaphragm on the first surface; and at least a second piezoresistor disposed near a center of the diaphragm on the first surface, in radial alignment with and coupled in series with the first piezoresistor. Again, the first and second piezoresistors respond equally to forces, moments and torques applied to the substrate and respond equally and oppositely to changes in pressure in the volume, to allow for measurement of the pressure changes with limited interference from the forces, moments and torques applied to the substrate.

Some embodiments may further include a third piezoresistor positioned near the edge of the diaphragm on the second surface of the diaphragm, directly opposite the first piezoresistor, and at least a fourth piezoresistor positioned near the center of the diaphragm on the second surface, directly opposite the second piezoresistor and coupled with the third piezoresistor in series. The third and fourth piezoresistors respond equally to forces, moments and torques applied to the substrate and respond equally and oppositely to changes in pressure in the volume, to allow for measurement of the pressure changes with limited interference from the forces, moments and torques applied to the substrate. Sensors according to this aspect of the invention may have any of the characteristics described above.

In one embodiment, a first plurality of piezoresistors is disposed circumferentially around at least a part of the edge of the diaphragm on the first surface, and a second plurality of the piezoresistors is disposed circumferentially around at least part of the first surface of the diaphragm closer to its center than the first plurality. In this embodiment, each piezoresistor of the first plurality is electrically coupled in series with one piezoresistor from the second plurality.

In certain embodiments, a first elongated piezoresistor is disposed circumferentially around at least part of the edge of the diaphragm on the first surface, and a second elongated piezoresistor is disposed circumferentially around least part of the diaphragm on the first surface, closer to the center than the first piezoresistor and coupled in series with the first piezoresistor. These and other embodiments may further include piezoresistors disposed on the second surface of the diaphragm as well as the first, and such further piezoresistors may optionally be coupled with the first and second piezoresistors in parallel.

Representative configurations of these embodiments are now further described in terms of the figures. FIGS. 2A to 2C are schematic side views of implantable medical pressure sensors according to various embodiments of the present invention. As with all figures in this application, these drawing figures are not necessarily drawn to scale, but are provided for explanatory purposes only. With reference to FIG. 2A, a sensor device 20 includes a substrate 29, a diaphragm 22 mounted on substrate 29, a first piezoresistor 24 located on a first surface 23 of diaphragm 22, and a second piezoresistor 26 located on a second surface 25 of diaphragm 22 directly below first piezoresistor 24. First surface 23 is exposed to a volume A, while second surface 25 is exposed to an enclosed space 21. The large, hollow arrows in FIG. 2A demonstrate stretching and bending forces which may be placed on the substrate 29. The positions of first piezoresistor 24 and second piezoresistor 26 generally allow them to respond equally to such bending and stretching, as well as other forces, moments and torques applied to the substrate, while responding equally and oppositely to changes in pressure in the volume, to allow for measurement of the pressure changes with limited interference from the forces, moments and torques applied to the substrate.

Referring now to FIG. 2B, another embodiment of a sensor device 30 includes a substrate 39, a diaphragm 32 mounted on substrate 39, a first piezoresistor 36 located near the edge of diaphragm 32 and a second piezoresistor 34 located near the center of diaphragm 32. Such piezoresistors may be either on a second surface 33, exposed to an enclosed space 31 (as shown in the figure), or on a first surface 37 of diaphragm 32, exposed to a volume A. Some embodiments may also include a central "boss" or thicker region 35. Thicker region 35 may extend from first surface 37 (as in FIG. 2B), second surface 43, or both (as in FIG. 2C). Generally, thicker region 35 enhances the ability of first and second piezoresistors to respond equally to forces, moments and torques applied to the substrate and respond equally and oppositely to changes in pressure in the volume, to allow for measurement of the pressure changes with limited interference from the forces, moments and torques applied to the substrate.

With reference now to FIG. 2C, another embodiment of a sensor device 40 includes a substrate 49, a diaphragm 42, and four piezoresistors disposed on diaphragm 42: a first piezoresistor 44a located on a first surface 47 near the center of diaphragm 42; a second piezoresistor 44b on a second surface 43 near the center of diaphragm 42; a third piezoresistor 46a on first surface 47 near the edge of diaphragm 42; and a fourth piezoresistor 46b on second surface 43 near the edge of the diaphragm 46b. In such embodiments, the fours piezoresistors 44a, 44b, 46a, 46b may comprise a full Wheatstone bridge.

Figure 2D:
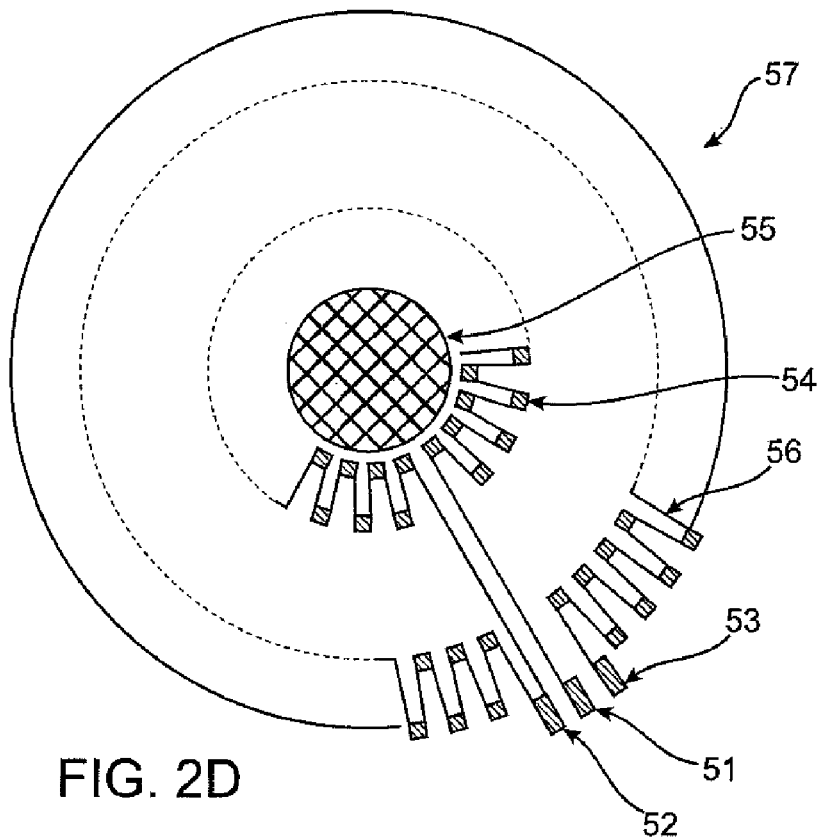
FIG. 2D is a top-view diagram of a diaphragm of a sensor structure according to an embodiment of the present invention.

Referring now to FIG. 2D, in one embodiment a diaphragm 57 of a sensor device includes a first plurality of piezoresistors 56, a second plurality of piezoresistors 54, a central thicker region 55, an output 52, a ground 51 and a voltage 53. The first plurality 56 is disposed circumferentially around the edge of diaphragm 57, extending completely or almost completely around diaphragm 57 (as designated by dotted lines). The second plurality 54 similarly extends circumferentially around diaphragm 57, but is disposed closer to the center, adjacent thicker region 55. In this embodiment, each piezoresistor of the first plurality 56 is coupled in series with the piezoresistor of the second plurality 54. In some embodiments, third and fourth pluralities of piezoresistors may be disposed on the surface of diaphragm 57 opposite the surface shown, and the first and second pluralities may be coupled with the third and fourth pluralities in parallel.

Figure 2E:
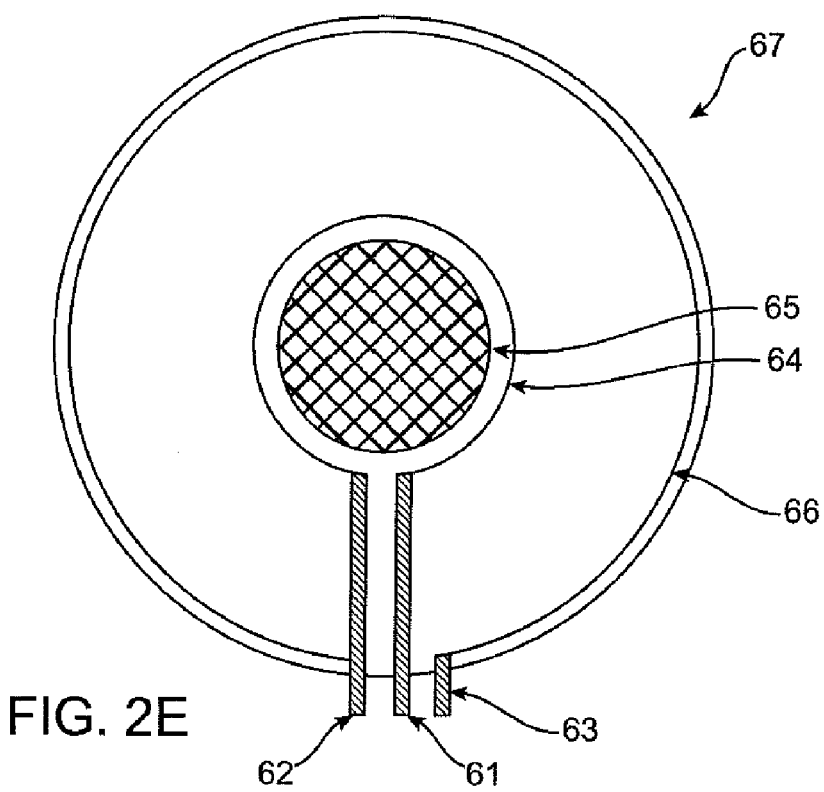
FIG. 2E is a top-view diagram of a sensor structure according to an embodiment of the present invention.

In an alternative embodiment, and with reference now to FIG. 2E, a diaphragm 67 of a sensor device may include a first elongated piezoresistor 66 disposed near the diaphragm edge and a second elongated piezoresistor 64 disposed closer to the diaphragm center, adjacent a thicker region 65. The diaphragm 67 may further include an output 62, a ground 61 and a voltage 63. Again, additional elongated piezoresistors may be disposed on an opposite side of diaphragm 67 and may be coupled with the first and second piezoresistors 64, 66 in parallel. From the examples shown in FIGS. 2A to 2E, it should be apparent that any number and configuration of piezoresistors may be used in a given embodiment of a sensor device without departing from the scope of the present invention.

Sensor structures of the present invention may have any suitable number of diaphragms and any suitable number of piezoresistors disposed on each diaphragm. For example, in some embodiments, piezoresistors may be disposed along the entire outer circumference, inner circumference, or both, of a diaphragm. Such circumferential piezoresistors may be on a first surface, a second surface, or both. Typically, each piezoresistor disposed on a diaphragm will correspond with another piezoresistor, either radially positioned on the same surface or disposed directly opposite the piezoresistor on the opposite surface of the diaphragm. Diaphragm(s) on a sensor device, furthermore, may have any suitable shape, size, thickness or the like. Although circular diaphragms are shown, for example, any other size may be used.

As mentioned above, some embodiments (FIGS. 2B and 2C, for example) include a thicker region at the center of the diaphragm. Such a region may include increased thickness on a first surface of the diaphragm, as shown in FIG. 2B, increased thickness on a second surface, or increased thickness on both, as shown in FIG. 2C. Such a thick region or boss acts to increase the stiffness of the diaphragm without increasing its outer dimensions. In some embodiments, also as shown in FIGS. 2B and 2C, one or more piezoresistors may be positioned near such a thickened region.

Pressure sensors 20, 30, 40 may have any suitable size, shape and configuration and may be made of any suitable materials. In some embodiments, for example, an implantable pressure sensor device measures about 100-500 μm on an edge and less than about 100 μm thick. The substrate may be made of silicon and/or other materials which may be microfabricated. In some embodiments, the piezoresistors are made of platinum, though other materials such as polysilicon or single-crystal silicon may be used, as described in greater detail below. As indicated above, the sensor is fabricated to have a high sensitivity and stability. In one embodiment, for example, the sensor has a sensitivity of about +/−1 mm Hg absolute on a 500-1000 mmHg scale and a drift of about 1 mmHg/5 years. Other sensitivities and specificities are also contemplated within the scope of the invention, however.

Figure 3:
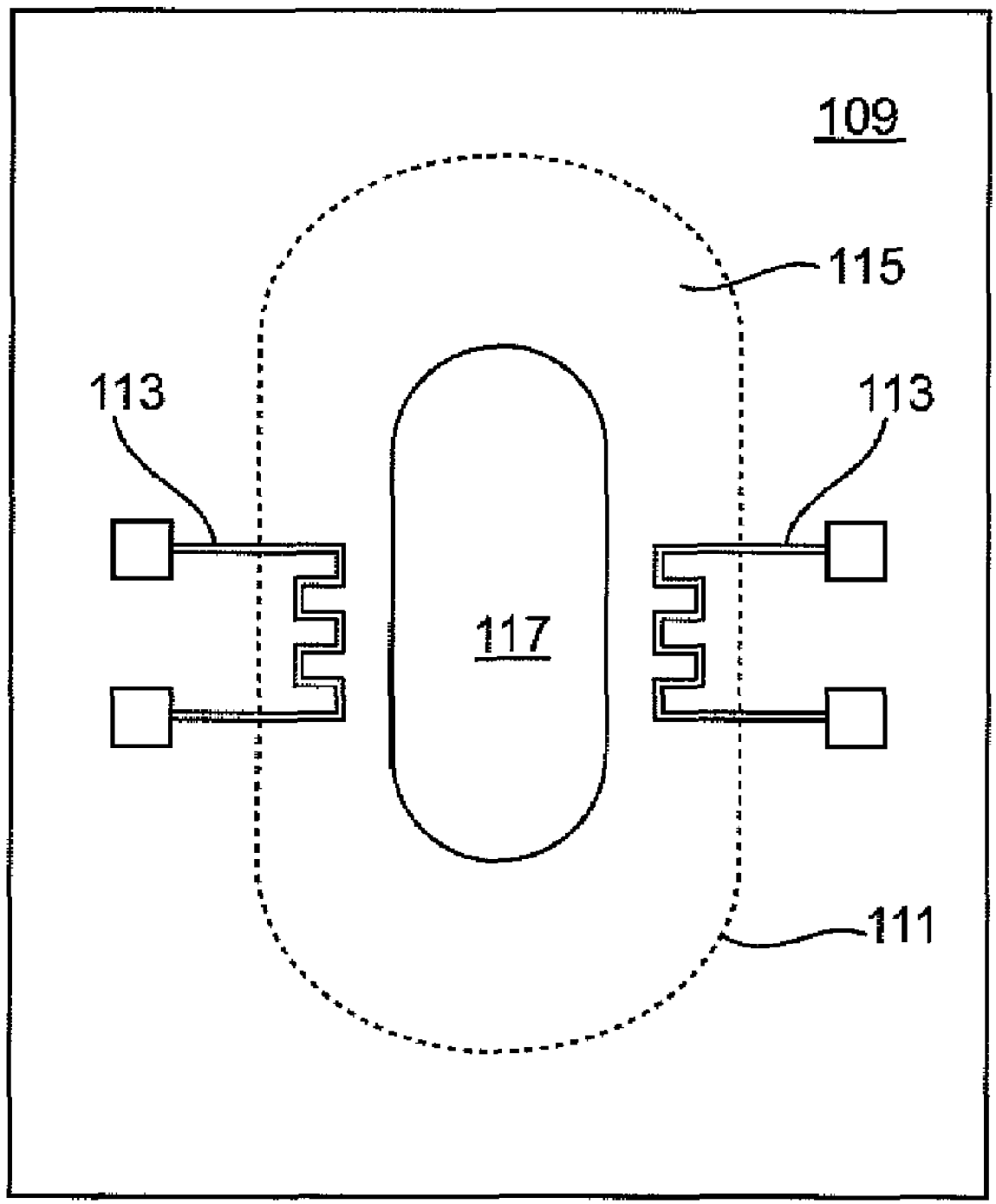
FIG. 3 provides a plan view of a device according to another embodiment of the present invention.

FIG. 3 provides a plan view of a device according to another representative embodiment of the invention. Pressure sensor chip 109 has an opening on the back side 111. Piezoresistors 113 are proved in a serpentine pattern, covering the membrane area 115, and centered on the membrane boss area 117. In this embodiment, piezoresistors 113 are provided as a single pair.

Figure 4:
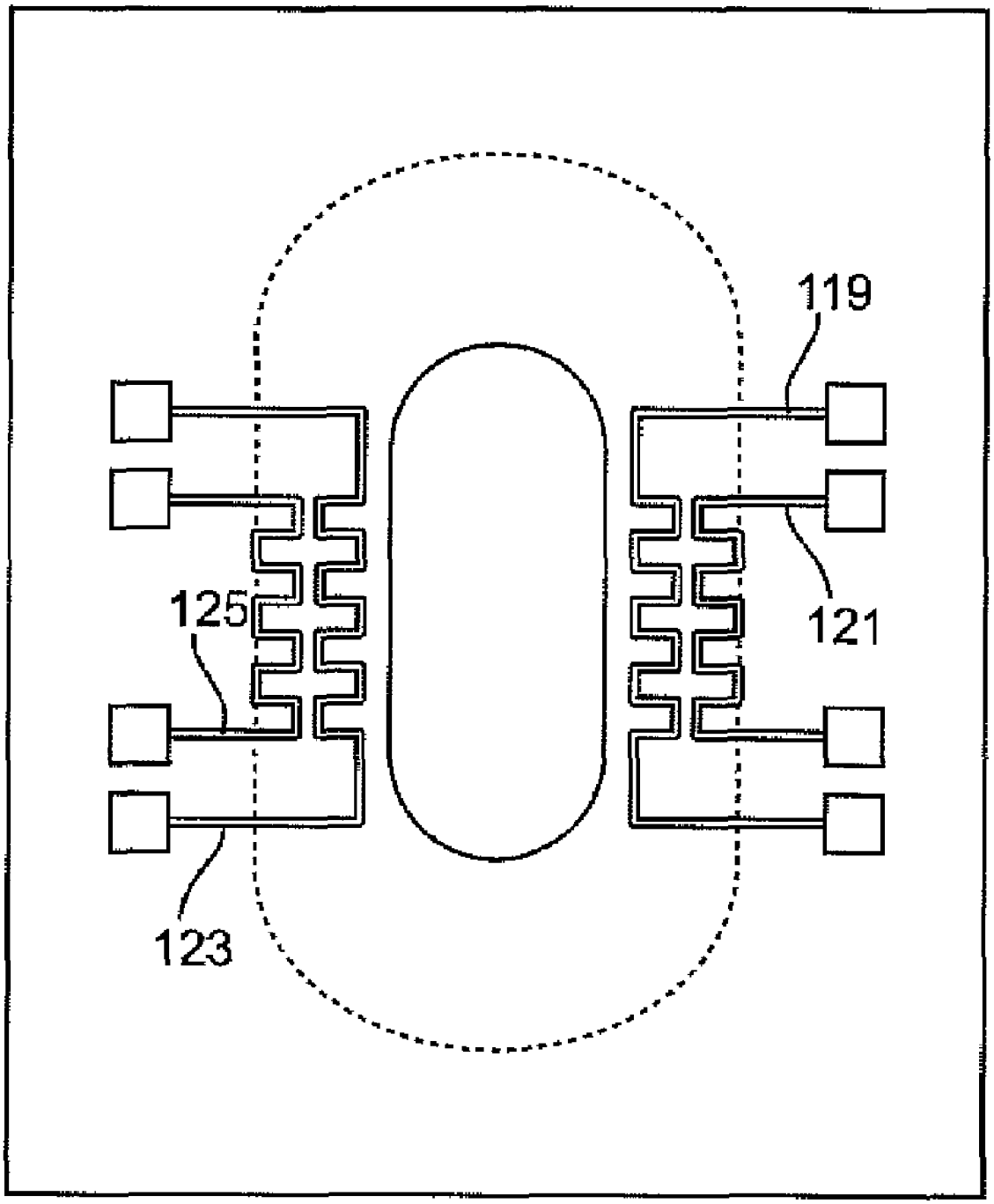
FIG. 4 provides a view of an embodiment of the pressure sensor device with four piezoresistors.

FIG. 4 shows an advantageous inventive design which goes beyond the two piezoresistors embodiment shown in FIG. 3. In FIG. 4 is shown four piezoresistors, 119, 121, 123 and 125. These piezoresistor elements are arranged in such a way that the piezoresistors closest to the boss, that is 119 and 123, will experience strain in one direction that is either compressive or tensile strain. By contrast, piezoresistors closest to the edge of the membrane, piezoresistors 121 and 125, will experience the opposite strain.

Figure 5:
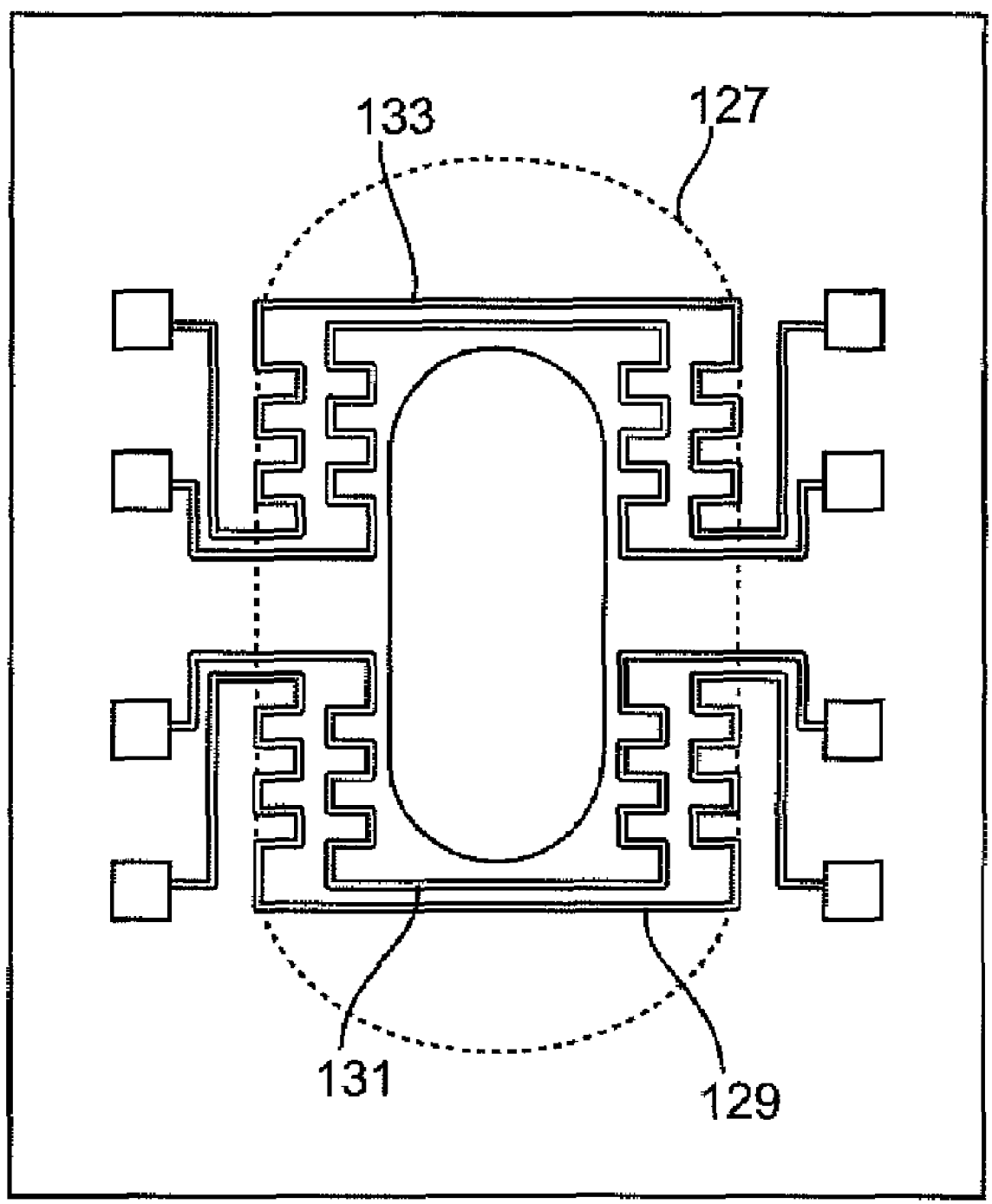
FIG. 5 provides an alternate embodiment with a different arrangement design for the four piezoresistor elements.

FIG. 5 provides an alternate embodiment with a different arrangement design for four piezoresistors elements. In FIG. 5, piezoresistors 127 and 129 are near the outside of the membrane, while piezoresistors 131 and 133 are closer the center of the membrane. This embodiment performs the same function as those inventive designs shown in FIGS. 3 and 4. However, the embodiment shown in FIG. 5 is less sensitive to fabrication tolerances.

Figure 6:
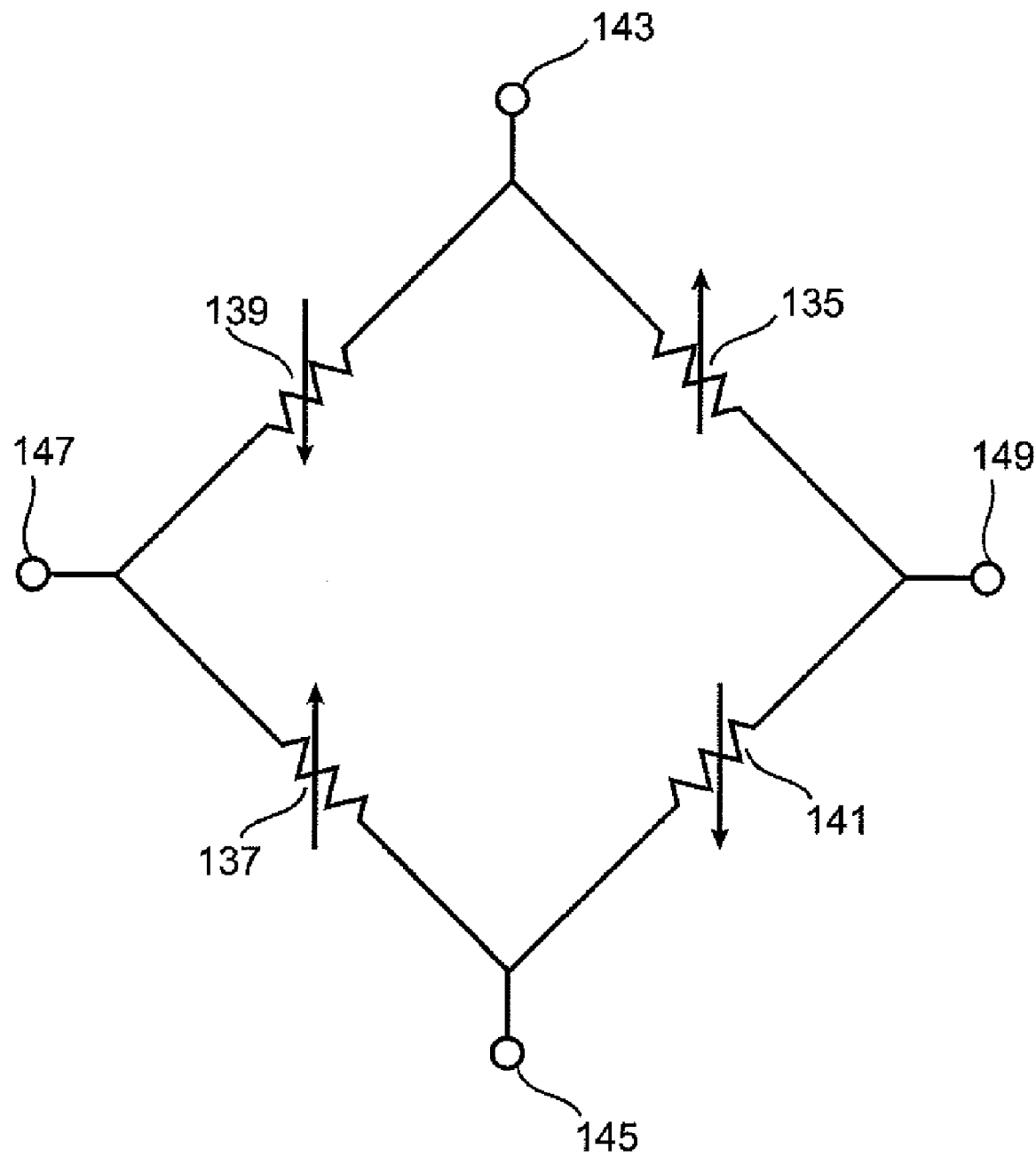
FIG. 6 provides a circuit diagram of a representative embodiment of the present invention with electrically connected piezoresistors.

FIG. 6 provides a representative embodiment of the present invention wherein the piezoresistors are connected electrically. In this view, piezoresistor 135 and 137 are the piezoresistors closest to the boss, whereas piezoresistors 139 and 141 are closest to the edge of the sensor membrane. Supply voltage is applied to electrical terminals 143 and 145, while the output voltage is measured between terminals 147 and 149.

When pressure is applied to the sensor membrane, the membrane will deform. This will, in turn, cause a stretching in the piezoresistors 135 and 137, increasing their resistance. Compression in piezoresistors 139 and 141 causes a decrease in their resistance.

In the Wheatstone bridge arrangement exemplified in this embodiment, the decrease in resistance causes the voltage at terminal 147 to become more positive than the voltage at terminal 149. By measuring the voltage between those two terminals, an increase in voltage is observed in the form of an electrical signal. This signal can be observed directly or processed by standard processing techniques to obtain digital data.

Figure 7:
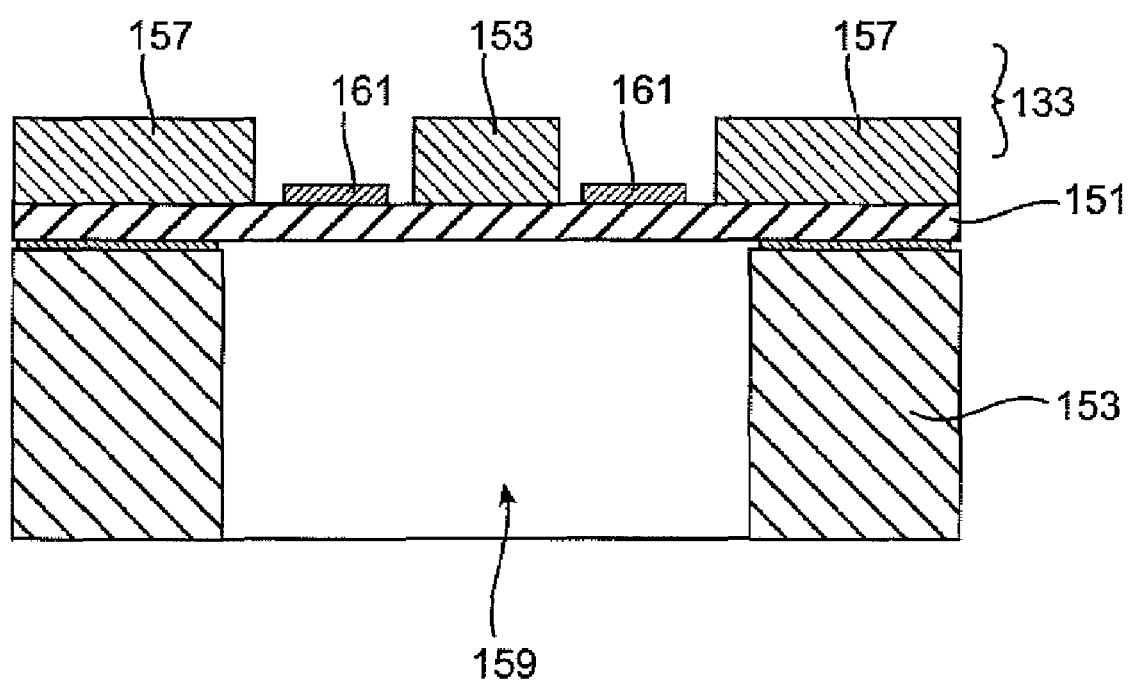
FIG. 7 provides a variation of the embodiment shown in FIG. 6.

FIG. 7 provides a variation of the embodiment shown in FIG. 6. Pressure sensor membrane 151 is supported on substrate 153. Boss layer 155 is patterned into a boss 153 in the center of the membrane 151, and additionally forms rim 157 around the edge of the membrane 151. This embodiment of the present invention is advantageous for fabrication because the alignment of cavity 159 with respect to the features on the front side, that is the boss layer 155 and piezoresistors 161, is less critical. Potential misalignment does not affect the pressure response because the size of the membrane is effectively defined by rim 157.

Figure 8A:
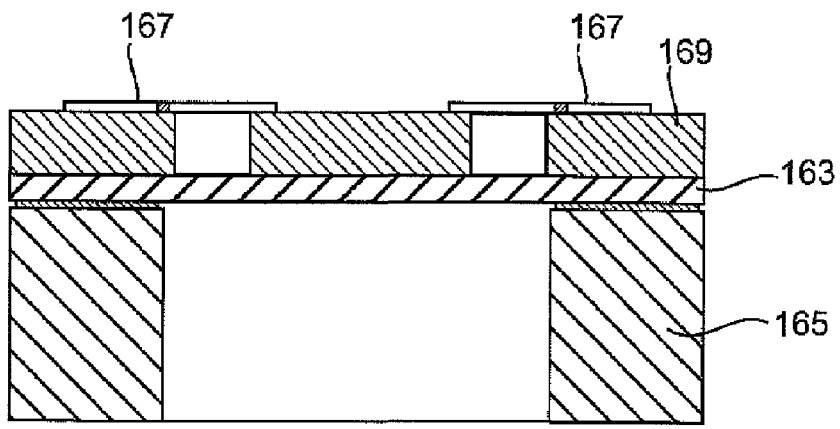
FIGS. 8A & 8B provide a view where the piezoresistors are placed on top of a boss layer.
Figure 8B:
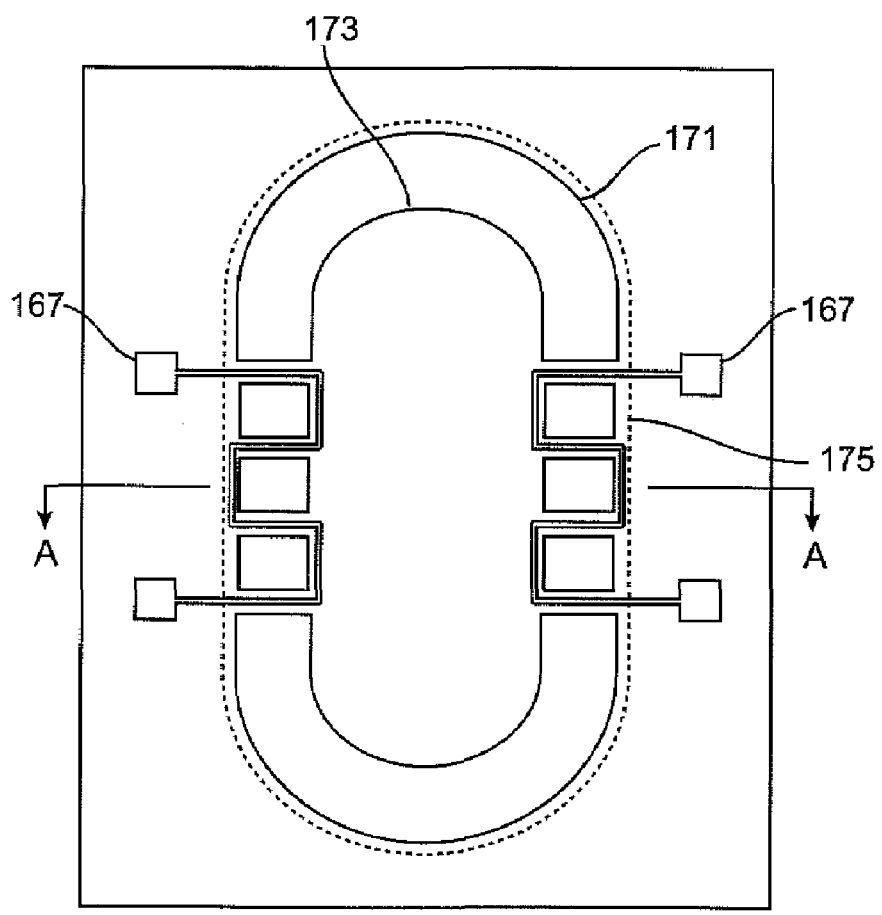

An additional variation on this approach is shown in FIGS. 8A & 8B. In this embodiment, membrane 163 is a supported by wafer 165. A feature of this variant is that piezoresistors 167 are placed on top of boss layer 169. FIG. 8B provides a plan view of the structure. Piezoresistor 167 is situated on top of the boss layer 169. In this case, the boss layer 169 is patterned to accommodate and define the membrane edge 171, the pressure enhancing boss 173, and also the traces for the piezoresistor 175.

By placing the piezoresistors 167 on top of the boss layer 169, a stress amplification effect is achieved, where the boss layer acts as spacer, as further described below. This effect is achieved because the strain measuring element, i.e., the piezoresistors 167, has been positioned further away from the neutral plane of the membrane, as is described in U.S. Patent Application No. 60/615,117 filed on Sep. 30, 2004, incorporated herein by reference as well as above, and described in greater detail below.

Figure 9A:
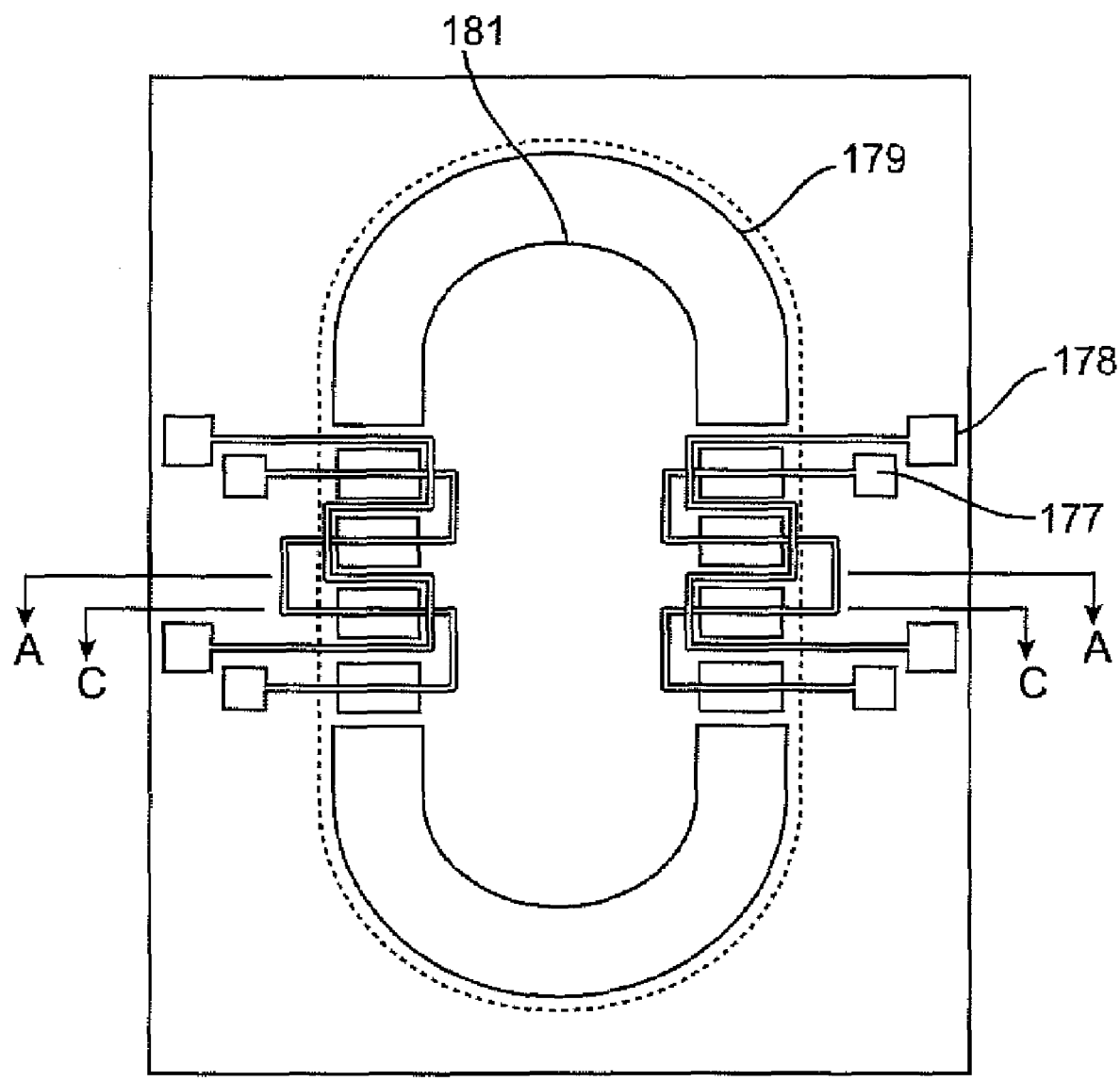
FIGS. 9 A, B & C provide a view where the piezoresistors are placed both under and on top of a boss layer.
Figure 9B:
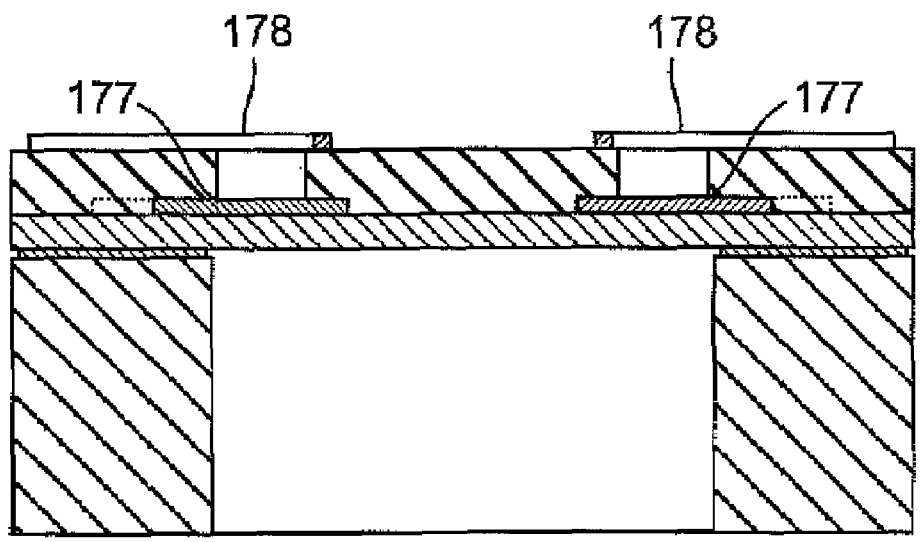
Figure 9C:
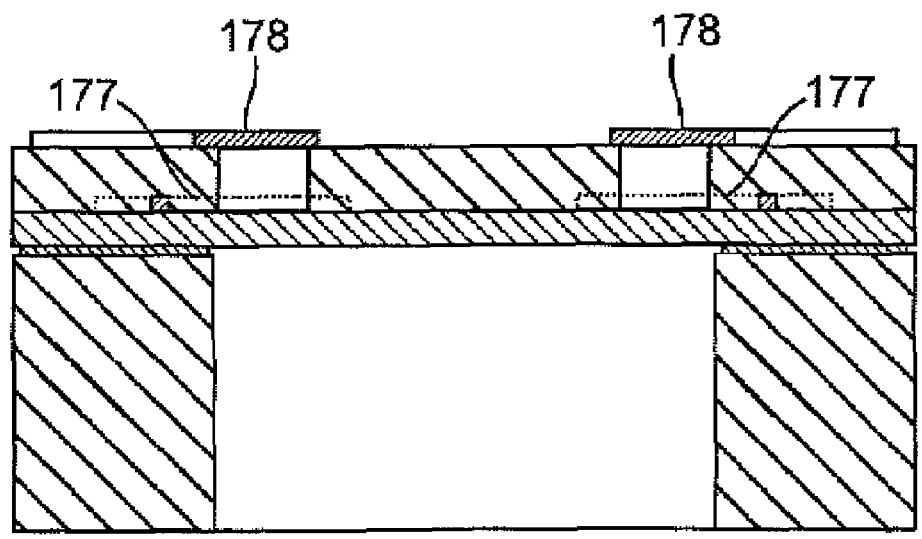

The various concepts shown in the above figures are shown coordinated in a single device in FIGS. 9A, 9B & 9C. In these views, piezoresistors 177 are situated underneath the boss layer. Additional piezoresistors 178 are provided on top of the boss layer. FIG. 9A provides a planar view of this embodiment, while FIGS. 9B and 9C provide cross sectional views. The boss layer is patterned to define the edge of membrane 179, pressure focusing boss 181, as well as a path for the top layer piezoresistor 178. The bottom layer piezoresistor 177 is deposited and patterned underneath the boss layer.

Figure 10:
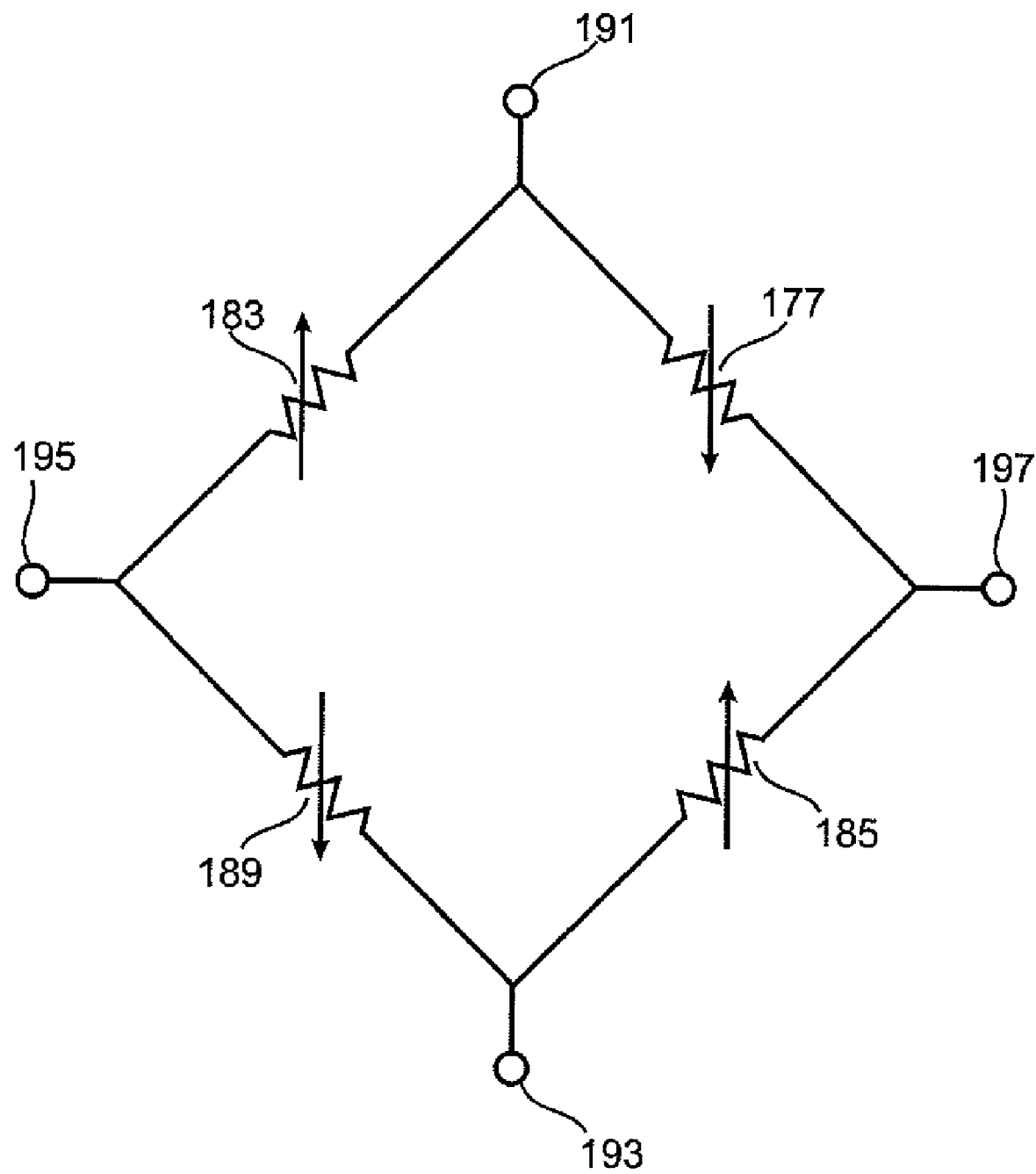
FIG. 10 provides a circuit diagram of an embodiment of the present invention.

FIG. 10 provides a view of the electrical connections between the elements as show in FIGS. 9A to 9C. Piezoresistors 183 and 185 are the bottom layer piezoresistors, while piezoresistors 187 and 189 are the top layer piezoresistors. When a voltage is supplied between terminals 191 and 193, an output proportional to the pressure will be observed between terminal 195 and 197.

Figure 11:
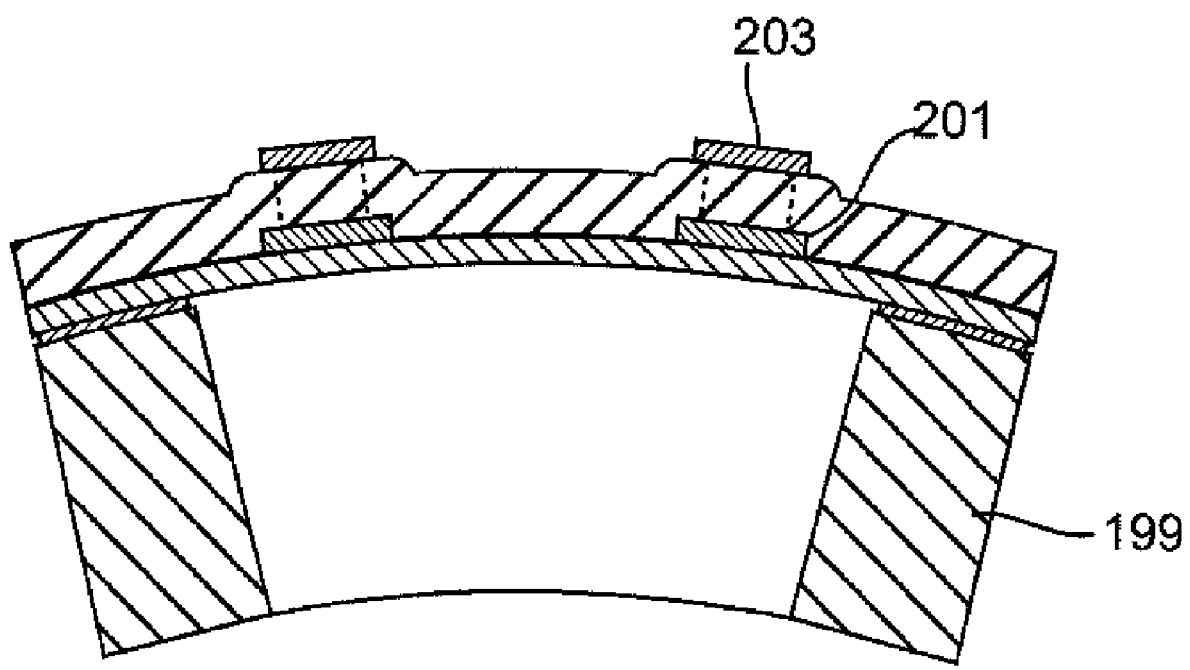
FIG. 11 provides a cross-sectional view of an embodiment of the present invention.
Figure 12:
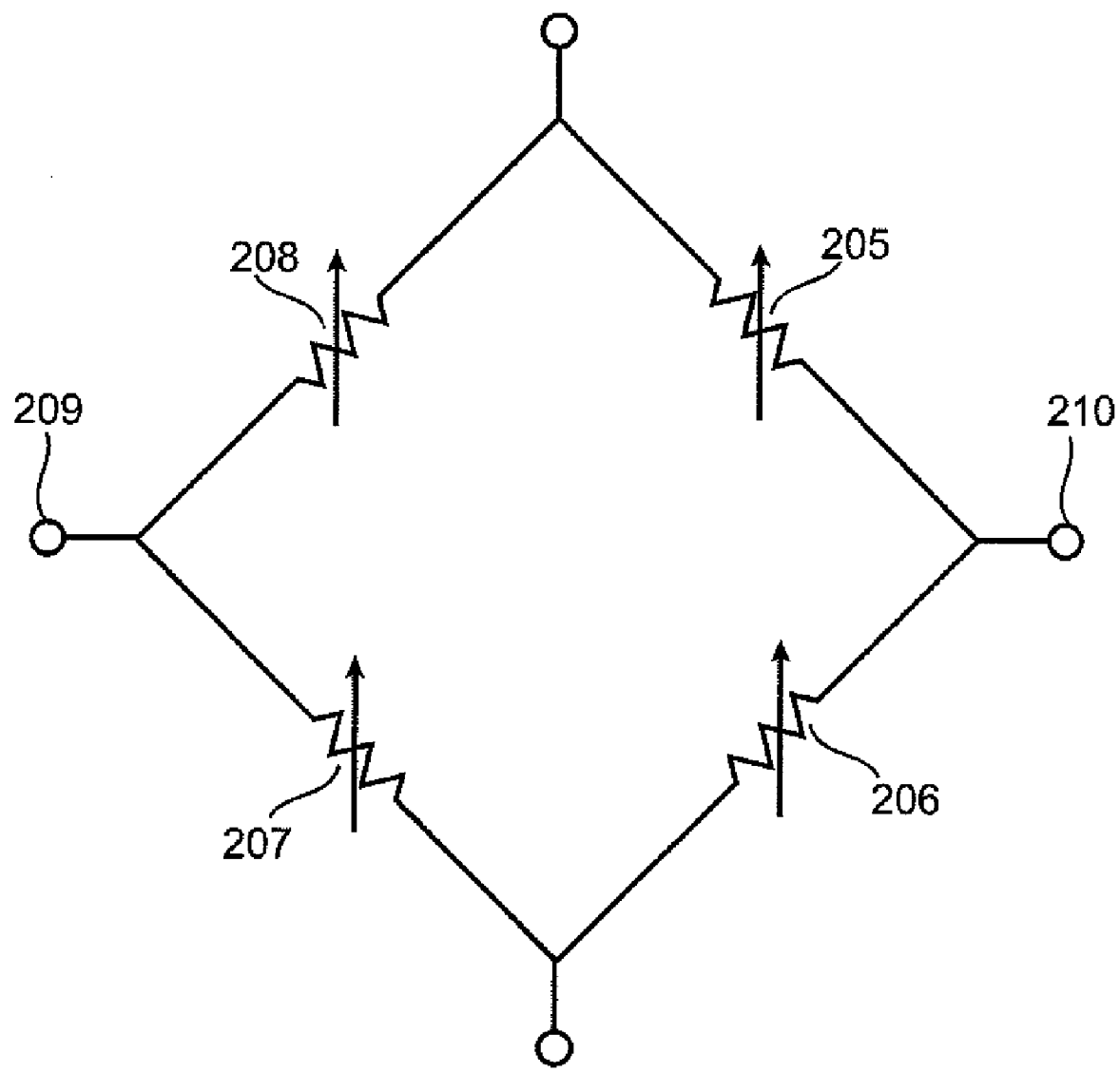
FIG. 12 provides a circuit diagram of an embodiment of the present invention.

The advantage of the particular arrangement of FIG. 10 is demonstrated in FIG. 11. This figure is a schematic view of pressure sensor chip 199 experiencing a bending stress that causes entire chip 199 to bend. From this diagram, it can be observed that this bending stress will cause piezoresistors 201 and 203 to stretch. However, because of the electrical configuration shown in FIG. 12, all four piezoresistors 205, 206, 207, and 208, will experience the same bending stress. In this way, piezoresistors 205, 206, 207, and 208 will all increase in resistance, and there would be no net change in the voltage between terminals 209 and 210. This figure demonstrates how this particular implementation is insensitive to stress applied to chip 199.

Low-Drift Component Materials

As indicated above, in certain embodiments the various components of the sensor structures are fabricated from specific materials, as well as combinations thereof, that impart low-drift characteristics to the sensor structures.

In certain embodiments, the sensor membrane is constructed of a very stable material, which is ideally purely elastic. In this manner, change, creep, or change in strain which typically occurs over time in prior art sensors are substantially limited, ideally eliminated, in sensor membrane. The major design advancement is to assure that the pressure sensing elements, typically piezoresistors, are very stable, so that their resistance undergoes very limited or no change over time.

Figure 13:
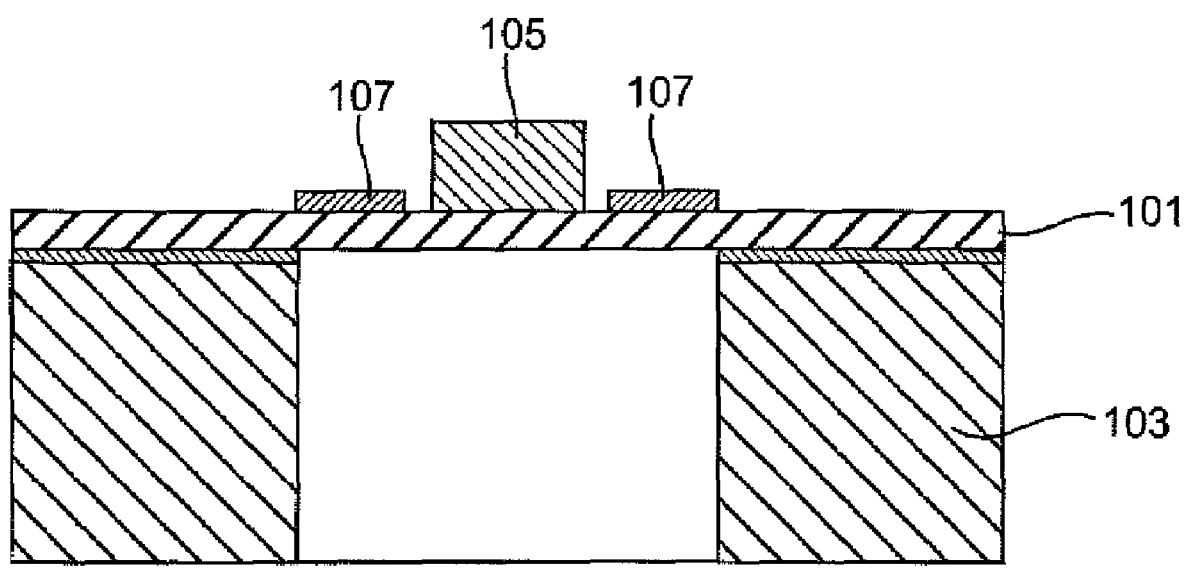
FIG. 13 provides a cross sectional view of one embodiment of the inventive pressure sensor device.

One embodiment of the inventive pressure sensor device is shown in FIG. 13, provided in cross section. A sensor membrane 101 is supported by a support substrate 103, where sensor membrane 101 contains a stress focusing boss 105, and pressure sensing elements 107. Pressure sensing elements 107 are typically resistors, particularly piezoresistors. The resistance of pressure sensing elements 107 is a function of the applied stress. As pressure is applied to sensor membrane 101, the membrane will deflect. The deflection of sensor membrane 101 produces stress in the sensor membrane 101, and as a result in the associated pressure sensing elements 107. The stress on pressure sensing elements 107 cause electrical resistance changes in pressure sensing elements 107, resulting in a measurable electrical signal related to the level of applied stress.

As an adjunct to the above teaching, in a representative embodiment of the present invention, both support substrate 103 and sensor membrane 101 are made of single crystal silicon. The pressure sensing elements 107 may be made of a stable gauge material, particularly a highly stable, e.g., a platinum comprising material, such as pure platinum or an alloy thereof; nickel chromium or alloys thereof; and the like. Alternatively, the pressure sensing elements 107 can be made of poly-crystalline silicon or similar materials.

In certain embodiments, the pressure sensor elements, e.g., platinum comprising piezoresistors, have a passivating layer disposed on the surface thereof. The passivating layer may range in thickness from about 50 to about 100 nm, and may be of any convenient material, e.g., silicon nitride.

Stress focusing boss 105 can be effectively constructed from a number of materials. However, preferably the materials for stress focusing boss 105 is utilized that have a low stress and a similar thermal expansion coefficient to the materials employed in sensor membrane 101. Ideally, materials for stress focusing boss 105 are selected from silicon nitride, poly-crystalline silicon, or amorphous silicon. These materials can be deposited by any number of standard semi conductor application methods discussed in more detail below.

Neutral Plane Embodiments

In certain embodiments, the compliant member, and therefore sensor elements associated with a surface thereof, of the subject devices are positioned at least proximal to, i.e., at or near, the neutral plane of the pressure sensor structure or chip. In other words, embodiments of the present invention provide a sensor design in which the membrane in the pressure sensor structure is situated in, adjacent to, through, or near the neutral plane of the structure in which the compliant member is present. Once so designed, if the total pressure sensor structure, e.g., chip, experiences bending stress, the compliant member will not be distorted by that stress. The result of the inventive design is that the sensor element within the pressure sensor does not respond to background stress, or responds only in an attenuated manner. Even partial adherence to the present inventive teaching can mitigate response to background stress at a level which substantially limits background pressure readings. If a particular inventive design calls for positioning that is not directly within the neutral plane, but none the less adjacent to or intersecting the plane, the distortion will be substantially ameliorated. The present inventive design and fabrication method thus provides a sensor with unprecedented stability.

The consideration of the neutral plane has previously been usefully applied in the engineering design of large, generally monolithic, objects such as solid beams and airplane wings. However, the invention of these particular embodiments unexpectedly and innovatively applies the basic principle of the neutral plane to the unique environment of micromachined pressure sensor chips. This represents a sharp divergence from the prior application of the neutral plane guidelines to engineering designs, as micromachined pressure sensors have the challenge of extremely small dimensions and often complex shapes, structures, and heterogeneous materials.

The inventive approach of specifically positioning a compliant member and associated sensor element within the body of a pressure sensor chip in order to provide greater stability represents a sharp deviation from present fabrication techniques. For instance, it is currently standard practice to produce sensing devices with the sensing element situated on the outside surface of the larger sensing structure. While this standard fabrication method provides simplicity of construction, it positions the sensing element at the most extreme position possible from the neutral plane. The prior microsensor designs thus are at the most exaggerated vulnerability to external forces. Thus, the teaching of the present invention results in sensor designs which are unique in the present art.

While unexpected in application to small, irregularly shaped devices as in the present invention, the basic understanding of the neutral plane in other applications has been well established. The neutral plane is sometimes described as the "neutral axis" plane. Descriptions and reviews of the neutral plane of objects, such as beams, is well known in the art. See e.g., McMahon & Graham, "The Bicycle & The Walkman," Merion (1992). See also the website having an address made up by place "http://" before "darkwing.uoregon.edu/~struct/courseware/461/461_lectures/461_lecture38/461_lecture38.html". As such, the concept of a structure's neutral plane is well known to those of skill in the art. The neutral plane concept is further described in priority U.S. Provisional Patent Application Ser. No. 60/615,117 filed Sep. 30, 2004; the disclosure of which is herein incorporated by reference.

Briefly, mechanical structures subject to bending stress have within them a theoretical plane that experiences pure bending. Other sections of this body will exhibit compression or tension in response to the bending stress. By example, typically the material above the neutral plane will experience tension if the bending stress is exerted in an upward direction. Conversely, the material below the neutral plane will typically experience compression. However, materials in that neutral plane of the body will theoretically enjoy an absence of tension or compression. In actual practice, due to the practical multidimensional nature of secondary forces, there can be some stresses in some areas of the "neutral plane". However, these stresses are much diminished relative to the other areas of the object.

Classically, for simple homogeneous solids, the neutral plane can be calculated from methods well know to the ordinary skilled engineer for a square chip of uniform thickness and uniform material. In this case the neutral plane is at the geometric center of the object. For more complicated geometries, the neutral plane can, in some cases, be calculated from standard formulas.

While the present application uses the term "neutral plane" in the present application to denote the geometric area most appropriate for the sensor element, the term in the present context has considerably broader meaning than that provided in the prior art. For instance, as applied to complex, heterogeneous shapes, the "neutral plane" may not, in fact, be a solid plane extending through the object. In the present context, the "neutral plane" can be ovoid, convex, concave, a limited internal rectangular shape, or any other shape which is calculated for a particular solid. It may also be discontinuous, or have voids within an area otherwise appropriate for the positioning of the sensor element.

Further regarding the term, "neutral plane", for the purposes of the present invention, this area may, in fact, be three-dimensional. Again, through modeling of a complex shape, which can include heterogeneous materials, the "neutral plane" could be spherical, conical, pyramidal, and again may be discontinuous or include voids within the areas appropriate for the position of the sensor element.

It is possible to determine a neutral plane for sensor structures of a number of arbitrary geometry by performing finite element analysis on the structure subjected to a bending load. Because of the complexity of the calculations, this step will be effectively accomplished through computer simulation. The practitioner will then be able to observe the location of a plane in which the longitudinal stress is substantially diminished, or ideally zero.

In the case of medical devices, there are often secondary stresses produce in more than a single plane. This can complicate the prior art stress calculation methods considerably, approaching the point where these multidimensional forces cannot be accurately accounted for. However, using the teaching of the present invention, these multidirectional complicating forces can be resolved into a three-dimensional zone where there is relative quiet for secondary stress forces. The present invention uses currently available computer modeling programs as above to provide for these otherwise impractical to solve calculations.

With the complete understanding of the mechanical stress dynamics on a pressure sensor device provided by the present invention, design approaches will become apparent to the ordinary skilled practitioner to maximize the stability of the device. For instance, some portions of the device can be built up with bulk materials to shift the neutral plane in a way that enhances the structure for fabrication purposes, or to provide advantageous alignment with other components in a larger device with multiple sensor. In some cases, it may still be useful to attach the sensor with flexible material to an underlying support structure in order to maintain the internally consistent neutral plan configuration of the smaller module. In other cases, in may be useful to rigidly attach the sensor to a larger bulk material to shift the plane preferentially. This optimization will in some cases lead to the identification of a neutral plane which is off-centered in the sensor body.

A particularly advantageous inventive design in the case of medical devices is a sensing module so carefully attuned by the teaching of the present invention that it can accurately provide pressure sensing without the necessity of a substantial housing. This innovative advancement provides great potential for multiplexing of sensors. The potential for such multiplexed devices represents a long felt need in medical devices, especially in the cardiac arena.

The determination of the "neutral plane" for arbitrary geometries is a considerably more complex calculation than the classic examples described above. However, using the inventive concept, a practitioner will be able to employ currently available modeling software to identify the neutral plane. In the examples below, typically micromachined structures take the form of a rectangular solid that may have perforations within its structure. Equally challenging to the classic approach to neutral plane determination, these devices are typically constructed of diverse material.

Guided by the teachings of the present invention, the neutral plane can be determined from finite element simulation using finite elements software packages such as ANAYA, Inc. or Cosmos, Structural Research and Analysis Corporation.

To find the neutral plane using finite element modeling software, one approach which can be used by the practitioner is the following:

1) construct a solid model of the pressure sensor chip,
2) apply boundary conditions to constrain certain portions of the chip and apply a load such as a force, pressure or torque to a second portion of the chip,
3) mesh the model,
4) solve the model,
5) examine the resulting plot of strain within the chip to determine the position that has minimum in-plane stress.

Typically the model is run multiple times while varying a specific design parameter with each run. In this way one can determine the effect of the design parameter on the neutral plane position.

The present invention allows for the practical design and construction of pressure sensors, even at the tight size limitations such as cardiac, ocular and neurological applications. The inventive designs are particularly applicable in testing environments with heightened pressure distortion challenges, such as with cardiac and bone sensing applications.

The present invention allows for the construction of pressure sensing devices that are from about 0.01 to 10.0 mm in size, such as about 0.1 to 5.0 mm in size, and including about 0.3 to 1.5 mm in size. Additionally, the present invention further allows the construction of pressure sensing devices of considerable thinness, that is from about 0.01 to 4 mm in depth, such as about 0.1 to 2.0 mm in depth, and including about 0.2 to 1.0 mm in depth.

In representative embodiments, in pressure sensing devices which are constructed as directed by the present invention, there will be a central cylindrical area housing the sensing membrane which is either void or contains a material dissimilar from the surrounding supporting material, such as a flexible silicone material. This central area can be from about 0.1%-10% of the overall volume of the sensor device, such as from about 0.5%-5%, and including from about 1%-3%.

Figure 14A:
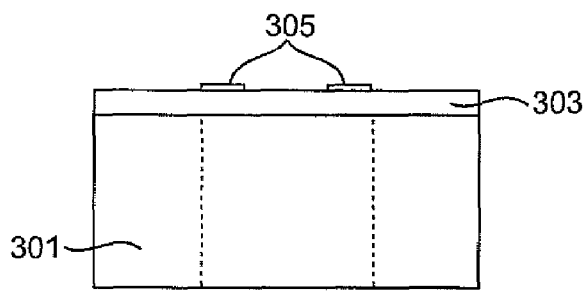
FIGS. 14 A & B provide cross sectional and planar views of a prior art pressure sensor.
Figure 14B:
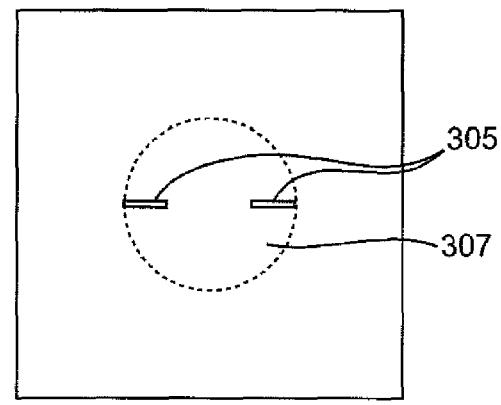

FIG. 14A provides a cross-section of a micromachined pressure sensor of the prior art showing sensor chip 301, sensor diaphragm 303 and pressure sensitive elements 305 which are provide on sensor diaphragm 303. The pressure sensor elements 305 in this prior art example will typically be piezoresistors, as described above. However, the resisters can also be other pressure and/or strain measuring elements or transducers. One example of such alternative strain measuring elements in this context are vibrating members whose vibrational frequency would change with strain exerted upon them. FIG. 14B provides a planar view of the prior art pressure sensing device shown in FIG. 14A. Note that the area 307 which is the area of the sensor diaphragm which is actively engaged in sensing, is fully circular in this view. While the area provided in this graphic representation is provided as circular for the purposes of demonstration, it will be appreciated that in practice, its area could be oval, square, rectangular, or other shapes.

Figure 15A:
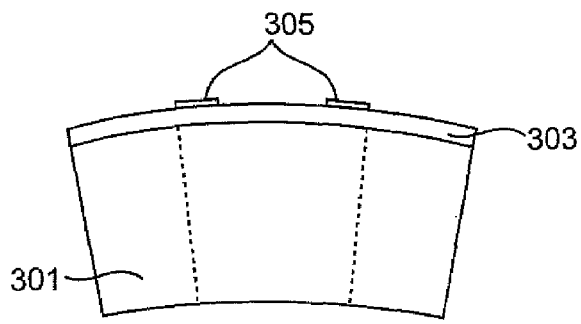
FIGS. 15A & B provide cross sectional and planar views of a prior art pressure sensor experiencing a bending stress.

FIG. 15A provides a cross sectional view of the prior art device in FIGS. 14 A & B experiencing a bending stress away from sensor diaphragm 303. In this case, the sensor chip 301 is now bent. As can be seen in this view, sensor elements 305 would be stretched when the sensor chip 301 experiences flexion stresses in this manner. As shown in the top view, FIG. 15B, the effect is to distort the area 307 from a circular an ovoid shape. This force acts on the sensor elements 305 in a manner which serves to distort the elements by elongation.

Figure 15B:
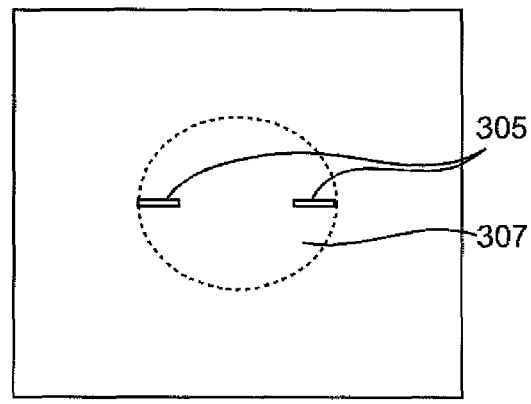
Figure 16A:
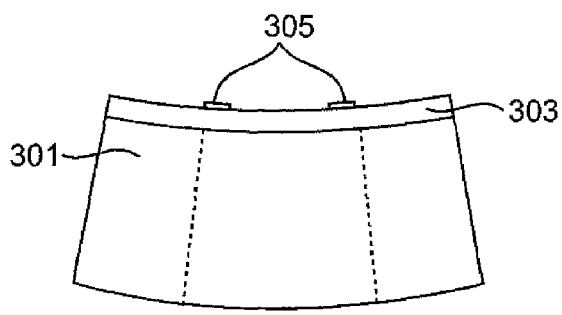
FIGS. 16A & B provide cross sectional and planar views of a prior art pressure sensor experiencing an opposite bending stress.
Figure 16B:
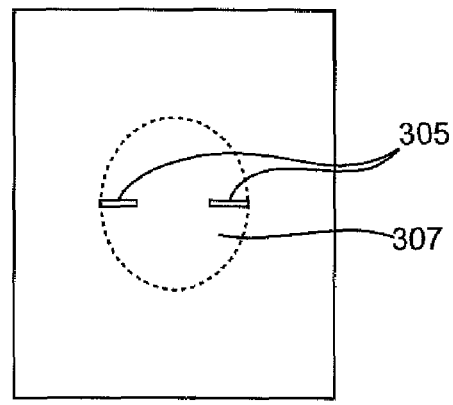

Conversely, in FIG. 16A an opposite bending stress from that seen in FIGS. 15 A & B is applied to sensor chip, that is away from sensor diaphragm 303. As shown in the top view, FIG. 16B, the compressing force on the surface of the chip causes the area 307 to distort into an ovoid shape, in this case with an axis in the opposite direction from that of area 307 shown in FIG. 15B. The result is that sensor elements 305 are subject to a compression distortion. These views are provided in exaggerated dimensions as compared to actual devices in order to more clearly demonstrate the effect of the stress, and are diagrammatical in nature.

In both the case of a bending stress away from the sensor diaphragm 303 shown in FIGS. 15 A & B and the bending stress away from the sensor diaphragm 303 shown in FIGS. 16 A & B, the sensor output from the pressure sensor 301 would change due to the spanning stress, introducing background readings which could distort or fully obscure the pressure information which the device is meant to assess. This signal distortion is due to the change in the length of the sensor elements 305 caused by the bending of sensor chip 301.

FIGS. 17A & B provide a view of one embodiment of the present invention that is a sensor device with the sensor element located at or near the neutral plane of the device. FIG. 17A provides a cross section and FIG. 17B a plan view of the same device. In this embodiment of the invention, a first sensor chip 309 is provided, with a sensor membrane 311 on its upward surface. Sensor elements 313 are provided on the sensor membrane 311.

In distinction to the prior art examples shown in the prior figures, the inventive embodiment shown in FIGS. 17A & B provides an additional, physical continuation of the sensor chip 309 in the form of a second sensor chip 315. In this case, and distinct from prior art sensors, the thicknesses of first sensor chip 309 and second sensor chip 315 are chosen so that sensor membrane 311 is in or near the neutral plane of the composite chip. A similarly advantageous design can be achieved with different physical dimensions, if there are accommodating material differences in the separate elements of the design. Area 317 is the area of the sensor diaphragm which is actively engaged in sensing, and is essentially circular in this view.

FIGS. 18 A & B show the device provided in FIGS. 17A & B experiencing a bending stress in a direction away from sensor diaphragm 311. As is apparent from this view, the bottom surface 319 of sensor chip 309 is experiencing compression while the top surface 321, of sensor chip 309, is experiencing tension. Yet because the sensor membrane 311 is at the neutral axis, it does not experiencing tension or compression as a result of these external forces. Therefore, sensor elements 313 do not change in length. Because, as distinct from the prior art example above, there is no change in length of sensor elements 313, there would also be no change in sensor output due to the straining stress. Note that area 317 remains circular, as contrasted with the prior art constructs shown above.

FIGS. 19A & B are planar and cross section views of the inventive device shown in FIGS. 17A & B and with a stress of the opposite magnitude applied to the chip from that in FIGS. 18A & B. Note the same principles applied to the effect on the sensor elements 313 that is that they do not suffer from distortion. The area 317 again remains circular.

Figure 20A:
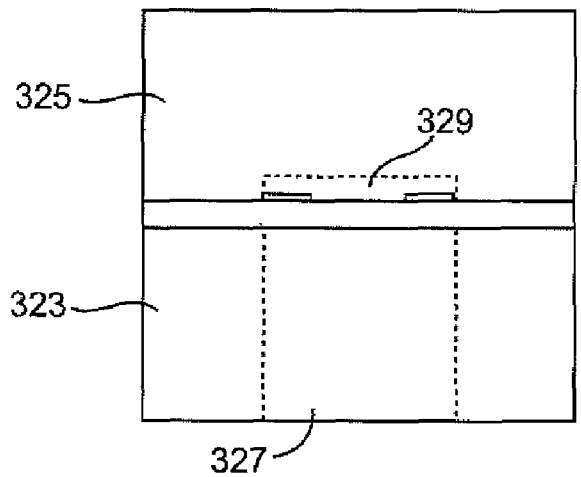
FIGS. 20A & B provide cross sectional and planar views of yet another representative embodiment of the present invention.
Figure 20B:
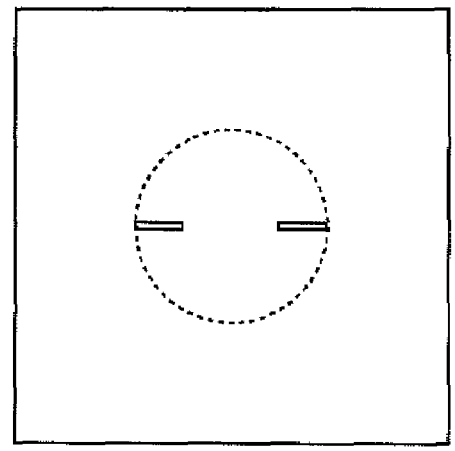

FIGS. 20A & B show cross section and plan views, respectively, of an additional embodiment of the inventive sensor design. In this case, bottom sensor chip 323 is matched with a top sensor chip 325. Top sensor chip 325 is provided with a cavity 329 which is etched into top sensor chip 325. Bottom sensor chip 323 is provided with a through-hole 327 etched through sensor chip 323.

In this case, the pressure sensor measures the difference in the pressure applied to the through-hole 327, the difference between pressure in the through-hole 327 and the cavity 329. The cavity 329 can optionally be filled with ambient air or a gas at ambient pressure. In these variants on this embodiment, sensor would be categorized as a gauge pressure sensor. Alternatively, the cavity 329 can be filled with a vacuum. In that case, the pressure sensor would be categorized as an absolute pressure sensor.

Figure 21A:
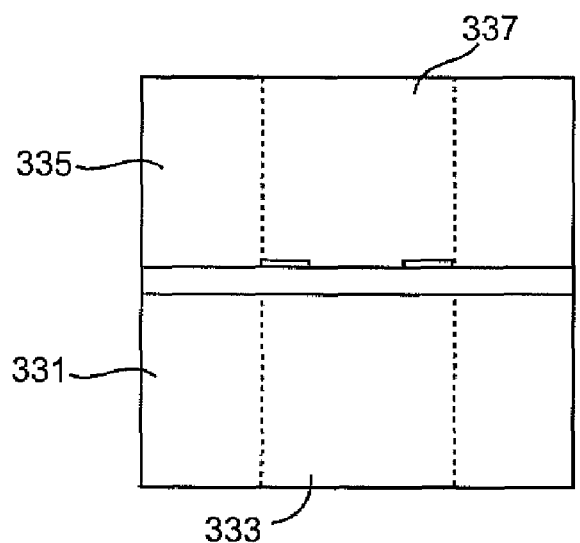
FIGS. 21A & B provide cross sectional and planar views of yet another representative embodiment of the present invention.
Figure 21B:
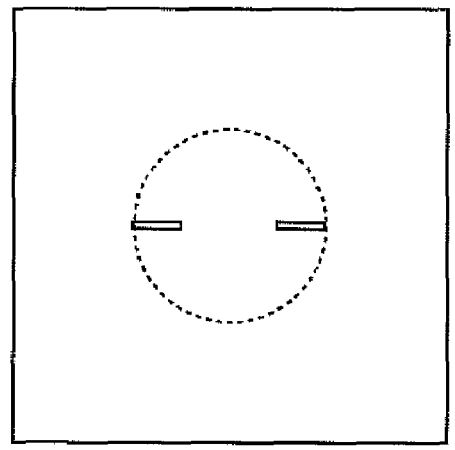

FIGS. 21 A & B provide a cross sectional and planar view of a third embodiment of the present invention. In this case, bottom pressure sensor chip 331 is provided with a bottom through-hole 333. Upper pressure sensor chip 335 is provided with an upper through-hole 337. In this embodiment, the inventive pressure sensor responds to the difference in pressure between the bottom through-hole 333 and the upper through-hole 337, which can be connected to different pressure sources. In this configuration, this inventive embodiment would be categorized as a differential pressure sensor.

Amplified Compliant Force Embodiments

In certain embodiments, the subject sensor structures are characterized by having a transducer element separated from a surface of the compliant member on which it is associated, i.e., mounted, by a spacer or beam element, also referred to herein as a lever. Optimizing compliant force through the use of beam elements in the pressure sensor design according to these embodiments provides, for the first time, pressure sensor devices of unprecedented small dimensions and robust character while achieving uniquely fine sensitivity levels.

The sensors of these embodiments provide an unprecedented increase in signal output for pressure sensors for a given amount of pressure. In this way, these embodiments provide sensing devices which, while constrained in size, are able to provide highly accurate pressure readings at very small changes in pressure. The force amplification achieved with devices of these embodiments increases the capacity for sensitivity of micromachined pressure sensors by about 1-1,000 times, such as about 50-500 times, and including about 150-250 times (see FIG. 25), as compared to sensitivities achieved with analogous devices in which the beam element(s) is not present. When combined with other, standard sensitivity design modifications, these sensitivities can reach even higher levels.

The present inventive devices and design methods provide the sensor design engineer a tool by which the apparent strain on the sensor membrane can be magnified or amplified. This tool allows a given membrane deflection due to a pressure difference to be dramatically amplified. With the inventive approach of employing a beam element, the strain-measuring elements will experience a larger strain without distortion. As a result, the electrical sensor signal generated by the sensor will be correspondingly increased.

Sensors of these embodiments provide for the detection of smaller and smaller differences in pressure. The present embodiments allow the detection of pressures in the range of about 0.01 to 100,000 mmHg, such as about 0.1 to 10,000 mmHg, and including about 1 to 1000 mmHg.

For a given plate bending, it is possible to calculate the position of the where the center of the curvature. It is also possible to calculate the radius of the curvature of the plate bending. From mechanical texts and from standard engineering analysis, the practitioner will be able to locate the strain at any given location within the membrane. This strain is typically equal to the distance of that point from the neutral plane of membrane divided by the radius of curvature.

The beam dimensions in the present invention can range from about 1-1,000 μm, such as from about 5-500 μm, and including from about 10-100 μm.

Additionally, in the present invention, multiple inventive beams can be used on a sensor membrane, for instance from about 1-100 beams, such as from about 3-50 beams, and including from about 4-5 beams.

Figure 22:
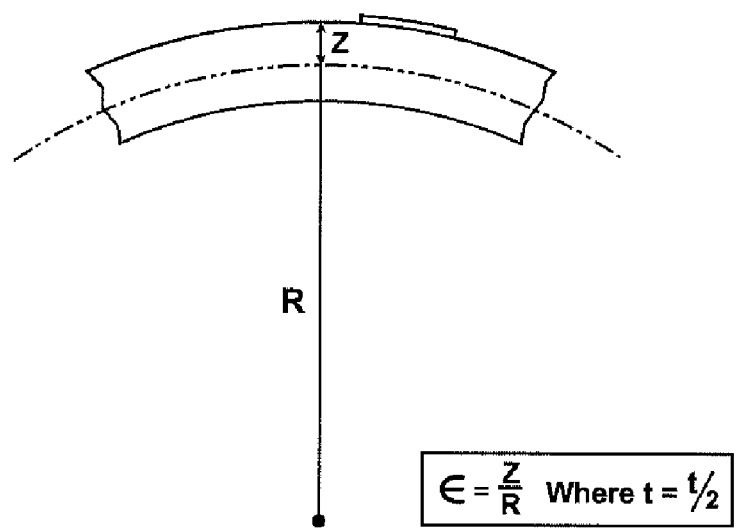
FIG. 22 provides a cross sectional view of a prior art pressure sensing device.

The sensors of these embodiments can readily be designed to be able to optimize the structure to achieve as small an arc as is practically possible in order to achieve optimal results. By applying bosses to the sensor membrane and changing the membrane dimensions to reduce to radius of curvature, one must consider that a larger strain will result FIG. 22 provides a cross-sectional view of a segment of a membrane or plate undergoing a deflection. This diagrammatical representation is of a section of pressure-sensing membrane that is experiencing a pressure difference, causing it to bow. From the discussion above, the formula which will be employed by the practitioner in practice of the present invention will effect the prior art device of FIG. 22 in the following manner. The largest strains will be when z is the largest. However, since the strain element has to be connected to the plate, the greatest possible z occurs at one or the other surface of the plate.

In FIG. 22 it can be observed from the top surface of the membrane in the example shown is equal to the thickness divided by 2. On the bottom surface, z is equal to the negative of the thickness divided by 2. This puts a limitation on the maximum strain that the sensor element can experience for a given radius of bending.

Figure 23:
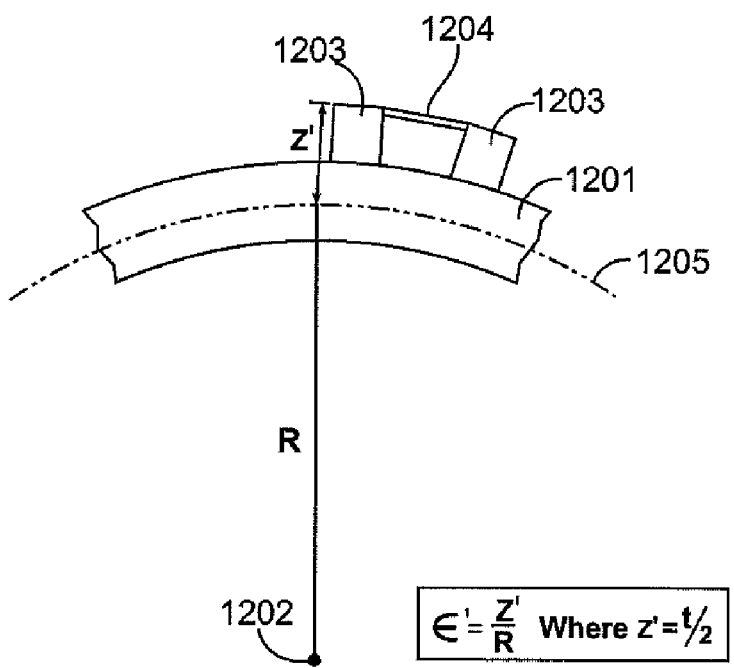
FIG. 23 provides a cross sectional view of an embodiment of the present invention.

FIG. 23 shows the effect of the inventive design which serves to displace the strain-measuring elements from the membrane as shown. The section 1201 of the pressure-sensing diaphragm is shown in this view bending about the center of radius 1202. Offset elements, (also referred to herein as spacers or beams) 1203 are provided which serve to displace strain-measuring element 1204 from the surface of the membrane.

From this depiction, one can observe that z-prime, the distance of strain-measuring element 1204 from the neutral axis 1205, is larger than the thickness divided by 2. In fact, as practiced in the present invention, z-prime can be any arbitrary value. As will be understood by the practitioner, z-prime may in some cases be limited by some practical considerations such as fabrication techniques.

Figure 24:
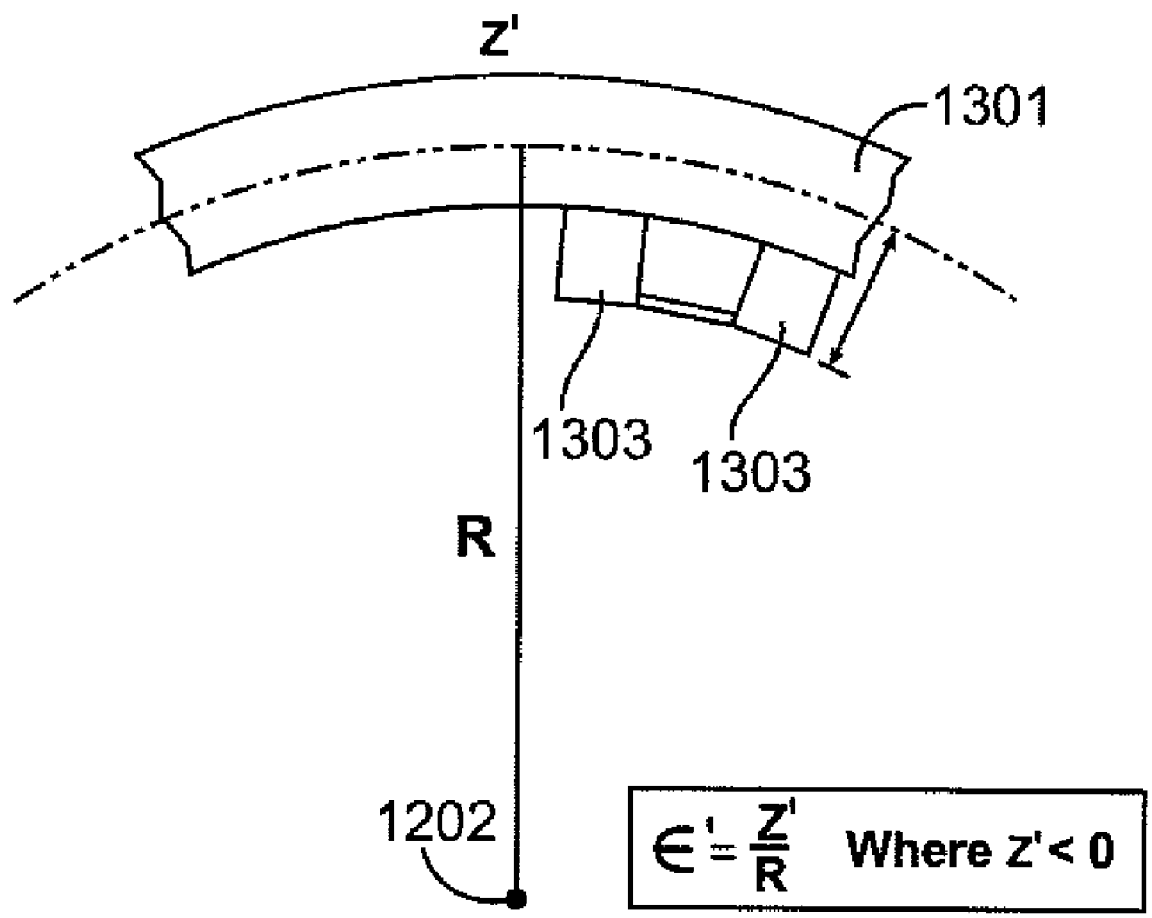
FIG. 24 provides a cross sectional view of an alternate embodiment of the present invention.

FIG. 24 provides an example of an alternate embodiment of the present invention. This figures shows offset elements 1303 placed on either side of membrane 1301. In this case, because the offset is below the membrane, the z-prime has a negative value. However, this effect does not affect the engineering principle shown in this case.

In a specific embodiment of the present invention, if one were to take a pressure-sensing membrane with typical dimensions of a thickness of 1.5 μm and in the prior art, the maximum z would be half of that, or 0.75 μm. If these standoff elements were manufactured using an additional 1.5 μm, the z-prime would now be 1.5+0.75, or 2.25 μm. This engineering modification can be accomplished simply and with ease using known fabrication techniques.

Using the above inventive engineering advances, the inventive devices of these embodiments have effectively increased the sensitivity of the prior art pressure sensor design as illustrated in FIG. 22 by 3-fold. This provides a simple exemplification of the present invention. However, using the present inventive techniques, amplification values of up to 10 or more times can be easily achieved. Thus, the present invention increases sensitivity by about 1-100 times, such as about 10-80 times, and including about 20-40 times, e.g., as compared to prior art devices, such as those reviewed in FIGS. 1 to 1B.

Practical considerations limit the amplification factor using this simpler embodiment of the inventive technique to amplifications of about 10. However, as shown in FIG. 25, by extending the inventive concept further, in a more advanced, sophisticated embodiment using in-plane amplification, much larger amplification ratios of the strain are possible. In this case, 100 or several hundred fold increase is available using the present inventive approaches.

Figure 25A:
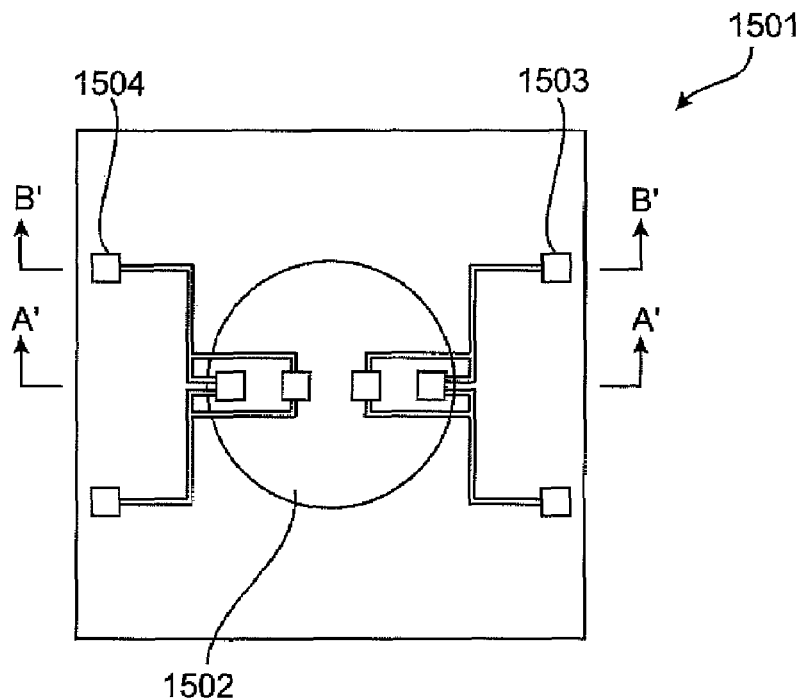
FIGS. 25A to C provide a view of an inventive in-plane and mechanical amplification.
Figure 25B:
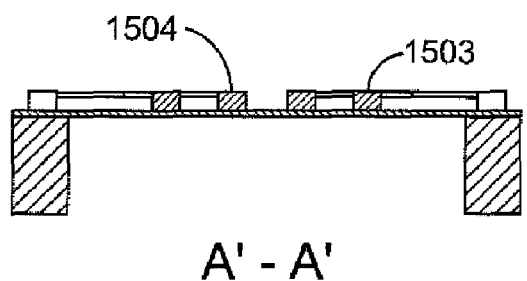
Figure 25C:
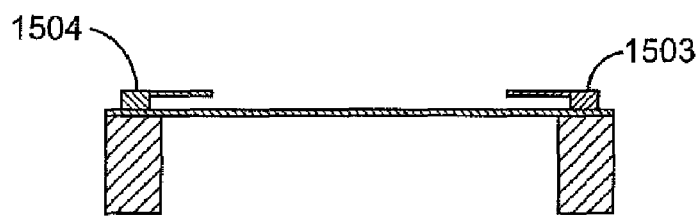

FIG. 25a provides a planar view of pressure sensor chip 1501, with a pressure sensor membrane 1502. Amplifying structures 1503 and 1504 are deposited on the pressure sensor chip surface. FIGS. 25B and 25C provide cross-sections through this device at different locations marked by the A and A-prime and B and B-prime. As shown in FIGS. 25A, 25B and 25C, the force-amplifying structures contact the surface of the chip in some locations but do not contact it in others, that is are freestanding above the surface in those locations.

Figure 26:
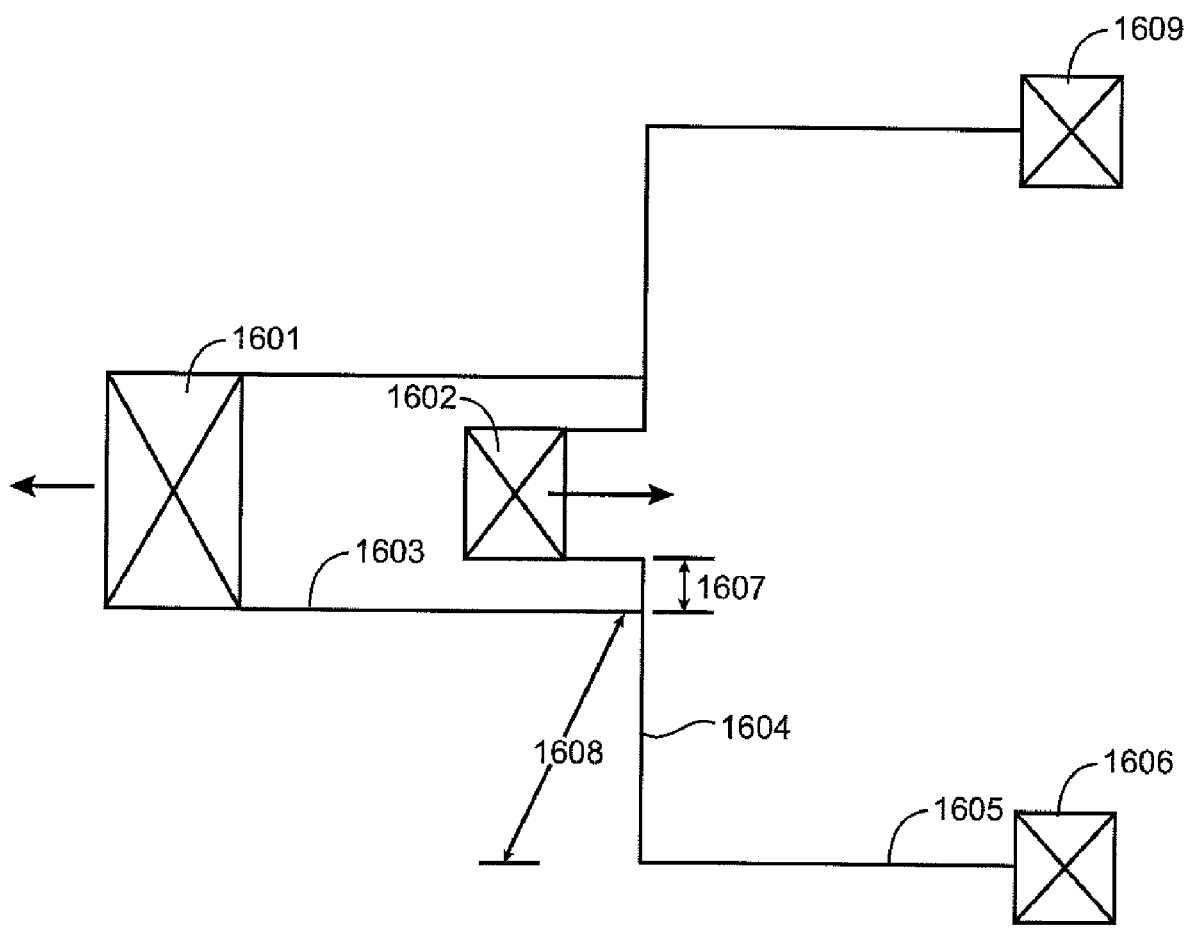
FIG. 26 provides a diagrammatic view of one embodiment of the present invention.

An example of an inventive force amplification structure is provided in additional detail in FIG. 26. Pad 1601 is at a location that is attached to one part of the pressure sensor membrane and pad 1602 is attached to a second part of the pressure sensor membrane. Using the method of the present invention, these locations will be chosen such that there are locations that experience a large displacement when membrane deflects due to an applied pressure.

Using the example of beam 1603, if location 1601 were to move away from location 1602 when a positive pressure was applied, beam 1603 would get pulled toward pad 1601. This movement would cause a rotation of beam 1604 whose one end is anchored to pad 1602. However, a mid-point is attached to beam 1603. That rotation would cause a tension on beam 1605 which is then attached to a fixed pad 1606. Fixed pad 1606 is attached to some portion of the chip that would not move. This stationary portion of the chip can be, by example, in the periphery of the membrane.

Beam 1604 is provided with a segment 1607. Comparing the length of segment 1607 to the length of the segment 1608, if these lengths are unequal, it will result in either magnification or a reduction in the amplitude of the relative motion of pad 1601 or pad 1602. For instance, if segment 1607 were 10 μm long and segment 608 were 100 μm long, then the end of beam 1604 would move 10 times as much as the displacement between pad 1601 and pad 1602. This inventive design provides a 10-fold multiplication in the amplitude of the motion.

This improvement translates to a 10-fold increase in the strain in beam 1605 and a 10-fold increase in the electrical output of the sensor for a given amount of pressure.

As an example, this particular structure is provided with a mirrored structure. As such, pad 1606 has its mirror image in pad 1609. This inventive design is a convenient approach to fabrication. It also meets standards of good mechanical practice by providing symmetry. This inventive embodiment has the additional advantage that if, for instance, a strain measuring element 1605, was a piezoresistor, the resistance between pad 1606 and pad 1609 can be measured. By observing the change in the resistance, a measure of the strain is provide in those elements, and hence a measure of the pressure.

The above description provides one example of using the inventive lever principle to amplify the force. It will be appreciated by the ordinary skilled artisan that there are many variations on a lever. Equally, how to make levers has been provided in at a previously unavailable level of sophistication by computer methods for determining the optimum shape of levers for micromachined structures. In the prior art, such approaches have been applied to applications like accelerometers and to sort of the micromachined equivalent of a Pantograph. In the latter example, the motivation is to apply a large displacement and cause a very precise motion. Otherwise, the device is employing a force generator that has only a very small displacement which must be amplified.

Additional Features

In some embodiments, the sensor structures further include at least one conductive wire disposed between two layers of the substrate and coupled with the at least two transducers, e.g., piezoresistors, for transmitting sensed data from the sensor structure. For example, the conductive wire may be made of gold, platinum or the like. The layers of substrate may comprise any suitable material or combination of materials, such as a polyamide, a silicone and/or the like. In some embodiments, the at least one wire is operatively coupled with a multiplexed catheter via a conductive liquid or gel. Such multiplexed catheters are described in copending U.S. patent application Ser. Nos. 10/764,429; 10/764,127; 10/764,125; and 10/734,490; the disclosures of which are herein incorporated by reference.

The sensor structure may further comprise, at least one application-specific integrated circuit (ASIC) comprising an analog-to-digital converter for converting analog signals sensed by the resistors into digital signals. Alternatively, the sensor may include at least one ASIC comprising a voltage-controlled oscillator for converting analog signals sensed by the resistors into frequencies. In still other embodiments, the sensor may further include at least one ASIC comprising a voltage-controlled duty cycle oscillator for converting analog signals sensed by the resistors into duty cycles. In any of these embodiments, the ASIC may comprise a two-wire circuit, a three-wire circuit or a circuit having more or fewer wires.

One of the largest sources of stress and error on a tenth-of-a-millimeter scale pressure sensor is the gradual relaxation of stress induced by a wire bond. Therefore, some embodiments of the present invention eliminate wire bonding from the sensor, for example by using planar processes to fabricate a flexible lead in an integrated fashion. Thus, the electrical signals are brought to and from the chip via thin gold wires embedded between two flexible polyamide or silicone layers of the substrate. In a representative embodiment, these signals are then conducted to wires embedded in an associated catheter or lead via a thin layer of conductive liquid or gel. This process step introduces a variable resistance in the power, ground and signal lines.

Figure 27:
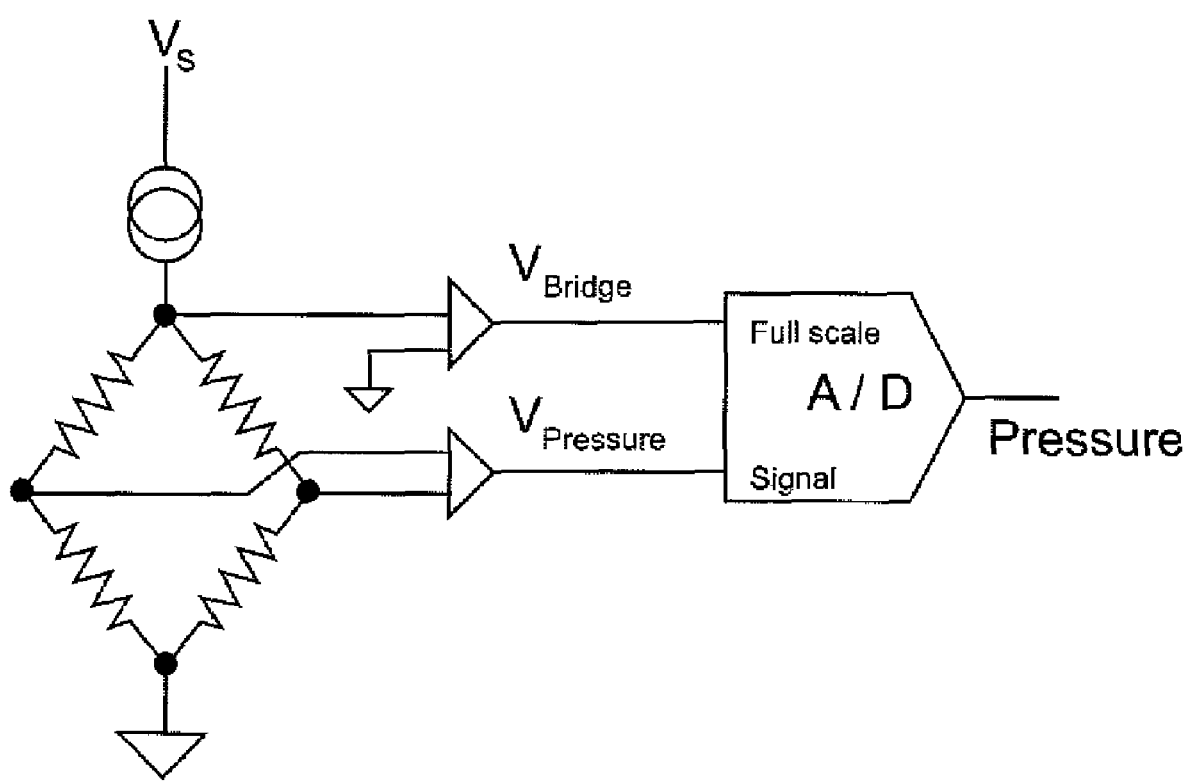
FIG. 27 is a circuit diagram of a basic pressure sensing circuit which may be used in various embodiments of the present invention.

In certain embodiments, a five-wire system as shown in FIG. 27 is employed to eliminate this variation. FIG. 27 is a representation of a simple integrated electronic device integrated alongside the inventive pressure sensor die. This configuration provides the capacity for the pressure sensor information to be transmitted back to the wire in a more robust fashion.

On the integrated circuit, shown above the Wheatstone bridge, is a current source. This current source can be of many well-known designs providing a stable amount of current into the resistor bridge. This configuration produces a voltage relative to ground at the top of the Wheatstone bridge, represented by the $V_{Bridge}$. Specifically, the output of the top of the Wheatstone bridge goes into an amplifier relative to ground producing a voltage called $V_{Bridge}$. In some instances, the output may be that potential. In other cases, it may be scaled by the amplifier, $V_{Bridge}$. $V_{Bridge}$ goes into the analog to digital converter A/D, into the full scale input of that. The analog to digital converter is a ratio-metric converter such that the input signal is ratioed to the full scale signals.

The mid-point to the bridge goes into an amplifier. The output is labeled $V_{Pressure}$. That is then put into the signal version of the analog to digital converter. In some cases, the $V_{Bridge}$ amplifier and the $V_{Pressure}$ amplifier are all integrated into the AD converter. In these embodiments, four lines go directly into the converter. One of the lines is the ground which represents the bottom of the bridge. The second line is the potential at the top of the Wheatstone bridge that would be the full scale. The two inputs would be the signal or the amplified version of the signal. If a differential signal is put in, there are two inputs put in. That would be the ratio metric A to D. The purpose of this configuration is to provide a high impedance signal that can be sent back to the "can."

Figure 28:
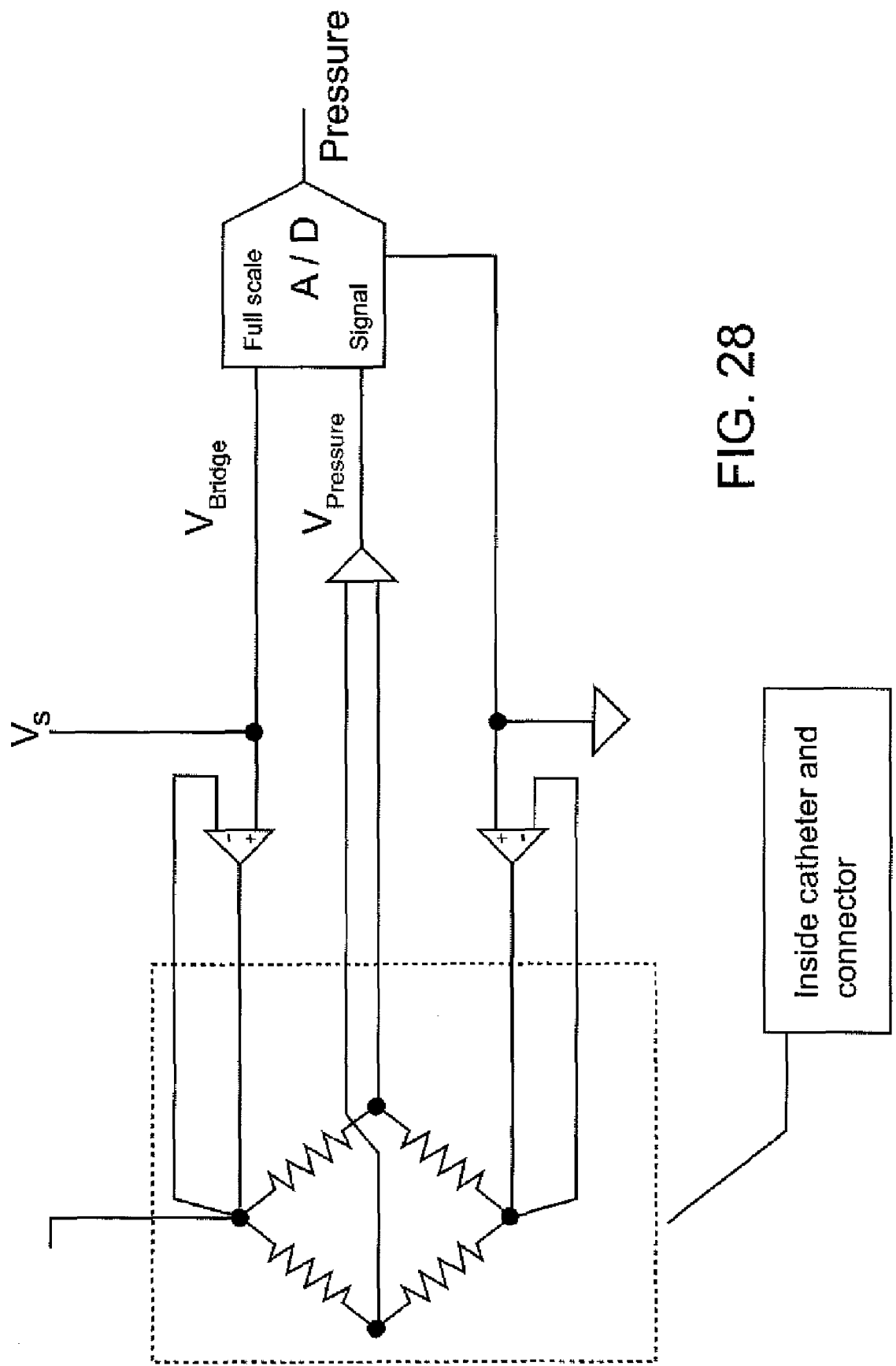
FIG. 28 is a circuit diagram of a six-wire circuit which may be used in various embodiments of the present invention.

A six-wire system shown in FIG. 28 may be used for a full bridge, in a similar manner. FIG. 28 provides a modified version of the above configuration. This configuration provides a system particularly appropriate for use if the pressure sensor is on a catheter, among other applications. In an embodiment where six wires go down the catheter and a Kelvin connection is used to drive the current through the Wheatstone bridge, a separate line is used to monitor the potential at the top and bottom of the Wheatstone bridge.

For these six wires, the potentials are then independent of the changes in impedance of those interconnecting wires. If the electronics are integrated onto the circuit, the above approach can also be used to reduce errors.

All of the above described systems can utilize either an AC or a DC current source. Modification of the electronics to accommodate an AC system are possible and are well known in the art for doing sampling with an AC vs. a DC system. The AC systems remove DC offsets that accrue during the amplification process.

Figure 29:
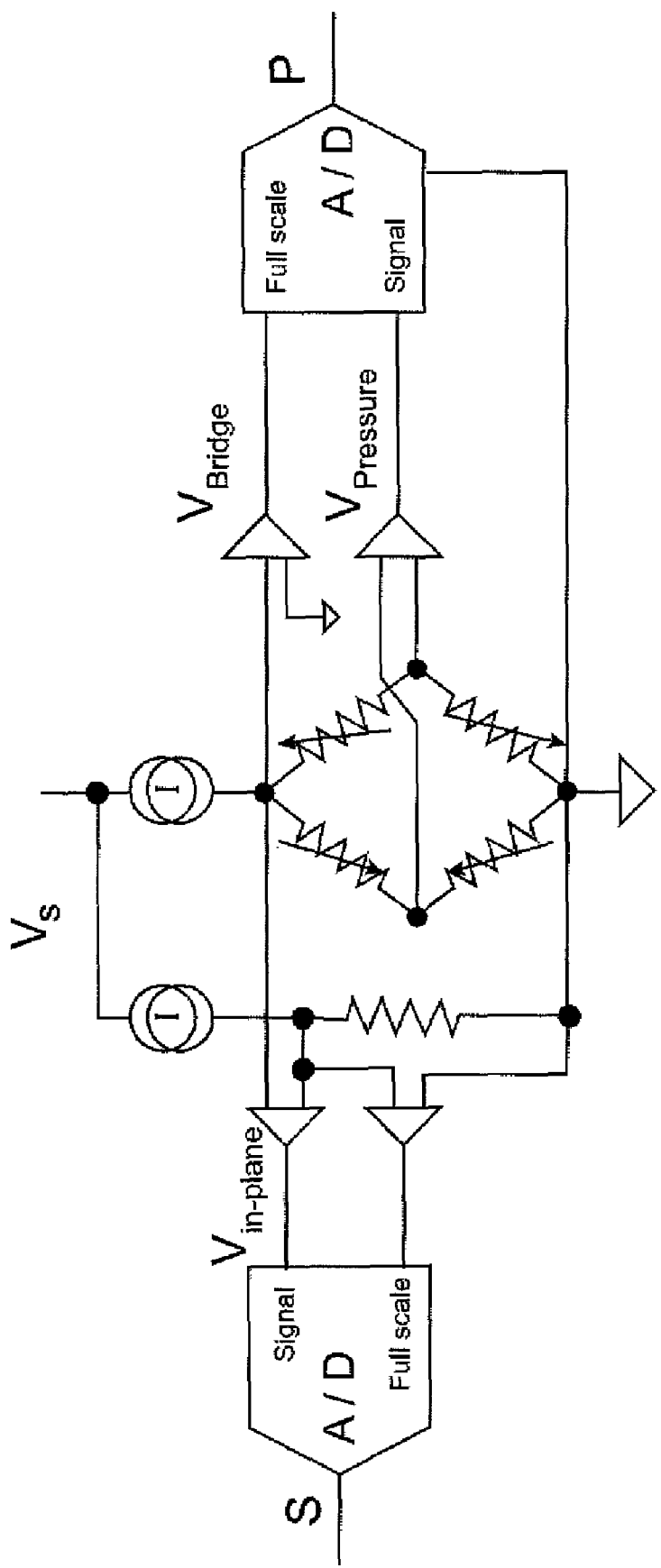
FIG. 29 is a circuit diagram of a compensating pressure sensing circuit which may be used in various embodiments of the present invention.

In one embodiment, the analog pressure signal is converted into either a frequency, or a duty cycle or a digital number before being transmitted over the variable resistance interface. A circuit as shown in FIG. 29 may be used in such an embodiment to convert the analog pressure signal into a single digital number that is then communicated to a computer connected to the catheter via two or three wire interface. FIG. 29 shows a system that compensates for the stretch of the wafer or the change in temperature of the chip. This compensation is accomplished by having a second resistor in parallel to the Wheatstone bridge driven by an identical current source. That goes into an A/D system producing a S parameter which represents the stress of the wafer changes the gauge and the gain of the Wheatstone bridge. This S parameter is in addition to the first version of the system described above which has just the pressure output.

Figure 30:
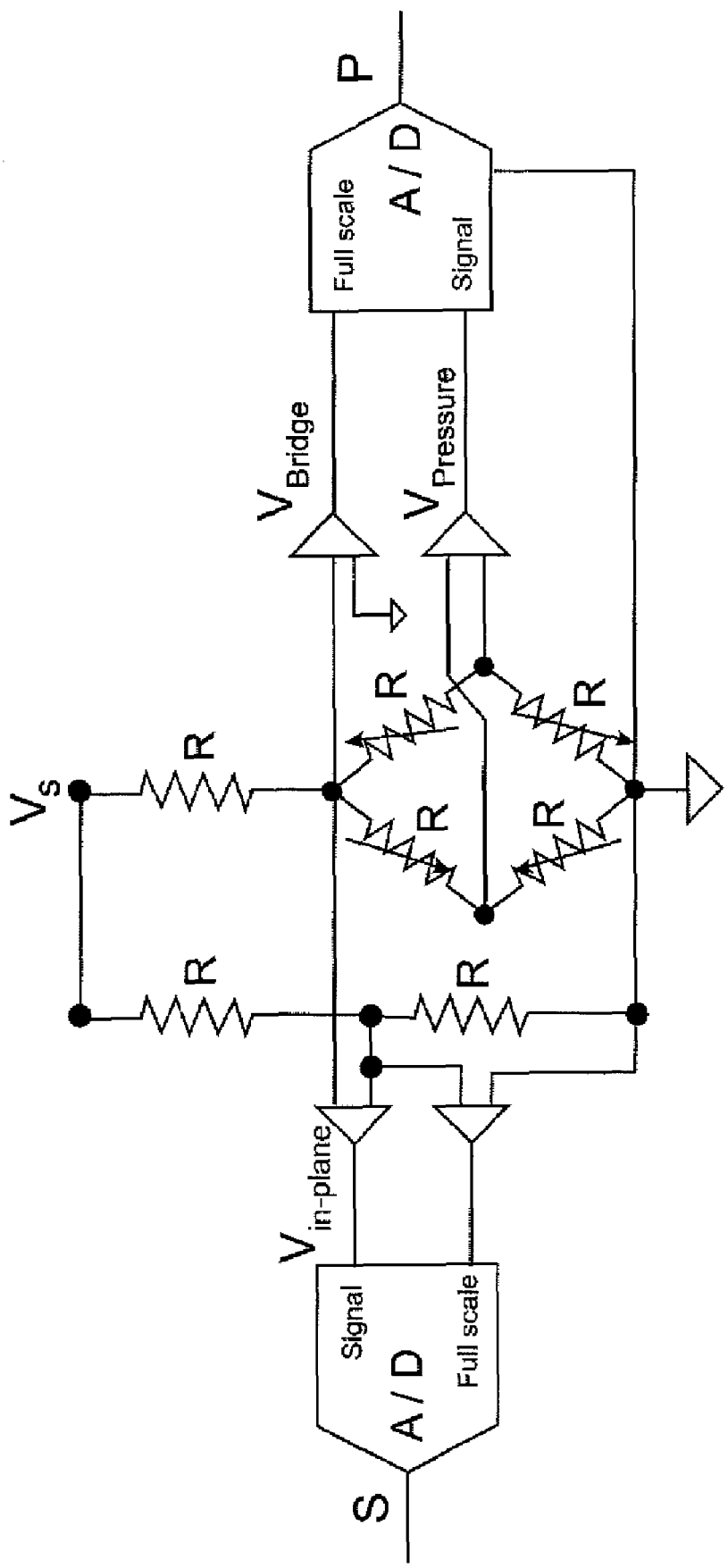
FIG. 30 is a circuit diagram of an alternative embodiment of a compensating pressure sensing circuit which may be used in various embodiments of the present invention.

Alternatively, a circuit as in FIG. 30 may be used to provide additional information by measuring the common-mode changes to the pressure-sensitive resistors caused by forces applied to the substrate, such as twisting, bending and/or stretching forces. A temperature sensor may also be added to the sensor to further correct for errors caused by temperature changes. FIG. 30 shows the resistors all connected to the one supply source and how there are two Wheatstone bridges together. The big Wheatstone bridge with the capital R's on the outside is for measuring the strain or the temperature of the overall system. The pressure sensor Wheatstone bridge is then used to measure pressure. The S output is then used to compensate the P output, which is the primary pressure indication.

In certain embodiments, these circuits are all integrated onto the same die as the pressure sensor. Alternatively, the circuits may be integrated onto a die which is operatively coupled, e.g., welded, to the pressure sensor die.

Figure 30A:
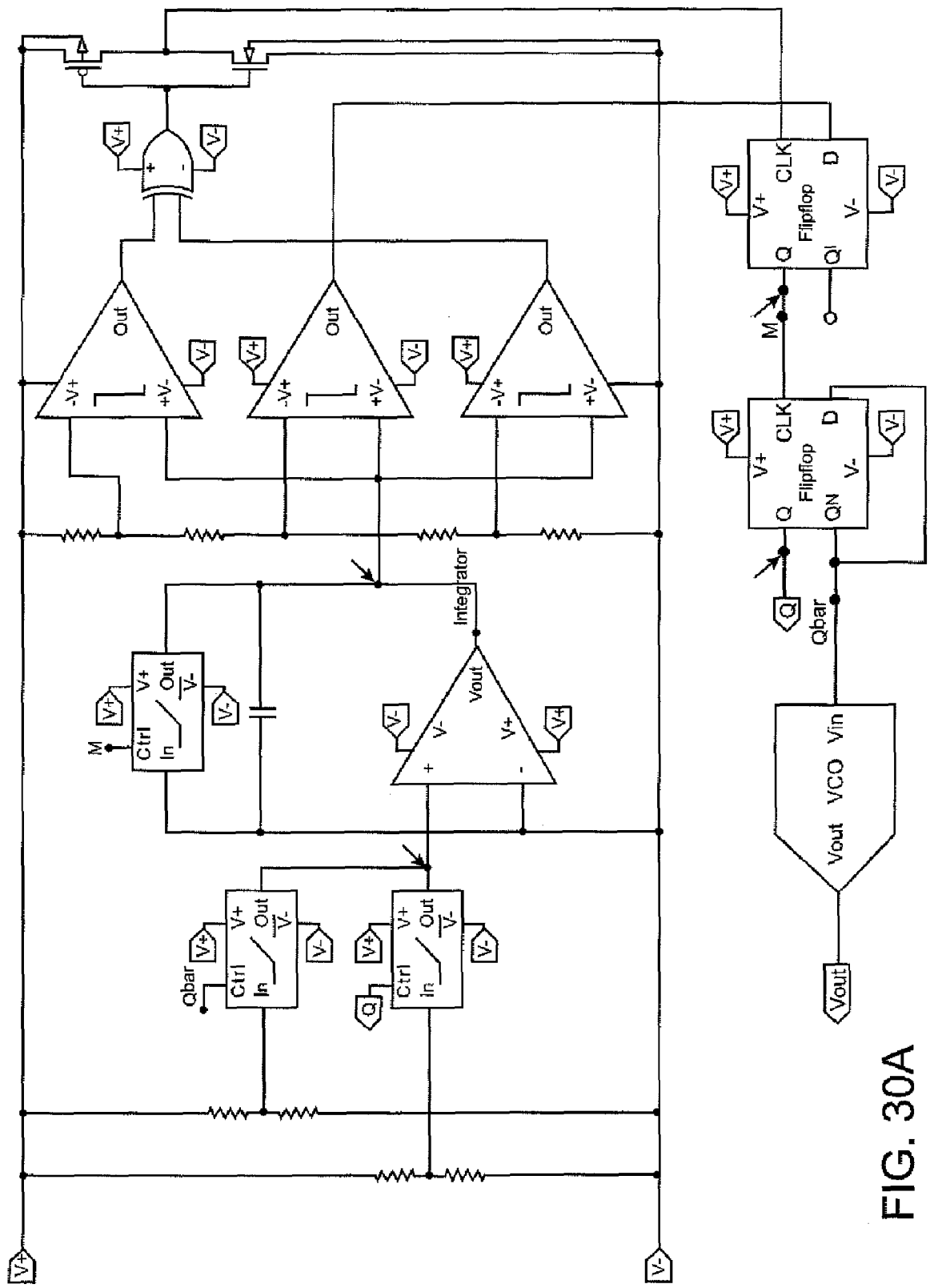
FIG. 30A is a circuit diagram of a VCDCO circuit which may be used in various embodiments of the present invention.

Referring now to FIG. 30A, multiple piezoresistors may broadcast data either during a predetermined interval or using a dedicated frequency. One embodiment may include, for example, a circuit including a voltage-controlled duty cycle oscillator that converts a differential pressure signal into an oscillator with a variable duty cycle, as shown in FIG. 30A. The output of such a circuit produces a series of pulses: the ratio of the "on" state to the "off" state is proportional to the absolute pressure. This series of pulses then becomes the envelope for a carrier frequency of a voltage controlled oscillator. Each of several sensors may broadcast at a different carrier frequency. An external monitor may have a number of electronic filters connected in parallel to the catheter's output line, with each filter tuned to one of the carrier frequencies. The output of each filter may, for example, comprise a series of square pulses whose duty cycle (the ratio of on time to off time) is proportional to the pressure measured by that sensor. As such, FIG. 30A shows a different type of a circuit that converts pressure into a more robust signal. Here the pressure sensor resistors are the four resistors on the left that go up and down with pressure. The two outputs of those four resistors go into analog switches that alternatively go up or down into the same set of sample electronics. Depending on the state of the sample electronics, each output goes into an integrating capacitor which is C int. When the potential of C int reaches a threshold, it fires off a logic circuit that resets the integrator and then starts it over again with the other potential driving it up and down. The result is a duty cycle oscillator where the ratio of the high vs. low voltage coming out is proportional to the varying pressure. This converts the pressure signal into a variable duty cycle oscillator.

Figure 30B:
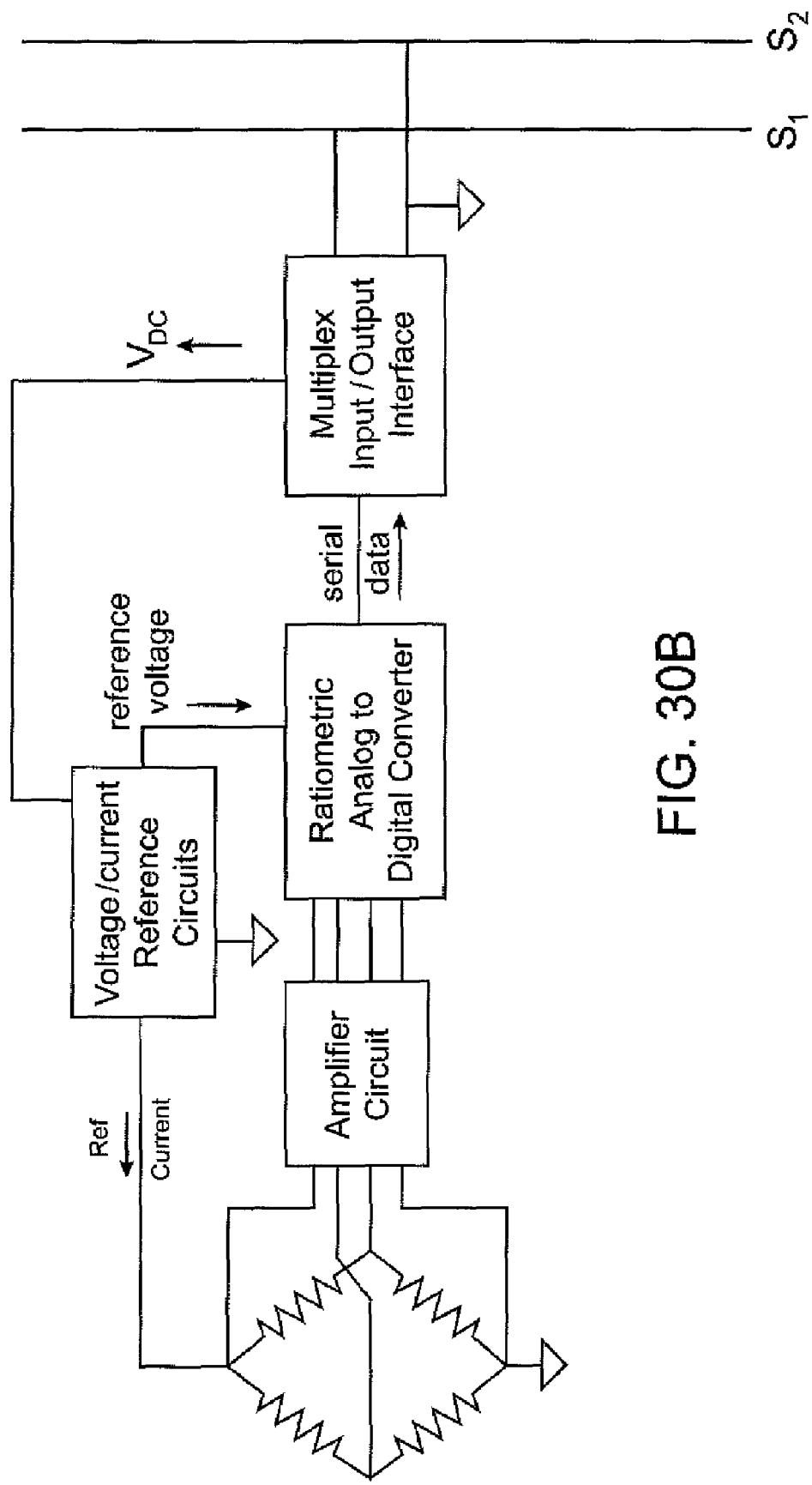
FIGS. 30B & C provide circuit diagrams of alternative embodiments of the present invention.
Figure 30C:
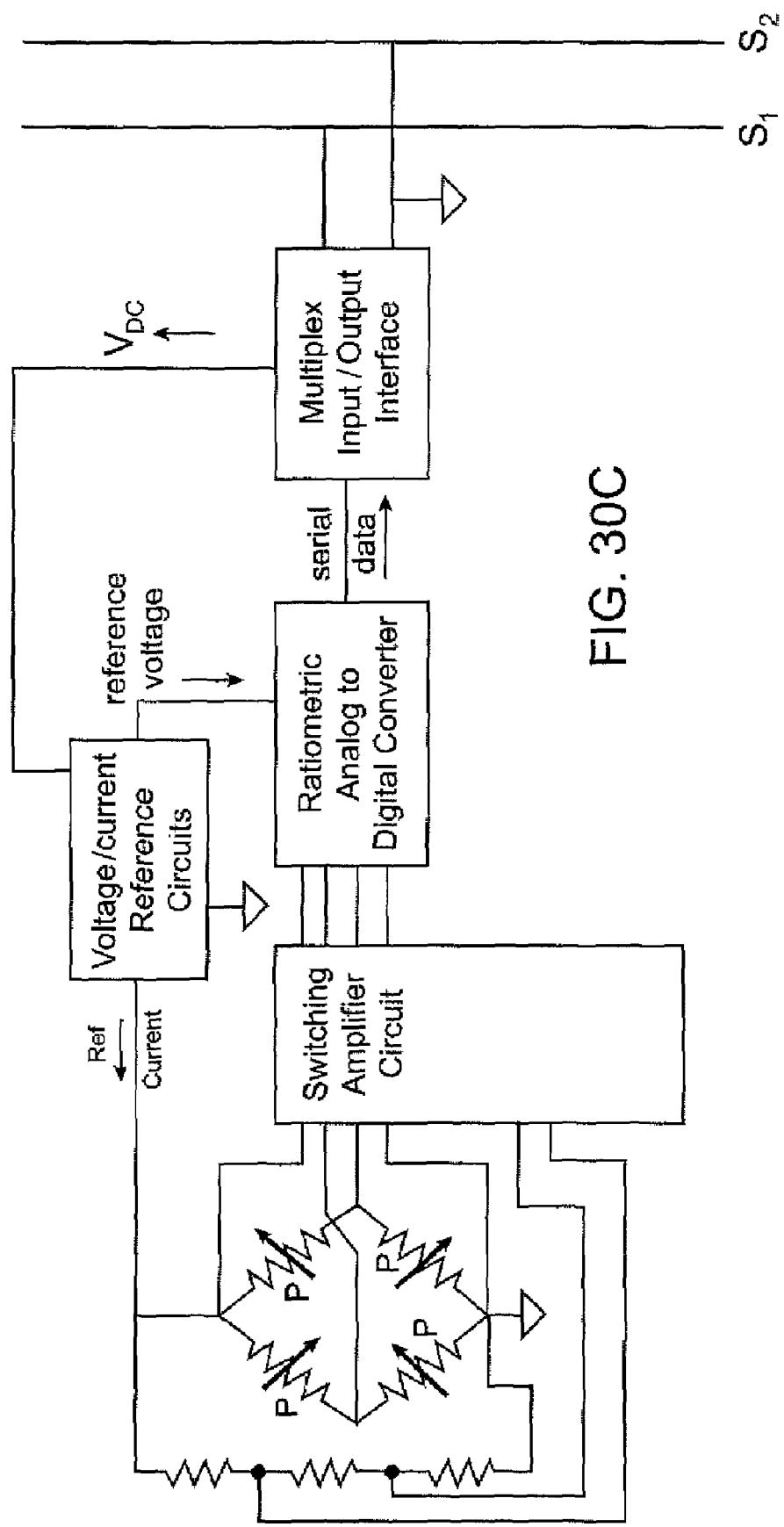

FIGS. 30B & C provide block diagrams of the subject pressure sensors integrated with a multiplex system.

Signal Conversion

A variety of signal conversion techniques may be applied to convert the analog voltage that represents pressure into a robust signal. For example, the analog voltage may be converted into a number using an analog to digital converter, or the analog voltage may be converted to a frequency using an voltage controlled oscillator, both of which are commercially available as a component or as a cell layout for an Application-Specific Integrated Circuit (ASIC). Other less well know approaches include a voltage-controlled duty cycle oscillator to convert the varying pressure signal into a varying duty cycle of a stable oscillator. The circuits of FIGS. 29 and 30 may be incorporated as an ASIC and integrated with the sensor using either chip-scale or wafer-scale bonding techniques.

Some embodiments of the sensor device may further include a layer of material coupled with the substrate such that the layer is positioned between the diaphragm and the volume. For example, the layer of material may comprise a layer of silicone. In some embodiments, the diaphragm and the layer of material are separated by a space.

Individually Addressable Modular Pressure Sensing Units

According to one embodiment of the present invention, individually addressable modular pressure sensing units are placed along two wires within a pacing lead coupled to an implantable device. Each pressure sensing unit includes an integrated circuit ("control chip") which is interfaced to a number of pressure sensors and the two wires. In one embodiment, a pressure sensor detects cardiac pressure through a Wheatstone bridge (e.g., as described above), which includes a pressure-sensitive resistive resistor. During operation, the control chip selects one of the Wheatstone bridges and drives a reference voltage through the Wheatstone the bridge. The control chip also detects a response voltage from the Wheatstone bridge which indicates the cardiac pressure.

One embodiment of the present invention uses an ultra-fast pre-amplification circuit that allows the control chip to apply the reference voltage to the Wheatstone bridge for only a short period, thus minimizing the risk of current leaking into the patient's body.

In other embodiments of the present invention, the control chip mitigates the effect of electromigration in the Wheatstone bridge by regularly inverting the direction of the current flowing through the Wheatstone bridge. Hence, by effectively driving an AC current through the resistors, the system can extend the life of the pressure sensor significantly.

The control chip can also be configured to calibrate a Wheatstone bridge by measuring an offset voltage when the Wheatstone bridge is not under any pressure. A received control command can cause the control chip to set a proper gain and to measure the voltage offset, which may be caused by resistance drifting of the four resistors in the bridge due to time or temperature variation.

In other embodiments of the present invention, the pressure measurement occurs in cycles. In each cycle, an external signal detection and analysis system provides the power supply and the control commands to the control chip simultaneously. The control commands are carried in bits encoded with a frequency shift keying (FSK) signal imposed upon a constant voltage signal. In one embodiment, the digital commands can be carried by a 0.5-volt peak-to-peak FSK signal imposed on a 5-volt signal. The control chip is configured in such a way that, after all the control commands are received, the selection of a Wheatstone bridge, the application of a reference voltage to the bridge, the measurement, amplification, and digitization of the measured signal, the buffering of the signal, and the communication of the buffered signal happen sequentially before the measurement cycle is complete.

In a further embodiment, the measurement cycle, and correspondingly the power supply on the two bus wires, lasts approximately 50 µs. The reference voltage is applied on the selected bridge for approximately 1 µs. Such a short operation time of the pressure sensing system can significantly reduce the risks to a patient.

Location of Pressure Sensors and Control Chips

Figure 31:
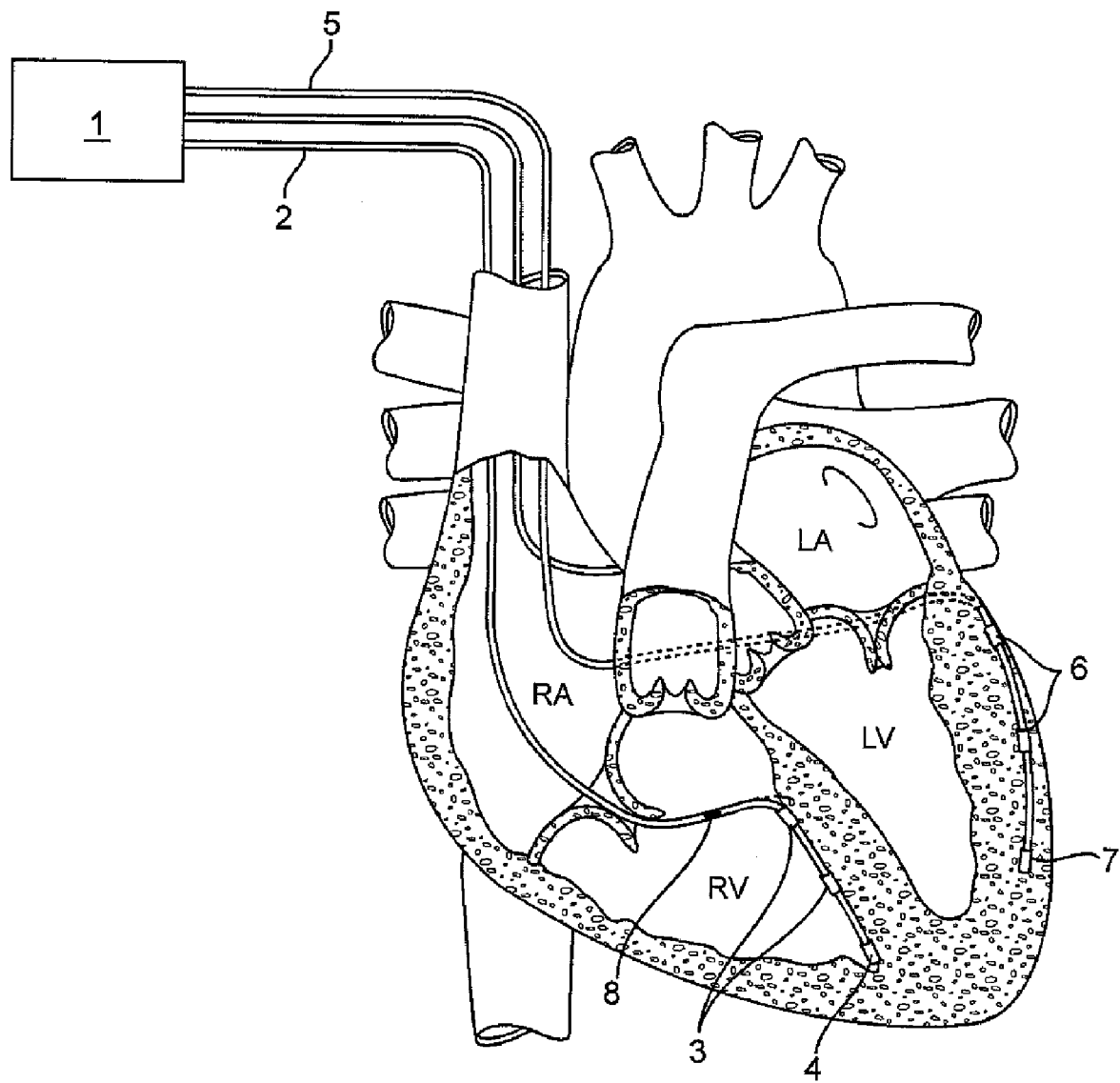
FIG. 31 illustrates the location of a number of pressure sensors in accordance with an embodiment of the present invention.

One embodiment of the present invention provides a cardiac pressure detection and analysis system comprising a number of pressure sensors which are controlled by low-power integrated circuits located with the pressure sensors ("control chips"), wherein the control chips are coupled to a signal analysis and power supply unit through two wires. Examples of control chip structures readily adaptable to the present invention are described in published PCT application Publication Nos. WO 2006/069322 and WO2006/029090; the disclosures of which are herein incorporated by reference. FIG. 31 illustrates the locations 3, 4, 6, 7, and 8 of a number of pressure sensors in accordance with an embodiment of the present invention. As shown in FIG. 1, a signal detection system 1 provides the extracardiac communication and calculation means for the overall system. In some embodiments, signal detection system 1 may be a pacing can residing in an external or extracorporeal location.

Right ventricular lead 2 emerges from a communication device in signal detection system 1, and travels from the subcutaneous location of signal detection system 1 into the patient's body via, for example, the subclavian venous access. The distal portion of right ventricular lead 2 is preferably located along the intraventricular septum, terminating with fixation in the right ventricular apex. As shown in FIG. 31, right ventricular lead 2 includes pressure sensors positioned at locations 3, 4, and 8. The number of pressure sensors in ventricular lead 2 is not limited, and may be more or less than the number of pressure sensors shown in FIG. 31.

Similarly, left ventricular lead 5 emerges from signal detection system 1, following substantially the same route as right ventricular lead 2 through, for example, the subclavian venous access and the superior vena cava into the right atrium. In the right atrium, left ventricular lead 5 is threaded through the coronary sinus around the posterior wall of the heart in a cardiac vein draining into the coronary sinus. Left ventricular lead 5 is provided laterally along the walls of the left ventricle, which is a likely position to be advantageous for bi-ventricular pacing. FIG. 31 further shows pressure sensors positioned at locations 6 and 7 of left ventricular lead 5.

Figure 32:
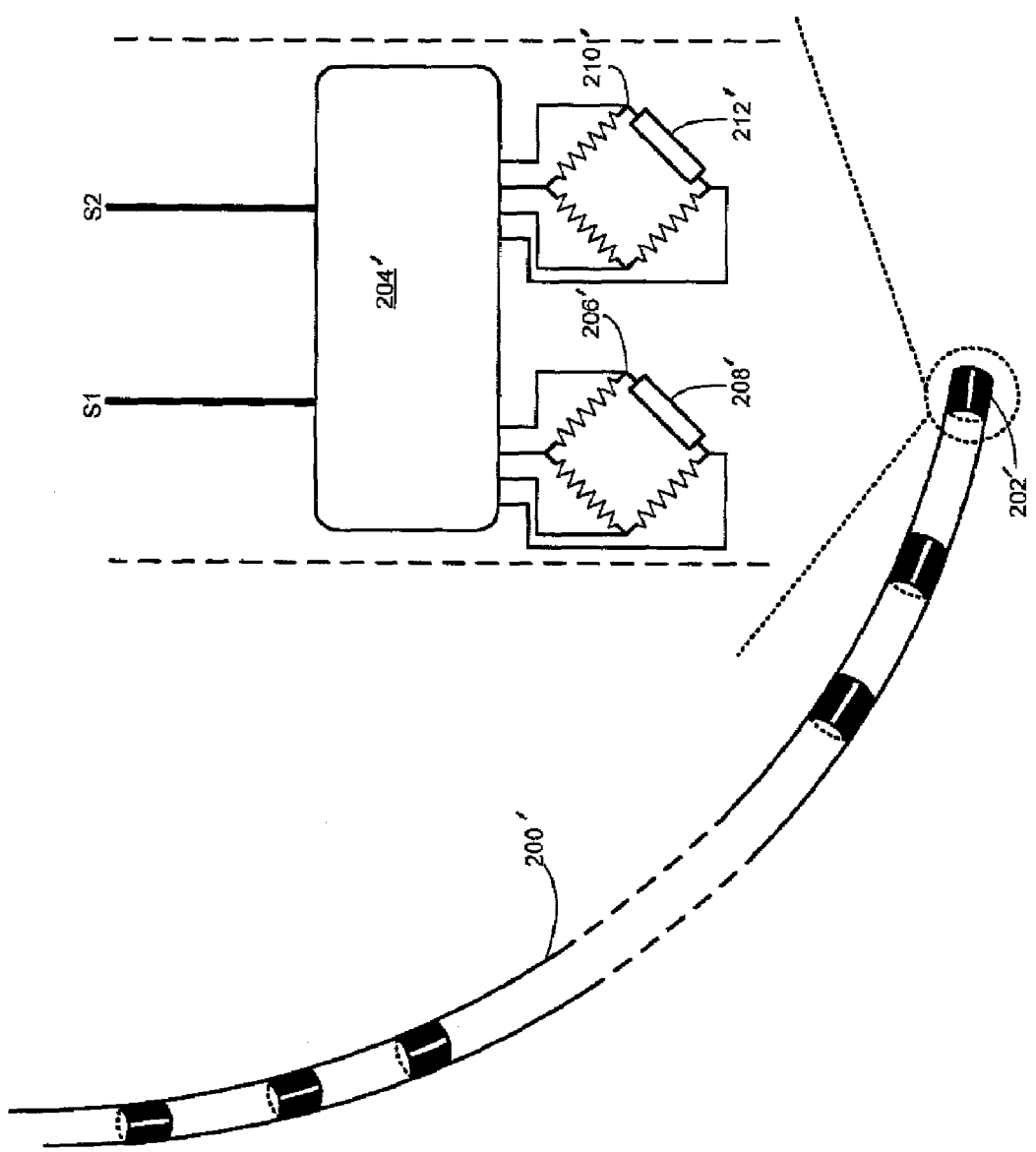
FIG. 32 illustrates an exemplary external view of a number of pressure sensors with corresponding control chips in accordance with an embodiment of the present invention.

FIG. 32 illustrates an exemplary external view of a number of pressure sensors with the corresponding control chips in accordance with an embodiment of the present invention. As shown in FIG. 32, the power supply, control commands, and the subsequent signals relating to measured pressure are all communicated along bus wires S1 and S2, in either direction. In one embodiment, bus wires S1 and S2 are coupled to a number of, for example eight, control chips controlling the corresponding pressure sensors.

In one embodiment, pacing lead 200' accommodates a number of pressure sensors, such as pressure sensor 202'. As shown in the zoom-in view, pressure sensor 202' includes a control chip 204' coupled to bus wires S1 and S2, and two Wheatstone bridges 206' and 210', which include two pressure-sensitive resistors 208' and 212', respectively. In one embodiment, the pressure-sensitive resistor uses a membrane and a piece of piezo-electric material, the resistance of which varies according to the pressure exerted thereupon. In a further embodiment, the resistance of the four resistors in a Wheatstone bridge is substantially the same when no external pressure is present.

During operation, control chip 204' selects one of the Wheatstone bridges, for example, bridge 206', and drives a reference voltage via two opposite locations, for example, the north and south points, of the bridge. If the bridge is not under pressure, the voltages at the other two opposite locations, which are the west and east points in this example, are substantially the same. If the bridge is under pressure and the pressure sensitive resistor 208' exhibits a different resistance, control chip 204' can detect a voltage difference between the west and east points of the bridge.

In a further embodiment, control chip 204' can be configured to calibrate Wheatstone bridge 206' by measuring the voltage offset between the west and east points when bridge 206' is not under any pressure. A received control command can cause control chip 204' to set a proper gain and to measure the voltage offset. Such voltage offset may be caused by resistance drifting of the four resistors in the bridge due to time or temperature variation.

According to one embodiment, the system conducts communications via bus wires S1 and S2 in three phases, namely a configuration phase, a measurement phase, and a signal return phase. During the configuration phase, a separate signal detection and analysis system, which may reside remotely from the control chip and the pressure sensors (e.g., in a pacing can), sends configuration signals to specify which control chip to activate and which Wheatstone bridge coupled to the activated control chip is to be operational. The configuration signals, which include various addresses and control commands, are provided to all the control chips coupled to bus wires S1 and S2. These configuration signals may be, for example, 0.5-volt peak-to-peak pulses modulated with frequency-shift-keying (FSK) modulation on a 5-volt DC signal.

Subsequent to the configuration phase, the signal detection and analysis system may provide a driving voltage for measuring the voltage difference across the selected Wheatstone bridge. Control chip 204' then drives a reference voltage across the Wheatstone bridge, and measures the corresponding voltage difference in the other two opposite locations. One embodiment of the present invention uses an ultra-fast pre-amplification circuit that allows control chip 204' to apply the reference voltage to the bridge for only a short period, thus minimizing the risk of current leaking into the patient's body. The period during which voltage is applied to the bridge is less than approximately 10 µs. In a further embodiment, this period is approximately 1 µs.

Because of the short exposure of the Wheatstone bridge to the reference voltage, the risks to the patient are now significantly reduced. However, if current flows only in one direction through the Wheatstone bridge, electromigration may slowly degrade the accuracy of the measurements. Electromigration is the transport of material caused by the gradual movement of the ions in a conductor due to the momentum transfer between conducting electrons and diffusing metal atoms. This effect becomes more pronounced in an integrated circuit, such as the one used here for implantable devices where high current densities are present. One embodiment of the present invention mitigates the effect of electromigration by regularly inverting the direction of the current flowing through the Wheatstone bridge. Hence, by effectively driving an AC current through the resistors, the system can extend the life of the pressure sensor significantly.

After the measurement phase, the system enters the signal return phase. The measured voltage difference across the west and east points of the selected Wheatstone bridge is subsequently amplified, digitized, and stored in a local buffer within chip 204'. The signal detection and analysis system transmits a DC voltage over the two bus wires S1 and S2. Control chip 204' transmits the stored digital signal serially by modulating the voltage carried on S1 and S2. In one embodiment, control chip 204' uses a switch to change the load placed over S1 and S2, and thus to change the voltage between S1 and S2 as measured by the signal detection and analysis system residing, for example, in a pacing can.

During operation, the pressure measurement occurs in cycles. In each cycle, the external signal detection and analysis system provides the power supply and the control commands to the control chip simultaneously. In one embodiment, the control commands are carried in bits encoded with a frequency shift keying (FSK) signal imposed upon a constant voltage signal. For example, the digital commands can be carried by a 0.5-volt peak-to-peak FSK signal imposed on a 5-volt signal. The control chip is configured in such a way that, after all the control commands are received, the selection of a Wheatstone bridge, the application of a reference voltage to the bridge, the measurement, amplification, and digitization of the measured signal, the buffering of the signal, and the communication of the buffered signal happen sequentially before the measurement cycle is complete. In one embodiment, the measurement cycle, and correspondingly the power supply on the two bus wires, lasts approximately 50 μs. The reference voltage is applied on the selected bridge for approximately 1 μs. Such a short operation time of the pressure sensing system can significantly reduce the risks a patient is subject to.

Control Chip Architecture

Figure 33:
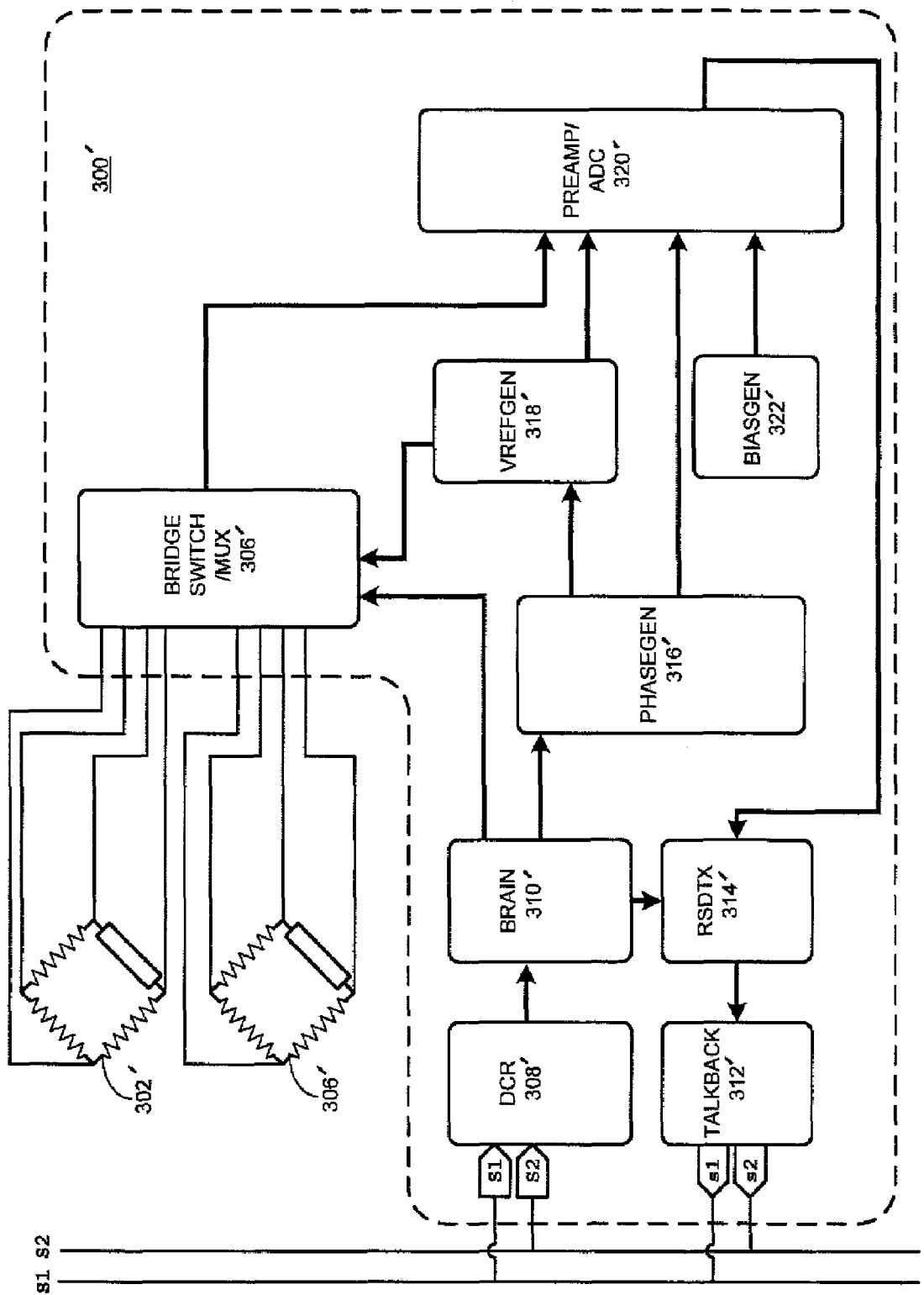
FIG. 33 illustrates a high-level block diagram of a control chip for controlling pressure sensors in accordance with an embodiment of the present invention.

FIG. 33 illustrates a high-level block diagram of a control chip for controlling pressure sensors in accordance with an embodiment of the present invention. As shown in FIG. 33, a control chip 300' is configured to communicate with Wheatstone bridges 302' and 304', and bus wires S1 and S2. Control chip 300' includes a data and clock recovery (DCR) module 308', a command interpretation (BRAIN) module 310', a phase generation (PHASEGEN) module 316', a reference voltage generation (VREFGEN) module 318', a bias generation (BIAS) module 322', a bridge switch and multiplexing (BRIDGE SWITCH/MUX) module 306', a pre-amplification and A-D converter (PREAMP/ADC) module 320', a shift register (RSDTX) module 314', and a communication (TALKBACK) module 312'.

DCR module 308' carries out such functions as deriving a power supply signal, recovering a clock signal, and recovering data bits. BRAIN module 310' is responsible for decoding address signals and control commands, and configuring BRIDGE SWITCH/MUX module 306' to select the desired Wheatstone bridge and configuring PHASEGEN module 316' to set proper phase and gain for amplification of the measure the signal. PHASEGEN module 316' generates a number of control signals with different phases to control PREAMP/ADC module 320' and VREFGEN module 318'. VREFGEN module 318' produces the necessary reference voltages for BRIDGE SWITCH/MUX module 306' and PREAMP/ADC module 320'. In addition, BIAS module 322' generates the necessary bias voltages to enable PREAMP/ADC module 320' to function properly.

BRIDGE SWITCH/MUX module 306' selects one of the two Wheatstone bridges and allows a reference voltage to pass to the selected bridge when a signal is received from the BRAIN module 310'. BRIDGE SWITCH/MUX module 306' also allows the measured voltage to be communicated to PREAMP/ADC module 320', which amplifies the measured voltage with proper gain and digitizes the analog signal into a series of bits. The digital value is then stored in RSDTX module 314'. In one embodiment, BRAIN module 310' also checks a parity bit transmitted with data used as a redundancy check and, if the parity bit does not match with the parity of the running data bits, prevents RSDTX module 314' from communicating the digitalized value back. If the parity bit is correct, TALKBACK module 312' extracts the bits stored in RSDTX module 314' and modulates the voltage on S1 and S2 according to the bits.

In one embodiment of the present invention, the aforementioned functions of control chip 300' are carried out by customized digital circuits and therefore, not carried out by executing software or middle-ware. This approach provides the advantages of low-power operation and a fast response time.

Ultra-Fast Pre-Amplification Circuit

One challenge in designing a safe implantable cardiac pressure sensor is to introduce as little voltage to an implanted device for as a short period as possible. Typically, a power-supply voltage lasting for less than 50 μs is considered to be safe for an implanted device. Furthermore, the time during which a current is flowing through the Wheatstone bridge is ideally as short as possible, so that the risk of current leaking into the patient's tissue is minimized. These requirements present a challenge for the PREAMP/ADC module, because conventional digital pre-amplification circuits using switched capacitors typically require a long period for a voltage to build up.

Figure 34A:
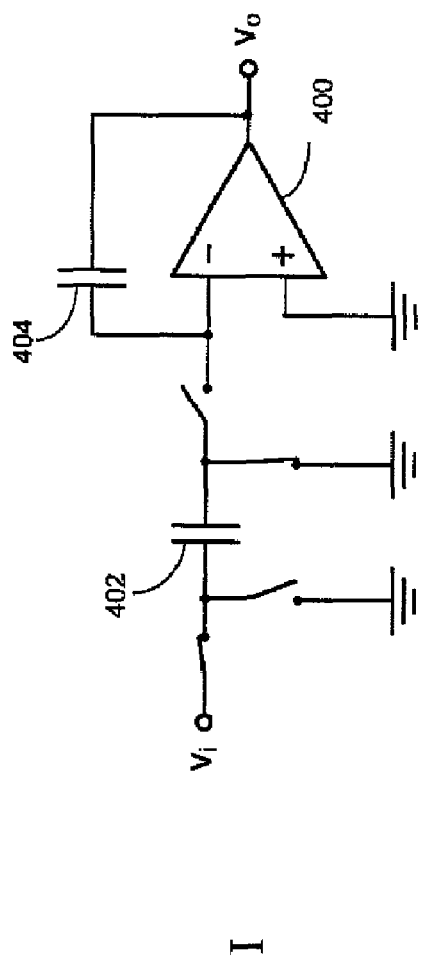
FIG. 34A illustrates a conventional amplification circuit using switched capacitors.
Figure 34A:
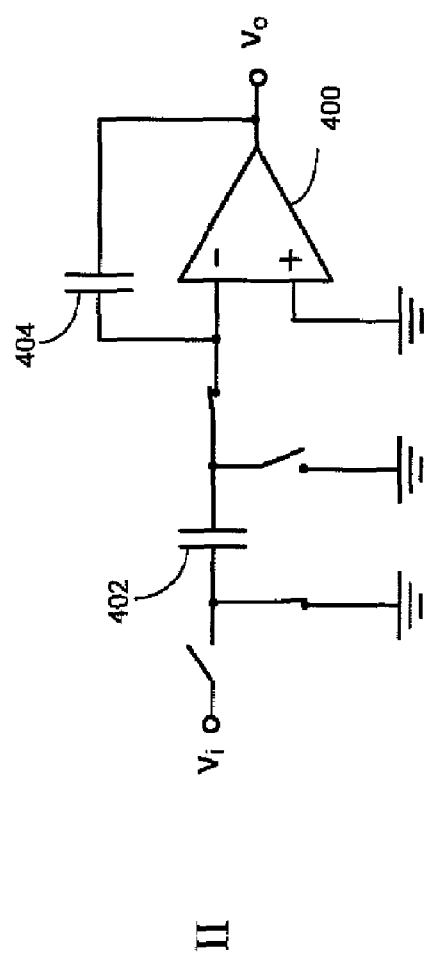

For example, FIG. 34A illustrates a conventional amplification circuit using switched capacitors. The exemplary switched-capacitor circuit includes an opamp 400, an input capacitor 402, and a feedback capacitor 404. FIG. 34A illustrates the two states in which the circuit operates. In state I, the switches are configured in such a way that capacitor 402 is coupled between an input voltage $v_i$ and the ground. After stabilizing, the voltage across capacitor 402 is substantially the same as $v_i$. Subsequently, the switches are reconfigured as shown in state II where capacitor 402 is coupled to the negative input of opamp 400, the voltage of which is substantially at the ground level. Because both sides of capacitor 402 are now coupled to the ground level, the charge accumulated across capacitor 402 can only move to capacitor 404. Therefore, the voltage across capacitor 404, which is also the output voltage $v_o$, is $v_o+v_i$.

By alternating between states I and II, the circuit can gradually build up the output voltage $v_o$ to a desired level. For example, if a 64× gain is desired, the circuit can be configured to cycle through these two states 64 times. However, the charge accumulation process in this circuit is linear, and the input voltage $v_i$ is to be present during the entire process. Such a requirement is difficult to meet when the input voltage is the measured voltage across a Wheatstone bridge used as a cardiac pressure sensor. If this circuit is used, the Wheatstone bridge would need to be turned on for a long period of time, which increases the risk to the patient significantly.

Figure 34B:
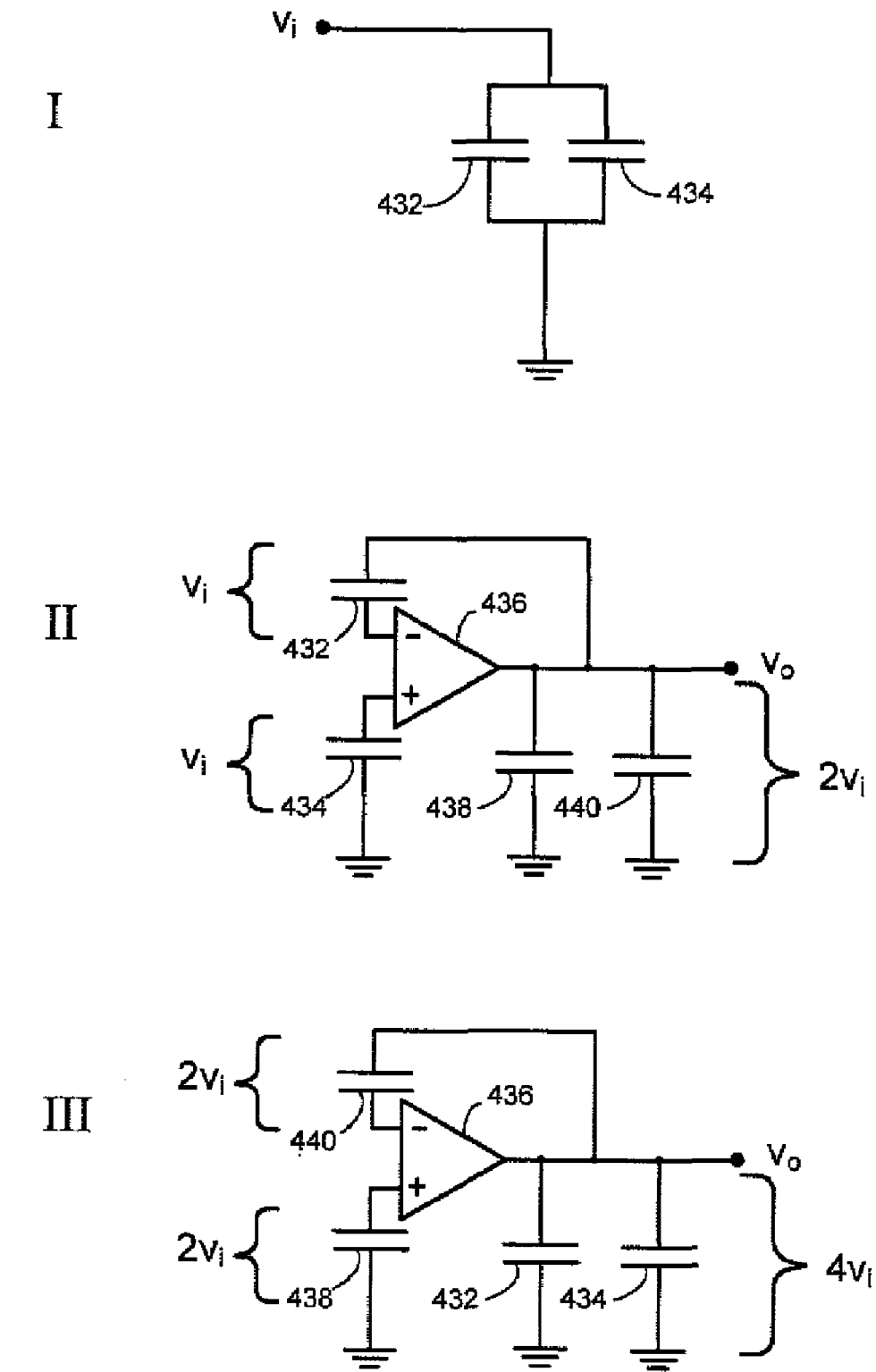
FIG. 34B illustrates the principle of operation of an ultra-fast amplification circuit in accordance with one embodiment of the present invention.

One embodiment of the present invention uses a novel ultra-fast amplification circuit. FIG. 34B illustrates the principle of operation of such an ultra-fast amplification circuit. The circuit includes an opamp 436, four capacitors 432, 434, 438, and 440, and a number of switches for reconfiguring the circuit. In the initial state I, capacitors 432 and 434 are coupled in parallel between the ground and an input voltage $v_i$. As a result, each capacitor has a voltage drop of $v_i$. In state II, the switches are configured so that capacitor 434 is coupled between the ground and the positive input of opamp 436, and capacitor 432 is coupled between the negative input and the output of opamp 436. Consequently, the output voltage of opamp 436, $v_o$, is at 2 $v_i$. In addition, the two output capacitors 438 and 440 both exhibit a voltage drop of 2 $v_i$.

Subsequently, in state III, the switches are reconfigured so that capacitor 438 is coupled between the ground and the positive input of opamp 436, and capacitor 440 is coupled between the negative input and the output of opamp 436. Because both capacitors 432 and 434 retain the charge, the output voltage $v_o$ is now at 4 $v_i$. Therefore, by switching between state II and state III, the output voltage can be amplified by two with each cycle. This amplification method is much faster than the conventional amplification performed by a linear switched-capacitor circuit. Moreover, the illustrated circuit eliminates the need for the input voltage $v_i$ to be available throughout the entire amplification process. Instead, $v_i$ only needs to be available at the initial state I. Therefore, this ultra-fast amplification can be used for Wheatstone-bridge-based cardiac pressure sensors, because the system can apply the reference voltage on the Wheatstone bridge for a short period during the initial state, and then turn off the Wheatstone bridge. The PREAMP/ADC module using this ultra-fast amplification circuit can attain the desired amount of gain by performing a predetermine number of cycles through state II and state III as shown in FIG. 34B. Note that the number of cycles is determined by PHASEGEN module 316'.

Figure 35A:
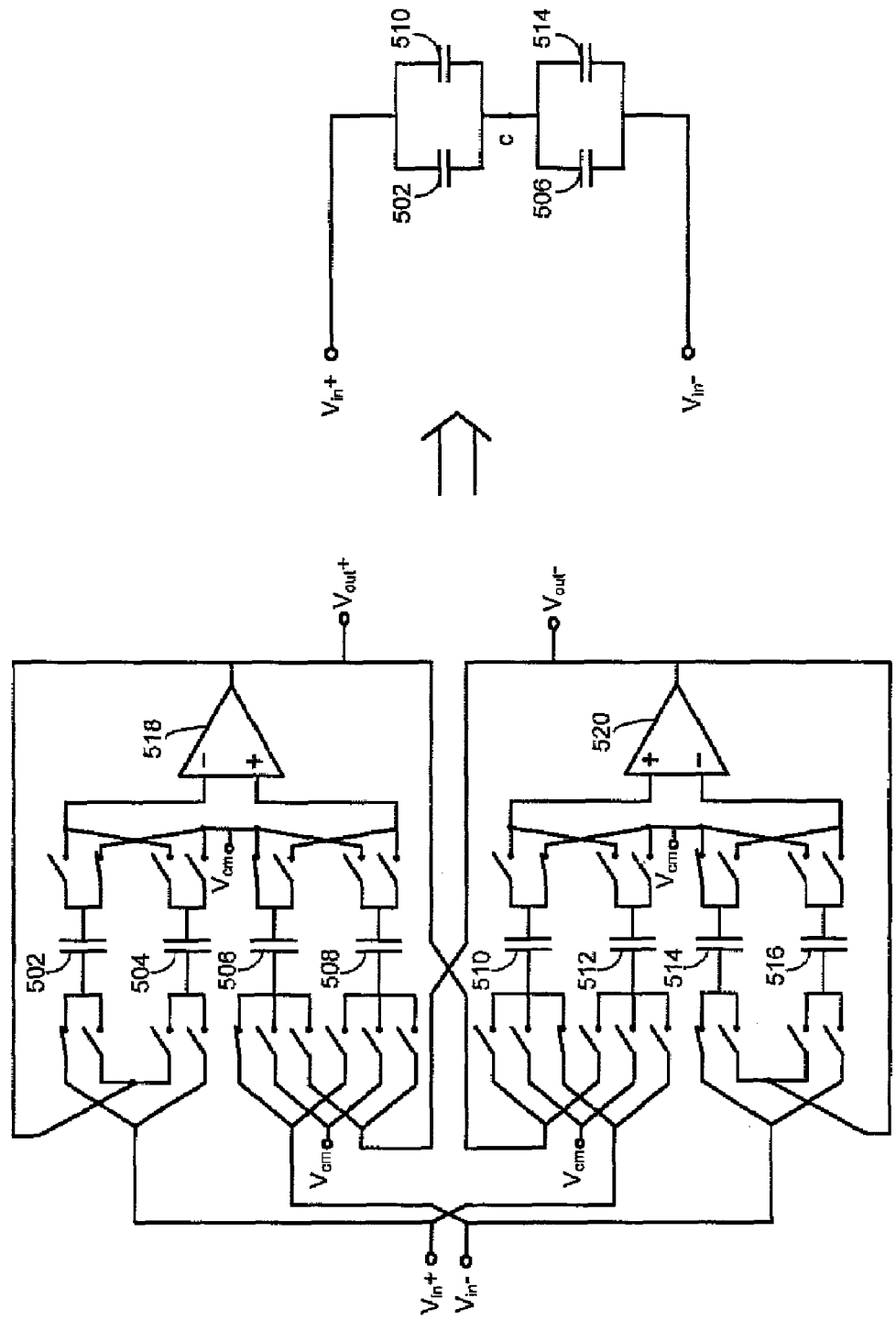
FIG. 35A illustrates a first state of an ultra-fast pre-amplification circuit in accordance with an embodiment of the present invention.
Figure 35B:
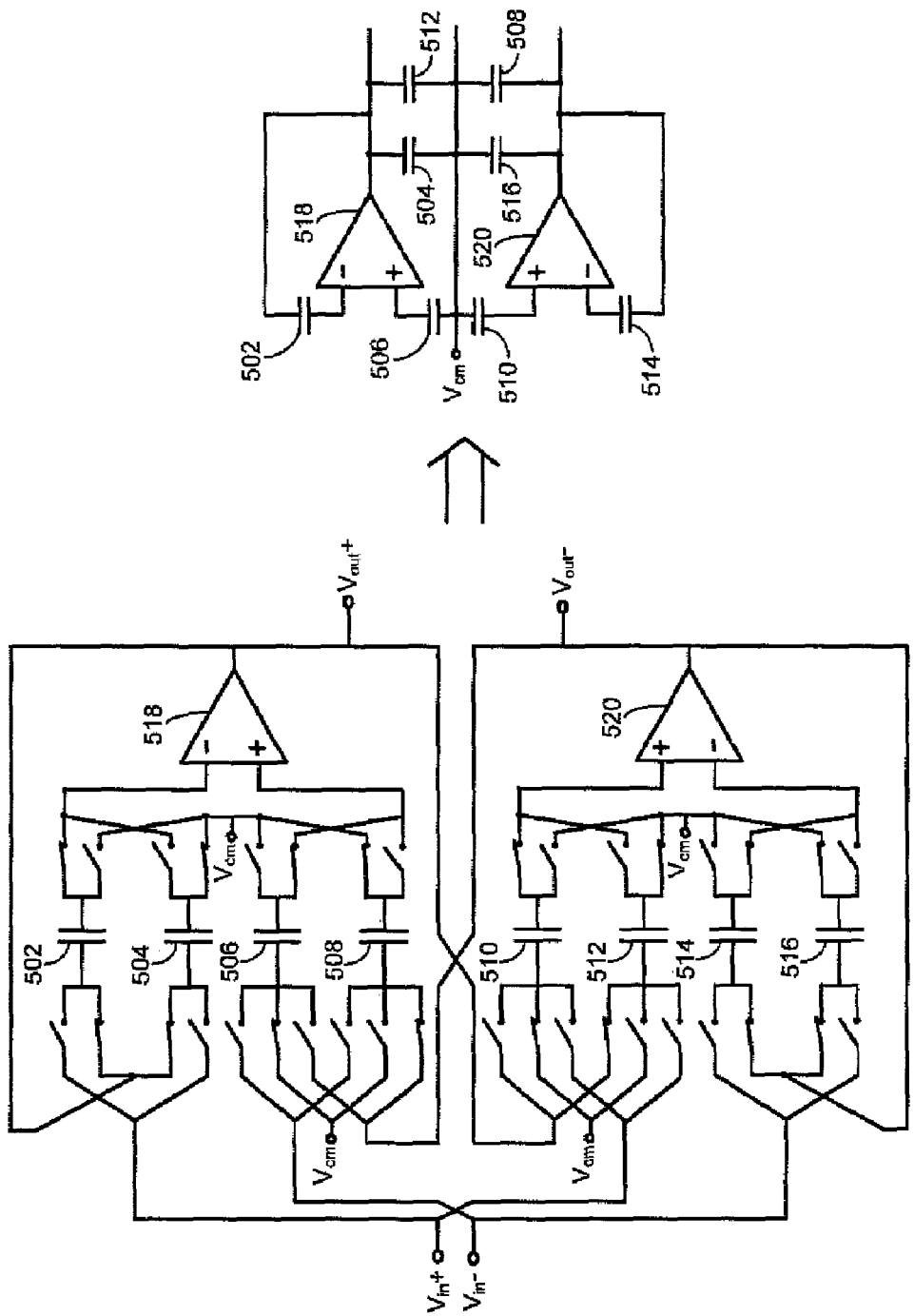
FIG. 35B illustrates a second state of the ultra-fast pre-amplification circuit in accordance with an embodiment of the present invention.
Figure 35C:
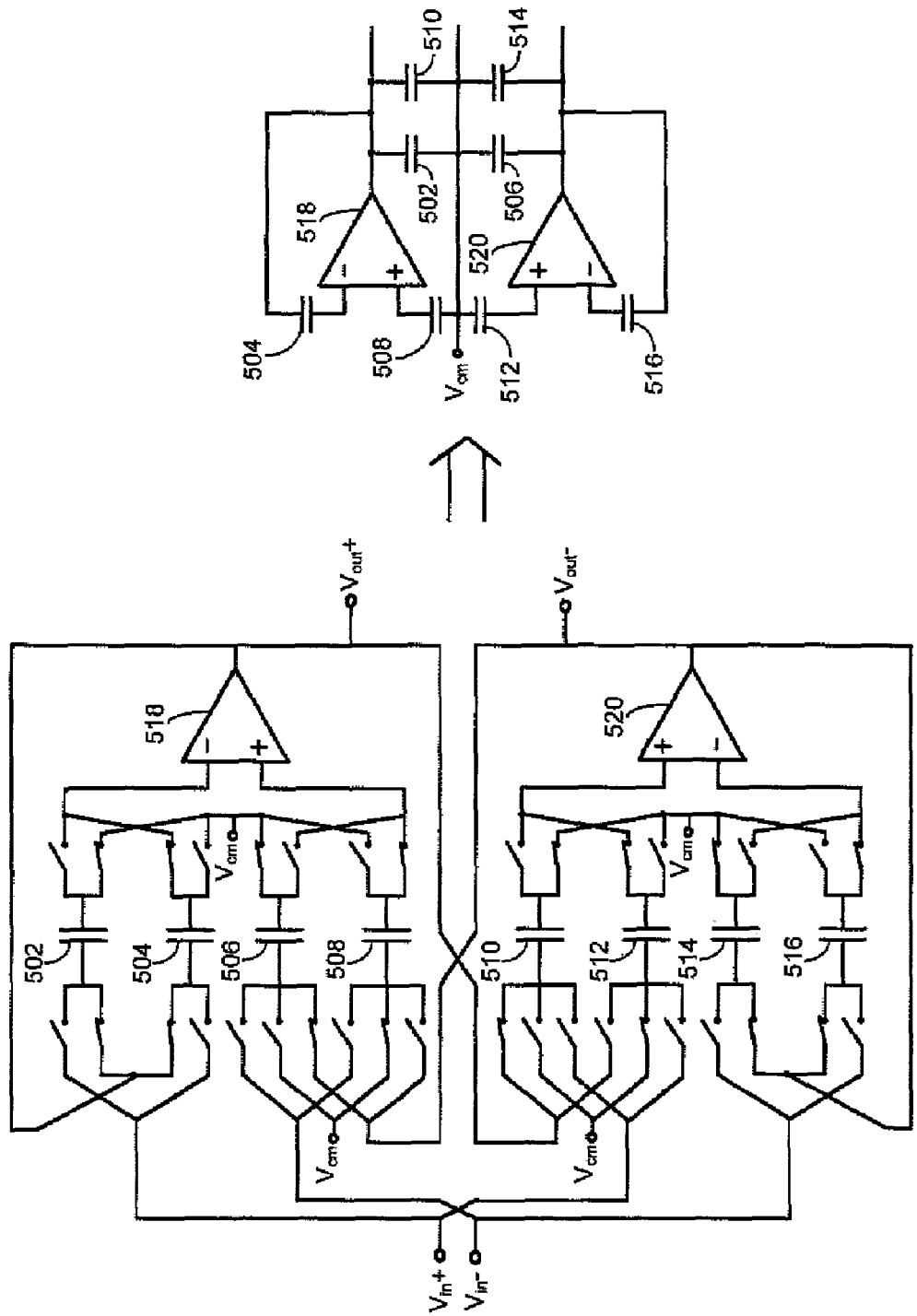
FIG. 35C illustrates a third state of the ultra-fast pre-amplification circuit in accordance with an embodiment of the present invention.

FIGS. 35A-35C illustrate the three states of an exemplary implementation of a differential amplifier employing the ultra-fast amplification circuit. The amplifier includes two opamps 518 and 520, eight capacitors 502-516, and a number of transistor-based switches. The reconfiguration of the switches is controlled by signals generated by PHASEGEN module 316'. In one embodiment, the switches are based on MOS transistors. FIG. 35A illustrates the initial state of the circuit. Two differential inputs, $v_{in+}$ and $v_{in-}$, provide the differential input voltage. A common-mode voltage, $v_{cm}$, is also provided to the circuit as is shown in FIG. 35A. In this state, the switches are so configured that capacitors 502 and 510 are coupled in parallel between $v_{in+}$ and $v_{cm}$, and that capacitors 506 and 514 are coupled in parallel between $v_{cm}$ and $v_{in-}$. In this way, these four capacitors are initially charged with the differential input voltage.

FIG. 35B illustrates a second state of the circuit. In this state, previously charged capacitors 506 and 502 are coupled to the positive input and negative input of opamp 518, respectively. Capacitors 504 and 512 are coupled between the output of opamp 518 and $v_{cm}$. Similarly, previously charged capacitors 510 and 514 are coupled to the positive input and negative input of opamp 520, respectively. Capacitors 516 and 508 are coupled between the output of opamp 516 and $v_{cm}$. As a result, the differential output voltage between $v_{out+}$ and $v_{out-}$ is twice the differential input voltage, $2\times(v_{in+}-v_{in-})$.

Next, as is shown in FIG. 35C, the system enters a third state, where the switches are reconfigured so that the capacitors coupled to an output of an opamp in the previous state are now coupled to an input of an opamp. For example, capacitors 504 and 508, which carry a total voltage of $2\times(v_{in+}-v_{in-})$, are now coupled to the negative input and positive input of opamp 518, respectively. Similarly, capacitors 512 and 516 are now coupled to the inputs of opamp 520. Capacitors 502 and 510 are in turn coupled between the output of opamp 518 and $v_{cm}$. Further, capacitors 506 and 514 are coupled between the output of opamp 520 and $v_{cm}$. The resulting differential output voltage ($v_{out+}-v_{out-}$), is four times the initial differential input voltage, $4\times(v_{in+}-v_{in-})$. Therefore, by continuously switching between the second and third states, this circuit can quickly amplify the input signal to a desired level.

The amplification circuit shown in FIGS. 5A-5C allows the control chip to apply a reference voltage across the selected Wheatstone bridge for only a very short period of time. While the amplification is in process, the circuit does not require sustained differential input. Therefore, the Wheatstone bridge can be turned off quickly after charging the circuit for the first time.

Reducing Charge Injection

Figure 36A:
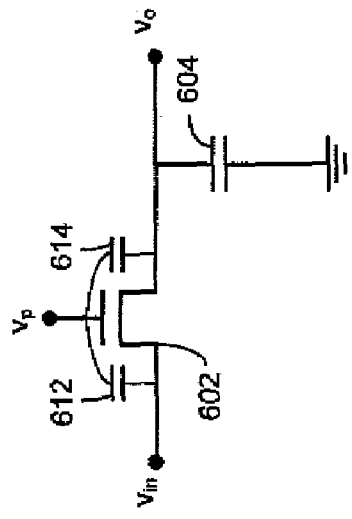
FIG. 36A illustrates an example of charge injection that occurs when an NMOS transistor is switched.

Charge injection typically occurs when a transistor is used to switch the voltage applied to a capacitor. Charge injection is undesirable, particularly for switched capacitor circuits, because charges injected from the inherent capacitors within transistors can cancel the voltage accumulated across a capacitor. As a result, the efficiency of an amplification circuit as described above can be reduced. FIG. 36A illustrates an exemplary scenario where charge injection can affect the result of a switched capacitor circuit. In this example, a capacitor 604 is coupled to the source of an NMOS transistor 602, whose drain is coupled to an input voltage $v_{in}$. The gate of NMOS transistor 602 is coupled to a control signal $v_p$. NMOS transistor 602 exhibits inherent capacitance between the gate and the source, and between the gate and the drain. These two inherent capacitors are denoted as capacitors 614 and 612, respectively.

When the gate voltage $v_p$ is at a high voltage, for example, 5 V, NMOS transistor 602 is turned on, and the voltage on capacitor 604 is substantially the same as $v_{in}$. However, if $v_{in}$ is less than 5 V, for example, 2.5 V, the inherent capacitors 612 and 614 are both charged as well. When NMOS transistor 602 is turned off to preserve the voltage on capacitor 604, the negative charges accumulated in inherent capacitor 614 are injected to capacitor 604, neutralizing the positive charges accumulated on capacitor 604 and reducing the output voltage $v_o$.

Figure 36B:
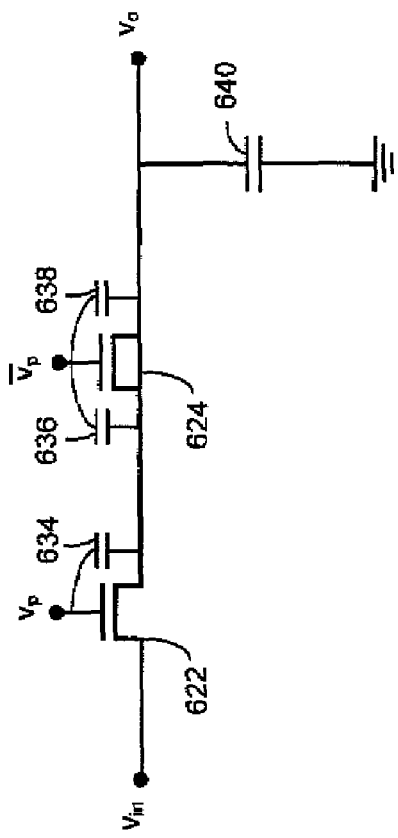
FIG. 36B illustrates a circuit for mitigating charge injection during transistor switching by using a dummy transistor in accordance with an embodiment of the present invention.

One embodiment of the present invention mitigates the charge-injection problem by using one or more dummy transistors. FIG. 36B illustrates a circuit for mitigating charge injection during transistor switching by using a dummy transistor in accordance with an embodiment of the present invention. Capacitor 640 is coupled to NMOS transistor 622, which has an inherent gate-to-source capacitance represented by capacitor 634. A source-drain-connected dummy NMOS transistor 624 is coupled between capacitor 640 and the source of NMOS transistor 622. The inherent gate-to-drain and gate-to-source capacitance within transistor 624 is represented by capacitors 636 and 638, respectively.

The gate of dummy transistor 624 is coupled to a voltage, denoted as $v_p$-bar, which has an opposite phase as the gate voltage of transistor 622, $v_p$. Therefore, when $v_p$ is at a high voltage level turning on transistor 622, $v_p$-bar is at a low voltage level turning off transistor 624. Transistor 624 being turned off does not have any direct effect on capacitor 640 because transistor 624's source and drain are connected. Because the gate voltages on transistors 622 and 624 are opposite, the charge stored in capacitor 634 and the charge stored in capacitors 636 and 638 are also opposite. Therefore, when $v_p$ changes from a high level to a low level turning of transistor 622, and correspondingly when $v_p$-bar changes from a low level to a high level, the charge injected from capacitor 634 is opposite from the charge injected from capacitors 636 and 638. In one embodiment, the combined capacitance of capacitors 636 and 638 are substantially the same as the capacitance of capacitor 634, so that the effect of charge injection is substantially eliminated. In a further embodiment, the width-to-length ratio of transistor 622 is twice the width-to-length ratio of transistor 624.

Figure 37:
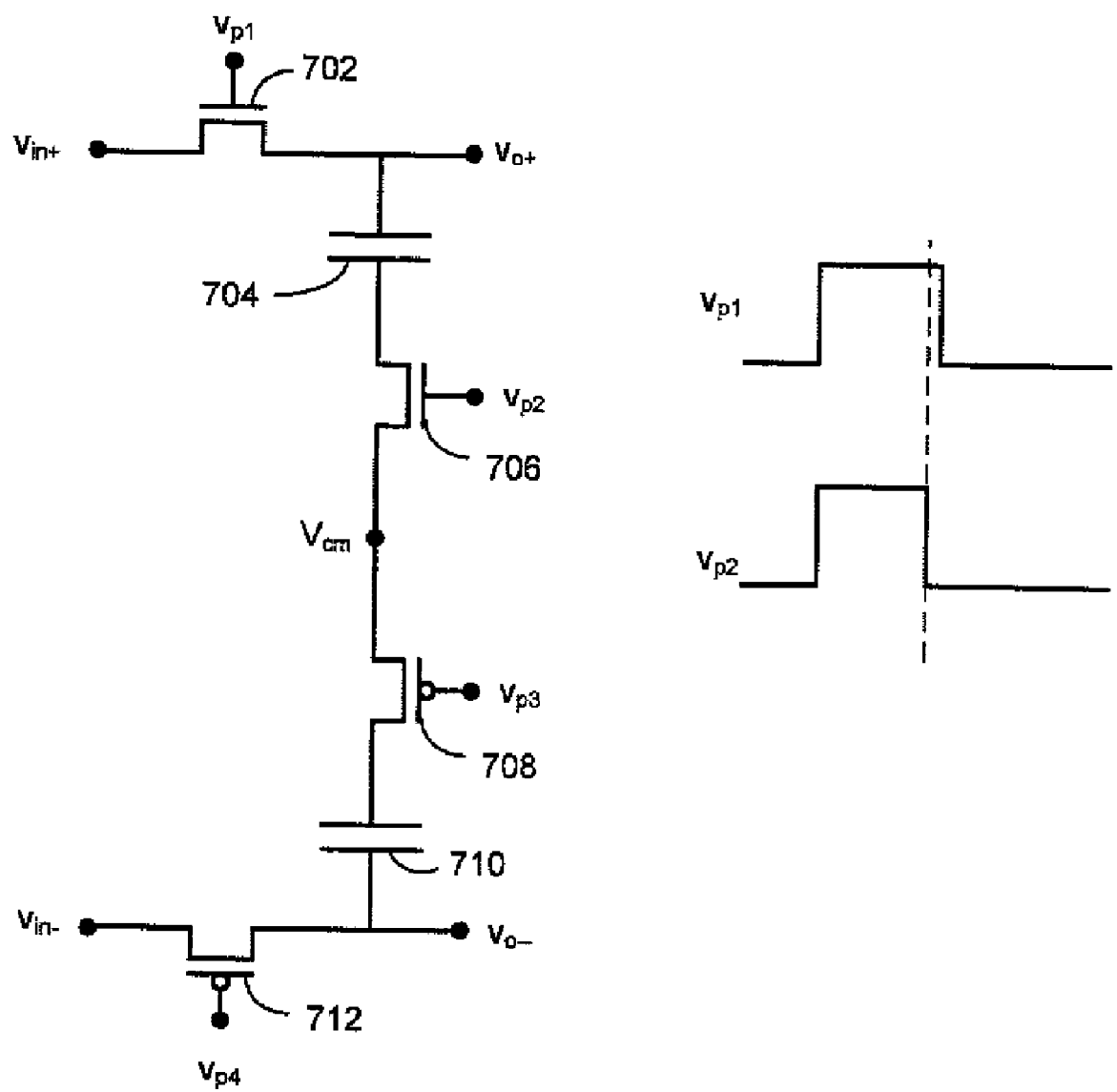
FIG. 37 illustrates a circuit for mitigating charge injection during the switching of a pair of differential signals in accordance with an embodiment of the present invention.

FIG. 37 illustrates a circuit for mitigating charge injection during the switching of a pair of differential signals in accordance with an embodiment of the present invention. The illustrated circuit example is used to preserve the input differential voltage, $(v_{in+}-v_{in-})$, on capacitors 704 and 706. Capacitors 702 and 712 are first switched on and then off to charge capacitors 706 and 708. Two additional transistors 706 and 708 are coupled between capacitors 704 and 710. Transistors 706 and 708 can be turned off to prevent charge injection from transistors 702 and 712 into capacitors 704 and 710, respectively.

During operation, all the resistors are initially turned on to allow the differential input voltage to charge capacitors 706 and 708. Transistor 706 is then turned off so that capacitor 704 is partially floating. Subsequently, when transistor 702 is turned off, because capacitor 706 is partially floating, transistor 702 is prevented from injecting charges into capacitor 704. Therefore, by dropping the gate voltage on transistor 706 slightly faster than dropping the gate voltage on transistor 702, as is shown in FIG. 7, the system can significantly reduce the charge injection from transistor 702. In one embodiment, the turning-off of transistor 706 occurs approximately 4 μs before the turning-off of transistor 702. Similarly, by turning off transistor 708 slightly faster than turning off transistor 712, the system can prevent charge injection from transistor 712 into capacitor 710.

The turning-off of transistors 706 and 708 also incurs charge injection into capacitors 704 and 710. However, such charge injection does not affect the differential output voltage ($v_{o+}-v_{o-}$).

Bias Generation

Figure 38:
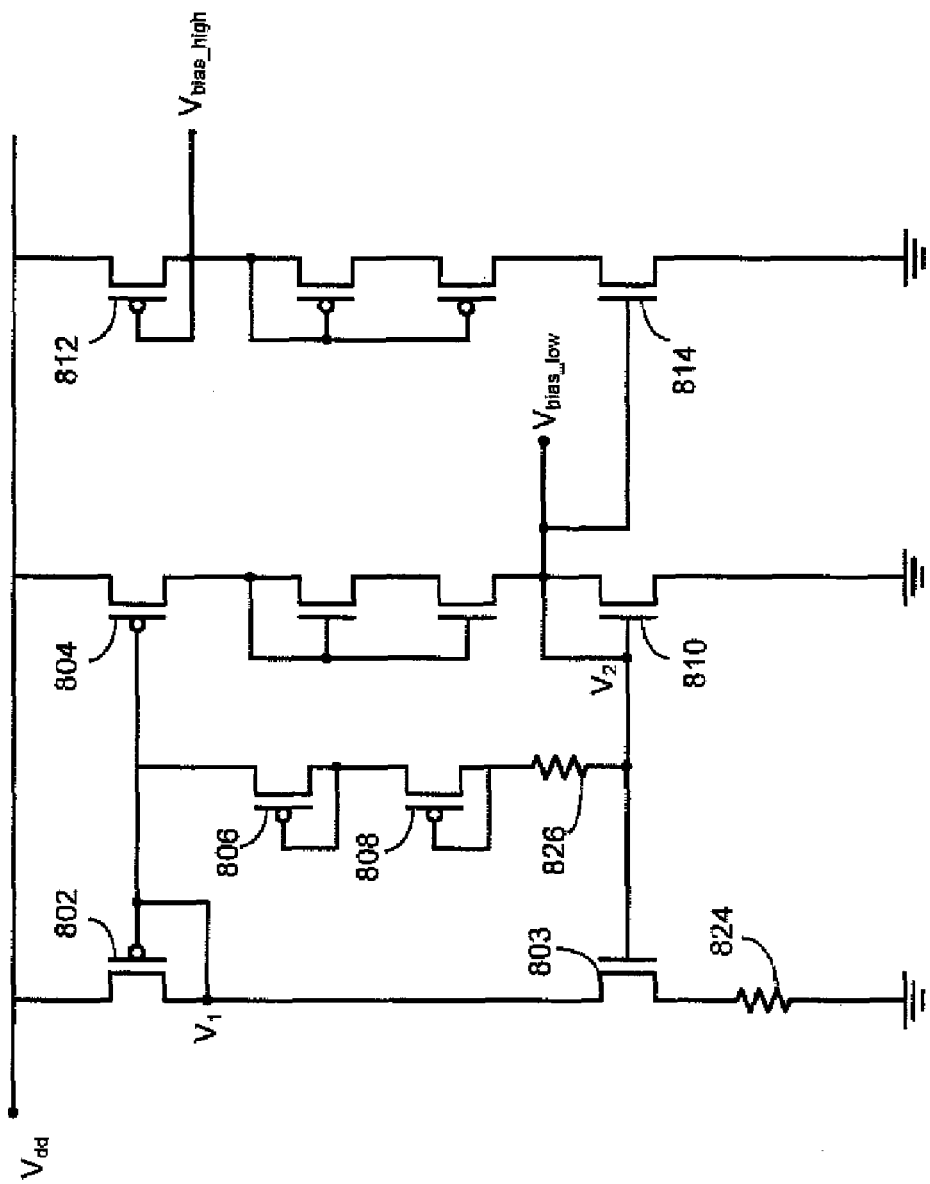
FIG. 38 illustrates an exemplary implementation of a bias voltage generation circuit in accordance with an embodiment of the present invention.

FIG. 38 illustrates an exemplary implementation of a bias voltage generation circuit in accordance with an embodiment of the present invention. Resistor 824 is used with PMOS transistor 802 and NMOS transistor 803 to generate a current, which is used in current mirrors to generate the bias voltages. For example, signal $V_{bias\_low}$ is generated by the voltage divider formed by transistors 810 and 804 using a reflected current. Similarly, signal $V_{bias\_high}$ is generated by the voltage divider formed by transistors 812 and 814.

Transistors 806 and 808, together with resistor 826 allows the current source to operate properly. Because the high-voltage power supply, $V_{dd}$, may carry additional modulated signal and thus be fluctuating, the voltage swing in $V_{dd}$ can potentially turn off transistors 803, 804, or 814. For example, in one embodiment, $V_{dd}$ carries a 5-volt DC signal modulated by a 0.5-volt peak-to-peak digital signal. Consequently, $V_{dd}$ may swing between 4.5 V and 5 V. Diode-connected transistors 806 and 808 prevents these transistors from turning off by ensuring sufficient voltage difference between the gate and source of each of these transistors.

System Operation

The exemplary control circuit described above allows several unique features and functions to be implemented in a cardiac pressure detection system. One such feature is that the system can address and choose to measure pressure from a number of pressure sensors through the two bus wires residing within a pacing lead. In addition, the system consumes very little power and applies current to a selected pressure sensor for a very short period. This feature significantly reduces the risks imposed by the system and provides unprecedented flexibility which has not been available in conventional pressure detection systems.

Another advantage of the aforementioned control circuit is that, by using specifically designed digital logics, the system can provide power supply and facilitate digital communication simultaneously over the two bus wires. Specifically, the control circuit can extract a DC power supply, derive a clock signal, and capture the FSK-modulated bit sequences at the same time. Furthermore, the special parity bit check mechanism ensures that a pressure sensor is not misconfigured by accident.

In addition, the control circuit disclosed herein can result in an extremely low power consumption. This is because the unique functions of the control circuit are implemented with special device-level designs to minimize leakage current. For example, an exemplary control circuit may adopt specific CMOS designs with long gate lengths to reduce the amount of leakage current through the gates. Additionally, the control circuit may have extra substrate contacts and vias. Because of these low-leakage-current design features, a significant portion of the control circuit can be turned off between two consecutive recharges while the circuit remains in a configured state.

Additional features of the pressure sensor control chip can be implemented in a similar way as is described in U.S. patent application Ser. No. 11/219,305, entitled "Methods and Apparatus for Tissue Activation and Monitoring," filed Sep. 1, 2005 by inventor Mark Zdeblick, which is incorporated by reference herein. Furthermore, examples of additional pressure sensors which can be used with the control circuits described herein can be found in PCT Patent Application No. PCT/US04/41430, filed Dec. 10, 2004; U.S. patent application Ser. No. 11/025,876, filed Dec. 28, 2004; U.S. patent application Ser. No. 11/025,366 filed Dec. 28, 2004; U.S. patent application Ser. No. 11/025,879 filed Dec. 28, 2004; U.S. patent application Ser. No. 11/025,795 filed Dec. 28, 2004; U.S. patent application Ser. No. 11/025,657 filed Dec. 28, 2004; and U.S. patent application Ser. No. 11/025,793, filed Dec. 28, 2004; the disclosures of which applications are incorporated by reference herein.

Figure 39:
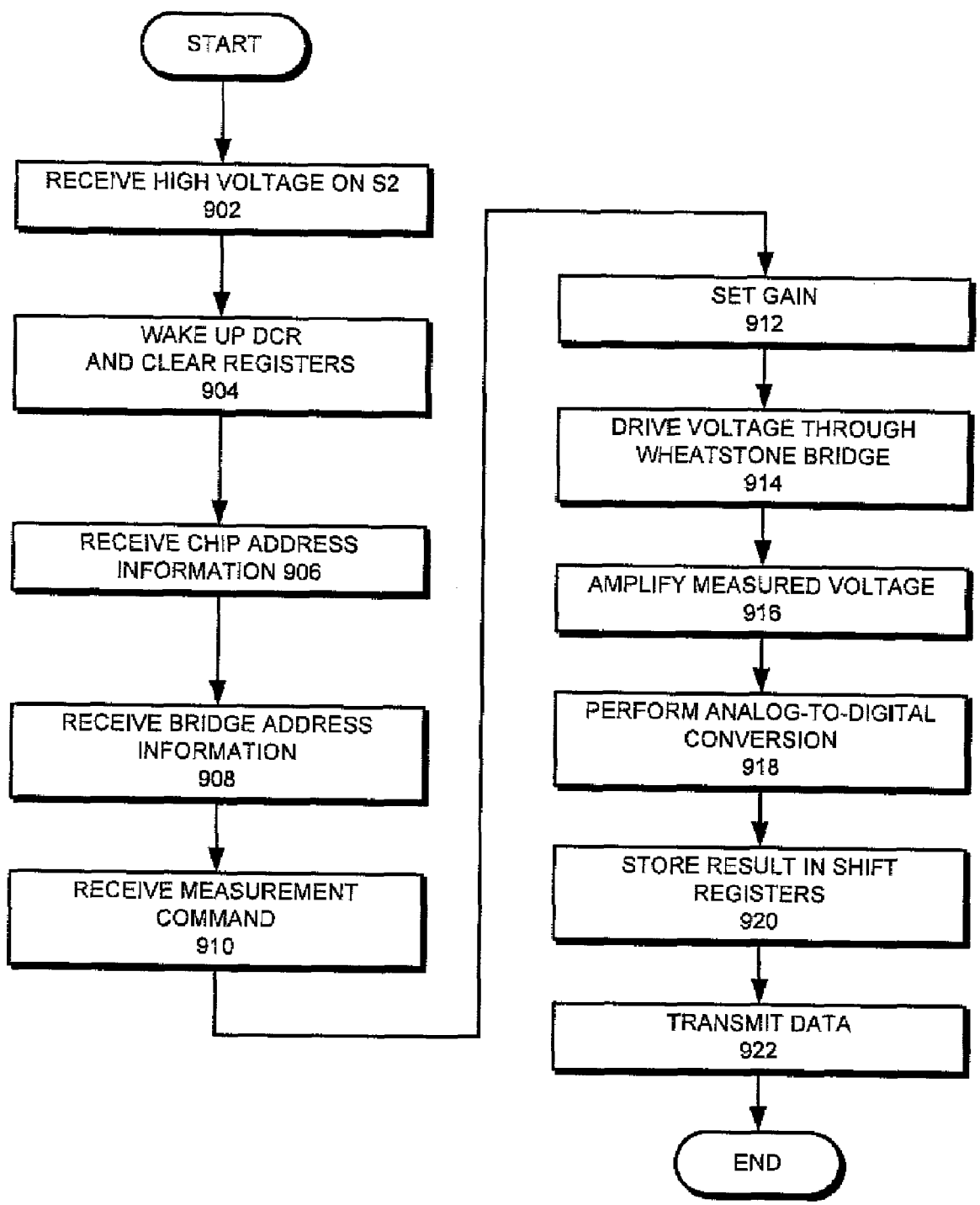
FIG. 39 presents a flow chart illustrating an exemplary process for collecting cardiac pressure signals in accordance with an embodiment of the present invention.

FIG. 39 presents a flow chart illustrating an exemplary process for collecting cardiac pressure signals in accordance with an embodiment of the present invention. During operation, a control chip receives a high voltage on bus wire S2 (step 902). The control chip subsequently wakes up the DCR module and clears the registers (step 904). Next, the control chip receives chip address information (step 906). If the local control chip is selected, the control chip further receives the bridge address information (step 908) and measurement command (step 910). The bridge address information specifies which Wheatstone bridge will be operative, and the measurement command indicates whether the control chip is to measure the selected bridge's offset, or to measure pressure.

The control chip subsequently sets the gain accordingly (step 912). Next, the control chip drives a reference voltage through the Wheatstone bridge (step 914), and amplifies the measured voltage (step 916). The control chip also performs the analog-to-digital conversion (step 918), and stores the results in shift registers (step 920). When the external signal collection and analysis system changes the voltage on S1 and S2 to a constant voltage, the control chip transmits the stored data by modulating the resistance coupled between S1 and S2 (step 922).

Methods of Fabrication

The sensor structures described herein may be fabricated using any convenient protocol. In certain embodiments, the fabrication protocol that is employed is a microfabrication or micromachining protocol, as is employed in MEMS fabrication protocols. As is known in the art, Micro-Electro-Mechanical Systems (MEMS) is the integration of mechanical elements, sensors, actuators, and electronics on a common silicon substrate through microfabrication technology. While the electronics are fabricated using integrated circuit (IC) process sequences (e.g., CMOS, Bipolar, or BICMOS processes), the micromechanical components are fabricated using compatible "micromachining" processes that selectively etch away parts of the silicon wafer or add new structural layers to form the mechanical and electromechanical devices. Representative fabrication protocols for producing various sensor structures described above are reviewed in greater detail in U.S. patent application Ser. No. 11/219,305, filed Sep. 1, 2005; PCT Patent Application No. PCT/US04/ 41430, filed Dec. 10, 2004; U.S. patent application Ser. No. 11/025,876, filed Dec. 28, 2004; U.S. patent application Ser. No. 11/025,366 filed Dec. 28, 2004; U.S. patent application Ser. No. 11/025,879 filed Dec. 28, 2004; U.S. patent application Ser. No. 11/025,795 filed Dec. 28, 2004; U.S. patent application Ser. No. 11/025,657 filed Dec. 28, 2004; and U.S. patent application Ser. No. 11/025,793, filed Dec. 28, 2004; the disclosures of which applications are incorporated by reference herein.

Systems

Also provided are systems that include the subject sensors. The systems include the subject sensor structures, as well as additional components that find use in particular pressure sensing applications. For example, in certain embodiments, the sensor system may include a processor for converting responses of the transducers of a sensor structure to measurements of pressure changes in the volume being monitored. In some embodiments, the system may include a multiplexed catheter coupled with the at least one conductive wire via a conductive liquid or gel. At least one additional pressure sensor may also be located apart from the sensor structure for providing measurement of a gauge pressure.

A particularly advantageous design for semi-permanent and permanent embodiments, i.e., implantable embodiments, of the inventive low-drift pressure sensor is the approach of using one common connection and a single wire running to each individual connection. This is a bus type configuration. In this design of the innovative low-drift pressure sensing, the opportunity is provided for a long string of pressure sensors implanted along the length of an implanted device, such as a cardiac catheter.

In contrast to the temporary configurations, a bus configuration provides a single wire or conductor which serves all of the low-drift sensor components for one side of the electrical connection. This bus configuration allows a small denier size, which can be pivotal in providing for instance, a cardiac timing device in an acceptable form for semi permanent or permanent uses. This bus configuration also plays on the strength of the small dimensions available for the low-drift pressure sensor components. This configuration is further described in Published PCT Application No. WO 2004/ 052182 and U.S. patent application Ser. No. 10/734,490, the disclosure of which is herein incorporated by reference.

In the permanent implant embodiment of the present inventive low-drift pressure sensing device system, conductors are selected which have a relatively high fatigue life. The capacity to survive 400 million cycles prior to failure is the typical requirement for long term implant cardiac devices. For the construction of devices meeting these requirements, several design approaches are particularly suitable.

For permanent implant cardiac timing devices, the inventive low-drift pressure sensors may be incorporated into the satellite technology which has been developed by some of the present inventors. These applications provide multiplexing systems developed by some of the present inventors with which the present inventive low-drift pressure sensors very usefully employed.

The systems may further include a variety of different effector element, which elements may employ the satellites or structures distinct from the satellites. The effectors may be intended for collecting data, such as but not limited to pressure data, volume data, dimension data, temperature data, oxygen or carbon dioxide concentration data, hematocrit data, electrical conductivity data, electrical potential data, pH data, chemical data, blood flow rate data, thermal conductivity data, optical property data, cross-sectional area data, viscosity data, radiation data and the like. As such, the effectors may be sensors, e.g., temperature sensors, accelerometers, ultrasound transmitters or receivers, voltage sensors, potential sensors, current sensors, etc. Alternatively, the effectors may be intended for actuation or intervention, such as providing an electrical current or voltage, setting an electrical potential, heating a substance or area, inducing a pressure change, releasing or capturing a material or substance, emitting light, emitting sonic or ultrasound energy, emitting radiation and the like.

Effectors of interest include, but are not limited to, those effectors described in the following applications by at least some of the inventors of the present application: U.S. patent application Ser. No. 10/734,490 published as 20040193021 titled: "Method And System For Monitoring And Treating Hemodynamic Parameters"; U.S. patent application Ser. No. 11/219,305 published as 20060058588 titled: "Methods And Apparatus For Tissue Activation And Monitoring"; International Application No. PCT/US2005/046815 titled: "Implantable Addressable Segmented Electrodes"; U.S. patent application Ser. No. 11/324,196 titled "Implantable Accelerometer-Based Cardiac Wall Position Detector"; U.S. patent application Ser. No. 10/764,429, entitled "Method and Apparatus for Enhancing Cardiac Pacing," U.S. patent application Ser. No. 10/764,127, entitled "Methods and Systems for Measuring Cardiac Parameters," U.S. patent application Ser. No. 10/764,125, entitled "Method and System for Remote Hemodynamic Monitoring"; International Application No. PCT/US2005/046815 titled: "Implantable Hermetically Sealed Structures"; U.S. application Ser. No. 11/368, 259 titled: "Fiberoptic Tissue Motion Sensor"; International Application No. PCT/US2004/041430 titled: "Implantable Pressure Sensors"; U.S. patent application Ser. No. 11/249, 152 entitled "Implantable Doppler Tomography System," and claiming priority to: U.S. Provisional Patent Application No. 60/617,618; International Application Serial No. PCT/US05/ 39535 titled "Cardiac Motion Characterization by Strain Gauge". These applications are incorporated in their entirety by reference herein.

In addition, the subject systems may include a processing element which is configured to run the system to provide the desired application, such as the various representative applications discussed below.

Methods

Also provided are methods of using the subject sensors structures and systems that include the same. In general, methods of detecting, i.e., sensing, pressure changes in a volume are provided. In practicing the subject methods, a sensor structure of the present invention is contacted with a volume to be monitored. Contact of the sensor and the volume is achieved using any convenient approach, where the particular approach will vary depending on the location of the volume. In certain embodiments where the volume is an internal location of a patient, such as a heart chamber, contact is achieved by implanting the sensor at a suitable location in contact with the volume.

Contact of the sensor and the volume is then maintained over the period of time that pressure changes are to be detected or monitored. While the sensor is contacted with the volume, a suitable voltage is applied to the input(s) of the strain transducer elements. The resultant output is then monitored, and the resultant output signal is used to detect changes in pressure of the volume, as is known in the art. Because the subject sensors are low drift sensors, an implanted sensor can be employed to accurately monitor pressure changes in a volume for extended periods of time without recalibration following implantation, e.g., for periods of at least about 1 day, such as at least about 1 week, including at least about 1 month or longer, such as at least about 6 months, at least about 1 year, at least about 5 years, etc.

The subject methods and devices find use in any of a number of different contexts. In one embodiment, for example, a sensor device may be implanted in a body chamber to measure and monitor pressure therein. For example, a sensor (or sensors) may be implanted in one or more heart walls to monitor pressure changes in one or more heart chambers. Deflections in a diaphragm of a sensor device may be converted to pressure measurements which may be used, for example, by a physician to help guide treatment decisions. Such data may also be used to automatically adjust a pressure-responsive pacemaker implanted in a patient. Applications in which the subject devices and methods find use are further described in: U.S. patent application Ser. No. 10/764,429 entitled "Method and Apparatus for Enhancing Cardiac Pacing"; U.S. patent application Ser. No. 10/764,127 entitled "Methods and Systems for Measuring Cardiac Parameters"; U.S. patent application Ser. No. 10/764,125 entitled "Method and System for Remote Hemodynamic Monitoring"; and U.S. patent application Ser. No. 10/734,490 entitled "Method and System for Monitoring and Treating Hemodynamic Parameters"; the disclosures of which are herein incorporated by reference.

As indicated above, the present invention provides methods, apparatuses and systems for employing low drift, permanent implanted pressure sensors for optimizing medical treatment, such as for cardiac resynchronization intervention, arrhythmia management, ischemia detection, coronary artery disease management, and heart failure management, among other types of applications. These representative applications are now reviewed in greater detail below.

There are special clinical advantages for the inventive permanent internal pressure sensors capacity to provide remote, real time internal pressure data. For instance, by means of the inventive devices, pressure sensor data can be provided directly to the physician's office for monitoring patient progress, allowing the physician to effectively modify pharmaceutical intervention without requiring patient travel. This application of the present invention is particularly advantageous for patients in remote areas.

Additionally, using the present inventive implantable pressure sensor devices, physicians are able to monitor patients during normal daily activities. This capacity of the inventive implantable pressure sensors encourages heart failure patients to resume health promoting increases in physical exertion. In some cases, patients will, for the first time, be able to undertake a program of increasingly active exercise that increases the quality of their lives and provides overall clinical improvement.

The inventive implantable pressure sensors can be effectively employed by specialists, such as congestive heart failure cardiologists, to address a patient's medication, diet and exercise regimen in response to real time physiologic data such as cardiac output which may be determined from implantable pressure sensor readings.

The totally implantable system embodiment of the present invention, which may include intracardiac leads and other structures utilizing pressure sensors, can be further modified in another embodiment of the present invention to optimize clinical improvements.

A representative application for the inventive permanently implantable pressure sensors within the human body, with particular focus on the hemodynamics system, is implantation in one or more of the four chambers of the heart. In such locations pressure sensors give a global indicator of myocardial performance. Such a global indicator essentially integrates all the various flows as well as contractility contributions of separate myocardial wall segments. These indicators further provide performance indicators of the various heart valves in combination. This global assessment is a very valuable tool in assessing and treating heart failure.

Ratio-metric analysis of data from the present implantable pressure sensor devices can be used to derive clinically important parameters, such as ischemic burden of a patient's heart, cardiac output, and other valuable physiologic information. Ratio-metric analysis is the comparison of a pressure signal in one or more chambers with other such signals, or indeed other more local signals. Ratio-metric analysis has been described previously in the context cardiac wall motion, local strain and other factors. This analysis as applied to the present invention will be well understood by the skilled artisan.

Other applications for pressure sensors permanently implanted within the human cardio vascular system include providing measurements of coronary artery disease progression. This application is accomplished by implanting a plurality of sensors along the distribution of, for example, a coronary artery. The appropriate placement of the inventive sensor can also be accomplished by incorporating the inventive micro pressure sensors within the proximal and distal end of a coronary stent. The pressure gradient which is provided by the inventive device is used to potentially derive flow data and also the resistive resistance to flow between the two pressure sensors. The change in this resistance over time can be used as an indicator of, for example, re-stenosis or progression of coronary artery disease that is arteriosclerosis.

Artificial heart valve analysis using the inventive implantable pressure sensors is related to coronary artery disease assessment. Artificial heart valve analysis can be accomplished with pressure sensor placement within the chambers of the heart proximal and distal. This placement would be on the inter-cardiac area, or within each chamber heart separated by either a natural or an artificial heart valve. In the latter case, the sensors are incorporated into the artificial heart valve itself. In the former case, the sensors could be implanted through less invasive means, or at the time of a reparative surgery, such as angioplasty. The inventive implantable pressure sensors so positioned provide a real time indication of the pressure gradient across a valve. This data can be used to determine the degree of leakiness or stenosis of said valve. Such sensors also provide information on how leakiness or stenosis of the valve is progressing over time.

When combined with other sensors, additional information can be derived from the present implantable pressure sensors. The additional sensors, such as those previously described, would be located within chambers assessing the degree to which pressure is being generated. By example, the chambers selected can be the left ventricle. As compared to the inter-cavity pressures in the left ventricle, that gradient across the mitral valve and the wall strain across one or more segments of the heart provides a very comprehensive picture of how a heart is performing. The left ventricular performance and the various contributions of contractility, synchrony vs. dissynchrony and mitral regurgitation, for example, can be quantitatively assessed.

A drawback in today's management methods is that a multiparametric analysis is often problematic. Clinically, in many cases decisions regarding valvular replacement, that is surgical valvular replacement, are made by the clinician on a less objective basis than would be desirable. The present invention thus makes clinically available multiparametric analysis information, providing for better informed case decisions.

Another application for the inventive permanently implantable pressure sensor is in an essentially fully implantable Swan Ganz, or pulmonary artery catheter. In this implementation the well understood pulmonary artery catheter would be employed. A pulmonary artery catheter is typically introduced from a jugular or subclavian venous orientation passing through the right atrium, right ventricle, right ventricular outflow track and into the pulmonary circulation. Such catheters when containing the inventive implantable pressure sensors provide the clinician with both right atrial and right ventricular pressures.

Pulmonary artery pressure can also be assessed using the inventive implantable pressure sensors. This can be accomplished when the catheter is wedged by blowing up and inflating a balloon. That approach provides a pressure through an essentially a static column of fluid to the left atrium. A pulmonary capillary wedge pressure typically correlates very well to the left atrial pressure. The reading is obtained from the right side of the heart. Furthermore, by injecting heat indicator dye or cold fluid and integrating a signal in a appropriate sensor, the distal tip of the pulmonary catheter, e.g., Swan Ganz catheter, the clinician is able to determine cardiac output on a reasonably reliable basis.

With the inventive micro pressure sensors a permanently implantable or temporarily implantable pulmonary artery catheter can be assembled. With this device, the pressure sensors may be left in the pulmonary artery in a stent like structure. Alternatively, the pressure sensors are deployed along a catheter structure passing through the heart but terminating in a subcutaneous coil. This configuration provides for the data to be communicated to the outside world.

The inventive devices being capable of transmitting information to remote sites when implanted in the patient enables congestive heart failure patients a new level of freedom and safety. For example, with such a device, a patient is able to move to a regular bed and out of ICU when medications are being titrated. Previously, invasive approaches were required to provided the extremely detailed hemo-dynamic monitoring of cardiac performance needed for such titrations.

Currently in such a situation, the temporary implantable Swan Ganz catheter is typically removed after several days, at which point the patient moves home. However, by fully implanting the inventive system into a permanently implantable form, the patient is no longer tethered to the various equipment that needs to be in the intensive care unit.

Furthermore, the permanently implanted device eliminates a direct route for infectious agents to enter the central circulation of the patient. This reduces the not insignificant risk of sepsis and other infections, which is significant in these patients who typically have impaired cardiac function and reduced cardiac output. For these and other reasons, such patients are more vulnerable to infection.

Another application for the subject invention is using pressure sensors deployed within a triple A stent graft. This is the case where an abdominal aortic aneurism is repaired by an endovascular graft. Typically, the endovascular graft is introduced from the femoral approach in a minimally invasive manner. The present implantable pressures sensors are advantageous for detecting any issues with graft sealing. The necessary information can be obtained by pressure sensors on the outside of the stent graft in the area of the aneurism in order to provide early detection of leaks.

An advantage of the inventive implantable pressure sensors in this case is that they eliminate or reduce the need for routine follow up CT scans. Such scans are currently required to follow progression of the aneurism after implantation of the endovascular stent graft. Clinically, typically issues in such cases are migration of the stent graft over time and loss of sealing.

Another new application provided by the inventive implantable pressure sensors uses a similar approach to the stent graft described above. In this case, a micro stent graft is provided within a neurovascular aneurism. Such aneurysms are, for instance, one closed off through a mircoinvasive or minimally invasive approach via catheters, such as a Guglielmi Detachable Coil (GDC). This arrangement allows the clinician to continue monitoring the pressure profile of that procedure, or for the period following the procedure.

In another application, the inventive permanent pressure sensors are implanted in a peripheral artery or a central artery for purposes of determining the pulse pressure. The pulse pressure is used to correlate the appropriate calibration to the cardiac output of the patient. This embodiment of the inventive device can be used to improve resynchronization of a dissynchronous heart in the case of cardiac re synchronization therapy or management of congestive heart failure patients by pharmacologic means.

Cardiac resynchronization therapy is an important new medical intervention for patients suffering from congestive heart failure. In congestive heart failure, symptoms develop due to the inability of the heart to function sufficiently well as a mechanical pump to supply the body's physiologic needs. Congestive heart failure is characterized by gradual decline in cardiac function punctuated by severe exacerbations leading eventually to death. It is estimated that over five million patients in the United States suffer from this malady.

The aim of resynchronization pacing is to induce the interventricular septum and the left ventricular free wall to contract at approximately the same time. Resynchronization therapy seeks to provide a contraction time sequence which will most effectively produce maximal cardiac output with minimal total energy expenditure by the heart. Prior to the present invention, there were no useful clinically available means of determining optimal CRT settings on a substantially automatic or a real-time, machine readable basis.

The optimal timing is calculated by reference to hemodynamic parameters such as dP dt, the first derivative of the pressure waveform in the left ventricle. The dP dt parameter is a well-documented proxy for left ventricular contractility. In this manner, synchrony is assessed between various parameters such as a dP dt, the first derivative of the pressure curve correlated to maximal relative velocity during systole towards the center of the ventricle. Also provided is the actual maximum position of displacement on a net basis of the monitored wall segments towards the center. The present inventive implantable pressure sensors allow real time analysis of the efficacy of a particular resynchronization electrode placement or pacing timing, as well as providing immediate, real time hemodynamic parameters.

The clinically established data point for CRT therapy is pressure-pressure loops. In the general case it is thought that in the healthy heart, both ventricles contract at the same time. In that case, peak pressures are achieved in both ventricles simultaneously. This test has been employed as a measure of potential synchrony.

In dissynchronous hearts, the pressure peak typically occurs at different times, suggesting that the muscle is contracting at different times. This difference in contraction can now be directly measured with the present inventive implantable pressure sensor devices. Comparison to RV and/or LV pressures will add global data to other current methods for assessing heart contraction synchrony.

Additional clinical cardiology uses for the inventive implantable pressure sensors include applications as ischemia detectors. It is well understood that, before biochemical or electrical markers of cardiac ischemia present themselves, wall motion is first affected with the ischemic region showing increased stiffness and decreased contraction, resulting in changed pressure profiles, whether absolute or relative between heart chambers. Such changes as they effect internal cardiac pressures can be readily detected by the implantable pressure sensor system currently invented.

The present invention can establish a baseline pressure reading for patients at risk for ischemia. This reading provides a profile of normal/beginning heart pressure in a particular patient. The clinician then sets a pressure standard, variation beyond which an alert would be provided.

The inventive implantable pressure sensors can be employed as arrhythmia detectors. Currently implantable defibrillator systems are challenged by differentiating between a variety of benign and malignant arrhythmias relying as they do primarily on electrical means of discrimination. Real time dynamic sensing of changed internal cardiac pressures using the present inventive implantable pressure sensors marks a significant advantage in detecting arrhythmias.

Using the implantable pressure sensor devices of the present invention, the timing and displacement of the contraction from any heart chamber can be assessed. In this way, the maximum contraction can be stimulated to occur at the time most efficient from the standpoint of producing the greatest hemodynamic output for the least amount of effort.

Other derived hemodynamic parameters will be recognized by the artisan. In an additional embodiment of the present invention, additional sensors deployed along other areas of the heart provide data that provide complete characterization of the function of the ventricle or ventricles. This wealth of real time information is continuously available to the clinician on a permanent implantable basis. This ongoing pressure sensor data can also be provided to the pacing system controller directly. This allows automated optimization of pacing timing to that which will prove most clinically beneficial.

Kits

As summarized above, also provided are kits and systems for use in practicing the subject methods. The kits and systems at least include the subject sensors and/or systems that include the same, as described above. The kits and systems may also include a number of optional components that find use with the subject sensors, including but not limited to, implantation devices, data analysis elements, processing algorithms recorded on suitable media, etc.

In certain embodiments of the subject kits, the kits will further include instructions for using the subject devices or elements for obtaining the same (e.g., a website URL directing the user to a webpage which provides the instructions), where these instructions are typically printed on a substrate, which substrate may be one or more of: a package insert, the packaging, reagent containers and the like. In the subject kits, the one or more components are present in the same or different containers, as may be convenient or desirable.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for measuring cardiac pressure, the method comprising:
   providing a power supply voltage for a number of control chips over two wires, each control chip coupled to one or more pressure sensors;
   transmitting a number of bit sequences carrying address information with the power supply voltage over the two wires;
   configuring a pressure sensor for measuring cardiac pressure; and
   receiving a digital signal indicating a measured cardiac pressure,
   wherein the one or more pressure sensors includes a Wheatstone bridge and wherein the transmitting a number of bit sequences over the two wires involves modulating the power supply voltage with a digital signal.

2. The method of claim 1, wherein the digital signal is a frequency-shift-keying (FSK) modulated signal.

3. The method of claim 1, wherein the power supply voltage is provided for approximately 50 μs.

4. A method for measuring cardiac pressure, the method comprising:
   providing a power supply voltage for a number of control chips over two wires, each control chip coupled to one or more pressure sensors;
   transmitting a number of bit sequences carrying address information with the power supply voltage over the two wires;
   configuring a pressure sensor for measuring cardiac pressure; and
   receiving a digital signal indicating a measured cardiac pressure,
   wherein the one or more pressure sensors includes a Wheatstone bridge, wherein the transmitting a number of bit sequences over the two wires involves modulating the power supply voltage with a digital signal, and wherein the power supply voltage is provided for approximately 50 μs.

5. An integrated circuit for measuring cardiac pressure, the integrated circuit comprising:
   a first terminal coupled to a conductor provided in an implanted lead;
   a second terminal; and
   a control circuit comprising a clock recovery circuit, the control circuit coupled to the first and second terminals wherein, during a first time interval, when digital configuration signals are provided from the controller on the first terminal, the control circuit selectively configures a selected pressure sensor, and wherein, during a second time interval, the control circuit administers electrical signals to the pressure sensor and measures a response voltage from the pressure sensor, and wherein the clock recovery circuit recovers a clock signal from received configuration signals.

6. The integrated circuit of claim 5, wherein during a third time interval the control circuit communicates a digital signal indicating the measured voltage through the first and second terminals.

7. The integrated circuit of claim 5, wherein the second terminal is coupled to a conductor provided in the implantable lead.

* * * * *